US012594400B2

(12) United States Patent
McGuinn et al.

(10) Patent No.: US 12,594,400 B2
(45) Date of Patent: Apr. 7, 2026

(54) DELIVERY SYSTEM WITH A TORQUEABLE CATHETER SHAFT

(71) Applicant: MEDTRONIC, INC., Minneapolis, MN (US)

(72) Inventors: Alan McGuinn, Oranmore (IE); Niall Duffy, Ballybrit (IE)

(73) Assignee: MEDTRONIC, INC., Minneapolis, MN (US)

( * ) Notice: Subject to any disclaimer, the term of this patent is extended or adjusted under 35 U.S.C. 154(b) by 301 days.

(21) Appl. No.: 18/253,988

(22) PCT Filed: Dec. 20, 2021

(86) PCT No.: PCT/US2021/064292
§ 371 (c)(1),
(2) Date: May 23, 2023

(87) PCT Pub. No.: WO2022/140228
PCT Pub. Date: Jun. 30, 2022

(65) Prior Publication Data

US 2023/0405270 A1 Dec. 21, 2023

Related U.S. Application Data

(60) Provisional application No. 63/193,319, filed on May 26, 2021, provisional application No. 63/129,194, filed on Dec. 22, 2020.

(51) Int. Cl.
*A61M 25/00* (2006.01)
*A61F 2/24* (2006.01)
(Continued)

(52) U.S. Cl.
CPC ....... *A61M 25/0053* (2013.01); *A61F 2/2433* (2013.01); *A61F 2/958* (2013.01);
(Continued)

(58) Field of Classification Search
CPC .......... A61M 25/0053; A61M 25/0136; A61M 25/0147; A61M 2025/1061;
(Continued)

(56) References Cited

U.S. PATENT DOCUMENTS

| | | | |
|---|---|---|---|
| 5,425,712 | A | 6/1995 | Goodin |
| 6,246,914 | B1 | 6/2001 | de la Rama et al. |

(Continued)

FOREIGN PATENT DOCUMENTS

| | | | |
|---|---|---|---|
| EP | 2397108 | A2 | 12/2011 |
| WO | 2009075989 | A1 | 6/2009 |

(Continued)

OTHER PUBLICATIONS

Written Opinion and International Search Report issued May 13, 2022 in Intl. App. No. PCT/US2021/064292, 12 pages.

*Primary Examiner* — Andrew Restaino
(74) *Attorney, Agent, or Firm* — MEDLER FERRO WOODHOUSE & MILLS PLLC

(57) ABSTRACT

A catheter shaft includes a proximal portion with a first polymer having a first stiffness and a first portion of a tubular braid component extending within the first polymer, an intermediate portion with a second polymer having a second stiffness and a second portion of the tubular braid component extending within the second polymer, and a distal portion with a third polymer having a third stiffness, a third portion of the tubular braid component extending within the third polymer, and a hypotube extending within the third polymer. The hypotube is configured for elastic deformation and includes a sidewall cut with a pattern. Along an overlap segment of the distal portion, the third portion of the tubular braid component and the hypotube overlap each other. The outer shaft is configured for improved torque transmission.

20 Claims, 33 Drawing Sheets

(51) Int. Cl.
*A61F 2/958* (2013.01)
*A61M 25/01* (2006.01)
*A61M 25/10* (2013.01)

(52) U.S. Cl.
CPC ..... *A61M 25/0136* (2013.01); *A61M 25/0147* (2013.01); *A61M 2025/1061* (2013.01); *A61M 2205/583* (2013.01)

(58) Field of Classification Search
CPC ........ A61M 2205/583; A61M 25/0051; A61M 25/0138; A61M 25/0054; A61M 25/10; A61M 25/0045; A61F 2/2433; A61F 2/958
See application file for complete search history.

(56) References Cited

U.S. PATENT DOCUMENTS

| | | | | |
|---|---|---|---|---|
| 6,355,027 | B1 | 3/2002 | Le et al. | |
| 6,508,806 | B1 | 1/2003 | Hoste | |
| 6,858,024 | B1 | 2/2005 | Berg et al. | |
| 7,879,021 | B2 | 2/2011 | Drewes, Jr. | |
| 8,449,526 | B2 | 5/2013 | Snyder et al. | |
| 8,540,695 | B2 | 9/2013 | Shimogami et al. | |
| 8,968,379 | B2 | 3/2015 | Pryor | |
| 9,114,229 | B2 | 8/2015 | Fuentes | |
| 9,339,628 | B2 | 5/2016 | Adams et al. | |
| 9,782,561 | B2 * | 10/2017 | Kugler | A61M 25/0053 |
| 9,814,618 | B2 | 11/2017 | Nguyen et al. | |
| 10,076,638 | B2 * | 9/2018 | Tran | A61M 25/0141 |
| 10,130,791 | B2 | 11/2018 | Heideman et al. | |
| 10,463,439 | B2 | 11/2019 | Joseph et al. | |
| 10,589,060 | B2 | 3/2020 | Beeckler et al. | |
| 10,695,541 | B1 * | 6/2020 | Calhoun | A61B 3/102 |
| 10,758,709 | B2 * | 9/2020 | Calabrese | A61B 1/008 |
| 11,406,791 | B2 * | 8/2022 | Lippert | A61M 25/0069 |
| 2004/0102719 | A1 * | 5/2004 | Keith | A61M 25/0147 600/585 |
| 2005/0020974 | A1 * | 1/2005 | Noriega | A61M 25/0138 604/95.04 |
| 2007/0270679 | A1 * | 11/2007 | Nguyen | A61M 25/0043 600/585 |
| 2009/0270800 | A1 * | 10/2009 | Spurchise | A61M 25/0074 604/95.04 |
| 2010/0217374 | A1 | 8/2010 | Willard et al. | |
| 2011/0238041 | A1 | 9/2011 | Lim et al. | |
| 2012/0323175 | A1 * | 12/2012 | Vogelbaum | A61M 25/0102 604/95.04 |
| 2015/0297346 | A1 | 10/2015 | Duffy et al. | |
| 2017/0216560 | A1 * | 8/2017 | Gregorich | A61M 25/0051 |
| 2017/0224956 | A1 * | 8/2017 | Melsheimer | A61B 1/0055 |
| 2018/0126124 | A1 * | 5/2018 | Winston | A61M 25/0052 |
| 2018/0193591 | A1 | 7/2018 | Jaroch et al. | |
| 2018/0228502 | A1 | 8/2018 | Shaffer et al. | |
| 2019/0008639 | A1 * | 1/2019 | Landon | A61F 2/243 |
| 2019/0374751 | A1 * | 12/2019 | Finson | A61M 25/10182 |

FOREIGN PATENT DOCUMENTS

| | | | |
|---|---|---|---|
| WO | 2016090025 | A1 | 6/2016 |
| WO | 2016114981 | A1 | 7/2016 |
| WO | 2017044131 | A1 | 3/2017 |

* cited by examiner

L1
126
124
122
129
116
118
114
112

128A
121
150
111
120
112/122

122

C
B 128B
123
112/124

124

3400

3402 — Aligning image plane with anatomy at a target site

3404 — Delivering an implantable medical device to the target site

3406 — Positioning the implantable medical device in an axial direction at the target site 3408 — Aligning a circumferential or rotational orientation of the implantable medical device at the target site 3410 — Deploying the implantable medical device at the target site

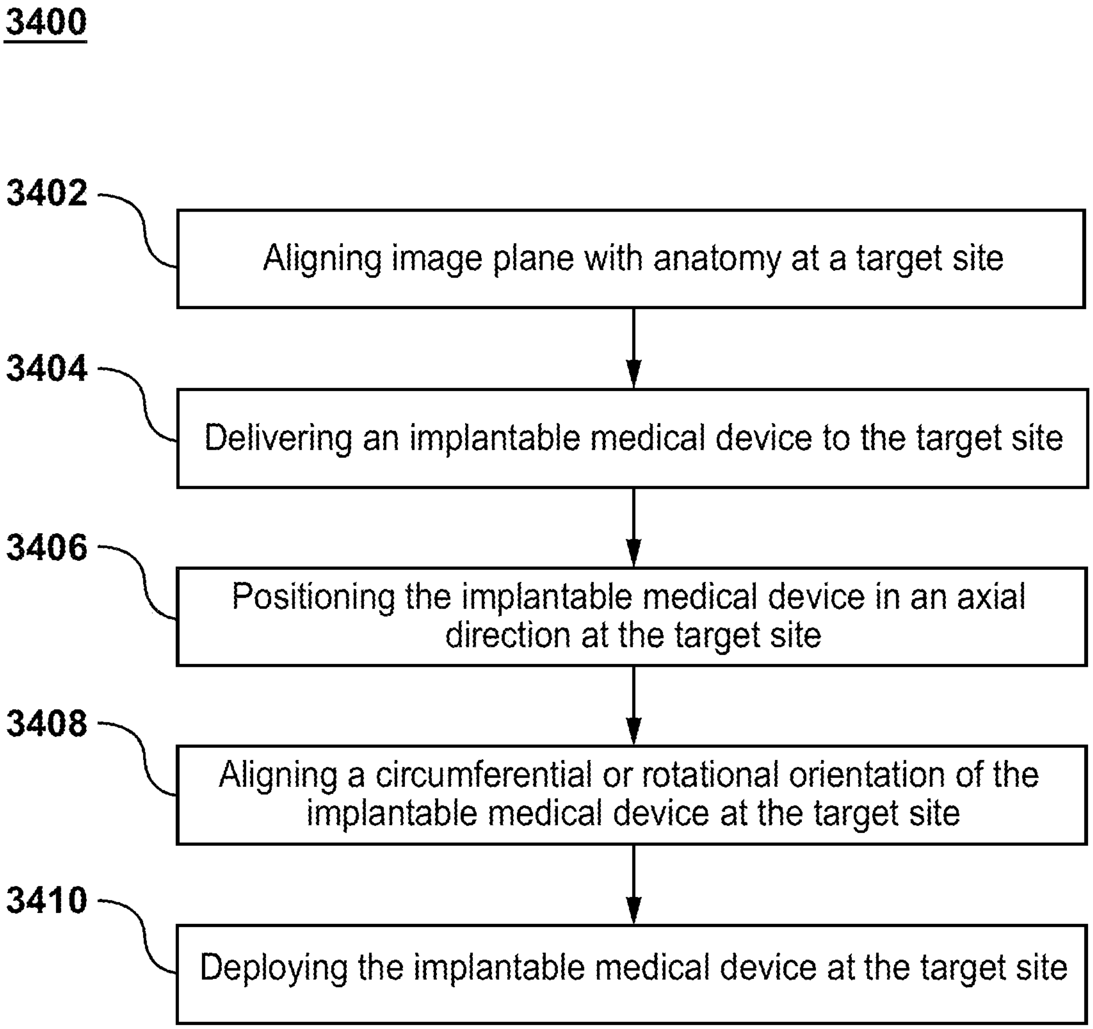

FIG. 34

DELIVERY SYSTEM WITH A TORQUEABLE CATHETER SHAFT

CROSS-REFERENCE TO RELATED APPLICATIONS

This application is a National Stage of International Application No. PCT/US2021/064292, filed Dec. 20, 2021, which claims the benefit of U.S. Provisional Patent Application Ser. No. 63/193,319, filed May 26, 2021, and U.S. Provisional Patent Application Ser. No. 63/129,194, filed Dec. 22, 2020, each of which is hereby incorporated by reference in its entirety for all purposes.

FIELD

Embodiments hereof relate to catheters and more particularly to a delivery system having a torqueable catheter shaft.

BACKGROUND

A variety of catheters for delivering a therapy and/or monitoring a physiological condition have been implanted or proposed for implantation in patients. Catheters may deliver therapy to, and/or monitor conditions associated with, the heart, muscle, nerve, brain, stomach or other organs or tissue. Many catheters are tracked through the vasculature to locate a therapeutic or diagnostic portion of the catheter at a target site. Such catheters must have flexibility to navigate the twists and turns of the vasculature, sufficient stiffness in the proximal portion thereof to be pushed through the vasculature alone or over a guidewire or through a lumen, and the capability of orienting a distal portion thereof in alignment with an anatomical feature at the target site so that a diagnostic or therapeutic procedure can be completed. In general terms, the catheter body must also resist kinking and be capable of being advanced through access pathways that twist and turn, sometimes abruptly at acute angles.

For certain procedures, it may be necessary for the clinician to accurately steer or deflect the catheter so that a distal opening thereof may be aligned with an ostium of a branch or side vessel. The distal portions of catheters frequently need to be selectively curved or bent and straightened again while being advanced within the patient to steer the catheter distal end into a desired body lumen or chamber. For example, it may be necessary to direct the catheter distal end through tortuous anatomies and/or into a branch at a vessel bifurcation. In addition, some procedures require high accuracy in guidewire orientation. For example, often patient's arteries are irregularly shaped, highly tortuous and very narrow. The tortuous configuration of the arteries may present difficulties to a clinician in advancement of a catheter to a treatment site.

In addition to bending or deflecting the distal portion of the catheter during navigation, the clinician may also need to rotate or torque the catheter when advancing the catheter to a treatment site in order to achieve proper or desired alignment of the catheter. However, manually torqueing the delivery system may require significant force to combat recoiling forces.

Thus, a need in the art still generally exists for improved apparatuses and methods for navigating a catheter through or within a patient's anatomy.

BRIEF SUMMARY

According to a first embodiment hereof, the present disclosure provides a balloon catheter including an outer shaft, a balloon, and an inflation lumen. The outer shaft has an elongate tubular body extending from a proximal end to a distal end and defining a central lumen therethrough, the elongate tubular body having a proximal portion, a distal portion, and an intermediate portion extending between the proximal portion and the distal portion. The balloon attached to the distal end of the elongate tubular body, the balloon being expandable from a first diameter to a second diameter greater than the first diameter. The inflation lumen is in fluid communication with an interior of the balloon. The proximal portion includes a first polymer having a first stiffness and a first portion of a tubular braid component extending within the first polymer. The intermediate portion includes a second polymer having a second stiffness and a second portion of the tubular braid component extending within the second polymer. The distal portion includes a third polymer having a third stiffness, a third portion of the tubular braid component extending within the third polymer, and a hypotube extending within the third polymer, the hypotube being configured for elastic deformation and having a proximal end, a distal end, a length between the proximal end and the distal end, and a sidewall cut with a pattern. Along an overlap segment of the distal portion, the third portion of the tubular braid component overlaps the length of the hypotube or the length of the hypotube overlaps the third portion of the tubular braid component.

In an aspect of the first embodiment, and in combination with any other aspects herein, the disclosure provides the second stiffness is less than the first stiffness and the third stiffness is less than the second stiffness.

In an aspect of the first embodiment, and in combination with any other aspects herein, the disclosure provides that the balloon catheter further includes an inner shaft disposed through the central lumen of the elongate tubular body of the outer shaft. A proximal end of the balloon is attached to the distal end of the elongate tubular body and a distal end of the balloon is attached to a distal end of the inner shaft. The inflation lumen is annular and is defined between the outer shaft and the inner shaft.

In an aspect of the first embodiment, and in combination with any other aspects herein, the disclosure provides the inflation lumen is defined in a sidewall of the outer shaft, the inflation lumen terminating proximal to the distal end of the elongate tubular body.

In an aspect of the first embodiment, and in combination with any other aspects herein, the disclosure provides that the balloon catheter further includes a handle coupled to the proximal end of the elongate tubular body. The handle includes a luer having an inflation port configured to receive inflation fluid, the inflation port being in fluid communication with the inflation lumen. In an embodiment, the outer shaft is rotated by rotation of the handle. In an embodiment, the outer shaft is rotated by actuation of an actuator on the handle. In an embodiment, the luer of the handle further includes a guidewire port configurated to slidingly receive a guidewire therethrough, the guidewire port being in fluid communication with the central lumen of the elongate tubular body of the outer shaft.

In an aspect of the first embodiment, and in combination with any other aspects herein, the disclosure provides a pull wire lumen is defined in a sidewall of the outer shaft, the pull wire lumen terminating proximal to the distal end of the elongate tubular body.

In an aspect of the first embodiment, and in combination with any other aspects herein, the disclosure provides that the balloon catheter further includes a pull wire slidingly disposed through the pull wire lumen. A distal end of the pull wire is coupled to the sidewall of the elongate tubular body and a proximal end of the pull wire is coupled to an actuator of a handle, and wherein the pull wire is operable to bend the elongate tubular body for steering the balloon catheter in situ. In an embodiment, the pull wire has a braided construction.

In an aspect of the first embodiment, and in combination with any other aspects herein, the disclosure provides that the sidewall of the elongate tubular body has a non-uniform cross-sectional thickness, the pull wire lumen extending within a thicker wall section of the sidewall.

In an aspect of the first embodiment, and in combination with any other aspects herein, the disclosure provides that the pull wire lumen is formed via an elongated radial protrusion that extends along an inner surface of the elongate tubular body and protrudes into the central lumen of the elongate tubular body.

In an aspect of the first embodiment, and in combination with any other aspects herein, the disclosure provides that a pull wire is slidingly disposed through the pull wire lumen, wherein a distal end of the pull wire is coupled to the sidewall of the elongate tubular body and a proximal end of the pull wire is coupled to an actuator of the handle, and wherein the pull wire is operable to bend the elongate tubular body for steering the balloon catheter in situ, and wherein the sidewall of the elongate tubular body has a substantially uniform cross-sectional thickness, the pull wire lumen having a flattened oval cross-section and the pull wire having a flattened longitudinal profile.

In an aspect of the first embodiment, and in combination with any other aspects herein, the disclosure provides that the sidewall of the elongate tubular body has a non-uniform cross-sectional thickness such that the sidewall includes a thicker wall section and a thinner wall section that is diametrically opposed to the thicker wall section, the pull wire lumen extending within the thicker wall section of the sidewall and the thinner wall section of the sidewall including a fourth polymer having a fourth stiffness, the fourth stiffness being greater than the first stiffness.

In an aspect of the first embodiment, and in combination with any other aspects herein, the disclosure provides that the sidewall of the elongate tubular body has a substantially uniform cross-sectional thickness and a first balancing lumen is defined in the sidewall of the outer shaft, the first balancing lumen being diametrically opposed to the pull wire lumen. In an embodiment a first pull wire slidingly disposed through the pull wire lumen, wherein a distal end of the pull wire is coupled to the sidewall of the elongate tubular body and a proximal end of the pull wire is coupled to an actuator of the handle, and wherein the pull wire is operable to bend the elongate tubular body for steering the balloon catheter in situ; and a second pull wire is slidingly disposed through the first balancing lumen, wherein a distal end of the second pull wire is coupled to the sidewall of the elongate tubular body and a proximal end of the second pull wire is coupled to an actuator of the handle, and wherein the second pull wire is operable to bend the elongate tubular body for steering the balloon catheter in situ.

In an embodiment, a second balancing lumen is defined in the sidewall of the outer shaft, the second balancing lumen being offset by approximately ninety degrees from the pull wire lumen, and a third balancing lumen is defined in the sidewall of the outer shaft, wherein the third balancing lumen is diametrically opposed to the second balancing lumen. In an embodiment, a first pull wire is slidingly disposed through the pull wire lumen, wherein a distal end of the pull wire is coupled to the sidewall of the elongate tubular body and a proximal end of the pull wire is coupled to an actuator of the handle, and wherein the pull wire is operable to bend the elongate tubular body for steering the balloon catheter in situ; a second pull wire is slidingly disposed through the first balancing lumen, wherein a distal end of the second pull wire is coupled to the sidewall of the elongate tubular body and a proximal end of the second pull wire is coupled to an actuator of the handle, and wherein the second pull wire is operable to bend the elongate tubular body for steering the balloon catheter in situ; a third pull wire is slidingly disposed through the second balancing lumen, wherein a distal end of the third pull wire is coupled to the sidewall of the elongate tubular body and a proximal end of the third pull wire is coupled to an actuator of the handle, and wherein the third pull wire is operable to bend the elongate tubular body for steering the balloon catheter in situ; and a fourth pull wire is slidingly disposed through the third balancing lumen, wherein a distal end of the fourth pull wire is coupled to the sidewall of the elongate tubular body and a proximal end of the fourth pull wire is coupled to an actuator of the handle, and wherein the fourth pull wire is operable to bend the elongate tubular body for steering the balloon catheter in situ.

In an aspect of the first embodiment, and in combination with any other aspects herein, the disclosure provides that the handle includes a steering indicator that displays to the user an amount of bending of the elongate tubular body. In an embodiment, the steering indicator includes a transparent tube disposed over a slider rack and a longitudinal position of the slider rack with the transparent tube corresponds to the amount of bending of the elongate tubular body. In an embodiment, the transparent tube is disposed at a proximal end of the handle.

In an aspect of the first embodiment, and in combination with any other aspects herein, the disclosure provides the third portion of the tubular braid component extends distally beyond the distal end of the hypotube.

In an aspect of the first embodiment, and in combination with any other aspects herein, the disclosure provides the third portion of the tubular braid component has a distal end that longitudinally terminates distal to the distal end of the hypotube.

In an aspect of the first embodiment, and in combination with any other aspects herein, the disclosure provides the third polymer is disposed in and around the third portion of the tubular braid component and the length of the hypotube along the overlap segment of the distal portion. In an embodiment, the third polymer extends through voids of the pattern of the sidewall of the hypotube and voids of the tubular braid component.

In an aspect of the first embodiment, and in combination with any other aspects herein, the disclosure provides the first stiffness is constant along a length of the proximal portion and the second stiffness is constant along a length of the intermediate portion.

In an aspect of the first embodiment, and in combination with any other aspects herein, the disclosure provides the third stiffness varies along a length of the distal portion due to the pattern of the sidewall of the hypotube. In an embodiment, the pattern of the sidewall of the hypotube defines a plurality of successive windings having a void between each pair of adjacent successive windings. In an embodiment, the plurality of successive windings includes a first plurality of successive windings, a second plurality of successive windings, and a third plurality of successive windings, the second plurality of successive windings being disposed distal to the first plurality of successive windings and the third plurality of successive windings being disposed distal to the second plurality of successive windings, and each winding of the first plurality of successive windings has a first width, each winding of the second plurality of successive windings has a second width, and each winding of the third plurality of successive windings has a third width, the second width being greater than the third width and the first width being greater than the second width. In an embodiment, each void between each pair of adjacent successive windings is the same width.

In an aspect of the first embodiment, and in combination with any other aspects herein, the disclosure provides the elongated tubular body has a length from the proximal end to the distal end thereof and the proximal portion extends between 75-90% of the length of the elongated tubular body, the intermediate portion extends between 5-10% of the length of the elongated tubular body, and the distal portion extends between 5-15% of the length of the elongated tubular body.

In an aspect of the first embodiment, and in combination with any other aspects herein, the disclosure provides the elongated tubular body has a length from the proximal end to the distal end thereof and the distal portion extends between 8-10% of the length of the elongated tubular body.

In an aspect of the first embodiment, and in combination with any other aspects herein, the disclosure provides the tubular braid component is formed from a filament having a rectangular cross-section having a width between 0.004 inches and 0.020 inches.

In an aspect of the first embodiment, and in combination with any other aspects herein, the disclosure provides the elongated tubular body has a length from the proximal end to the distal end thereof and the elongated tubular body has an outer diameter that is constant along the length.

In an aspect of the first embodiment, and in combination with any other aspects herein, the disclosure provides the elongated tubular body has a first outer diameter that is constant along the proximal portion and a second outer diameter that is constant along the intermediate portion and the distal portion, the first outer diameter being greater than the second outer diameter.

In an aspect of the first embodiment, and in combination with any other aspects herein, the disclosure provides the outer shaft is operable to be rotated 360 degrees without kinking.

In an aspect of the first embodiment, and in combination with any other aspects herein, the disclosure provides the outer shaft exhibits a highly sensitive and functional response ratio for torque of the proximal portion compared to torque of the distal portion when the outer shaft is rotated 360 degrees.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 34 depicts a flow of a method for delivering the transcatheter valve prosthesis of FIG. 32 in accordance with an embodiment hereof.

DETAILED DESCRIPTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, “slidably” or “slidable” denotes back and forth movement in a longitudinal direction about a longitudinal axis LA of the handle (shown in FIG. 1) while “rotatably” or “rotatable” denotes movement or rotation about the longitudinal axis LA of the handle.

The following detailed description is merely exemplary in nature and is not intended to limit the invention or the application and uses of the invention. Although the description of the invention is in the context of delivery of a balloon-expandable prosthesis, the invention may also be used where it is deemed useful in endoscopic procedures, procedures in the coronary vessels, or procedures in the peripheral vessels. Furthermore, there is no intention to be bound by any expressed or implied theory presented in the preceding technical field, background, brief summary or the following detailed description.

Embodiments hereof relate to a delivery catheter or other delivery device having a shaft configured to transmit a torque from a proximal end of the delivery catheter to a distal end of the delivery catheter when the proximal end of the delivery catheter is rotated. Due to the construction of the outer shaft, rotation of a handle at the proximal end of the delivery catheter causes an entire length of the delivery catheter to rotate therewith, circumferentially to an exact degree, in order to better position a balloon-expandable prosthesis mounted at the distal end of the delivery catheter in situ.

Figure 29:
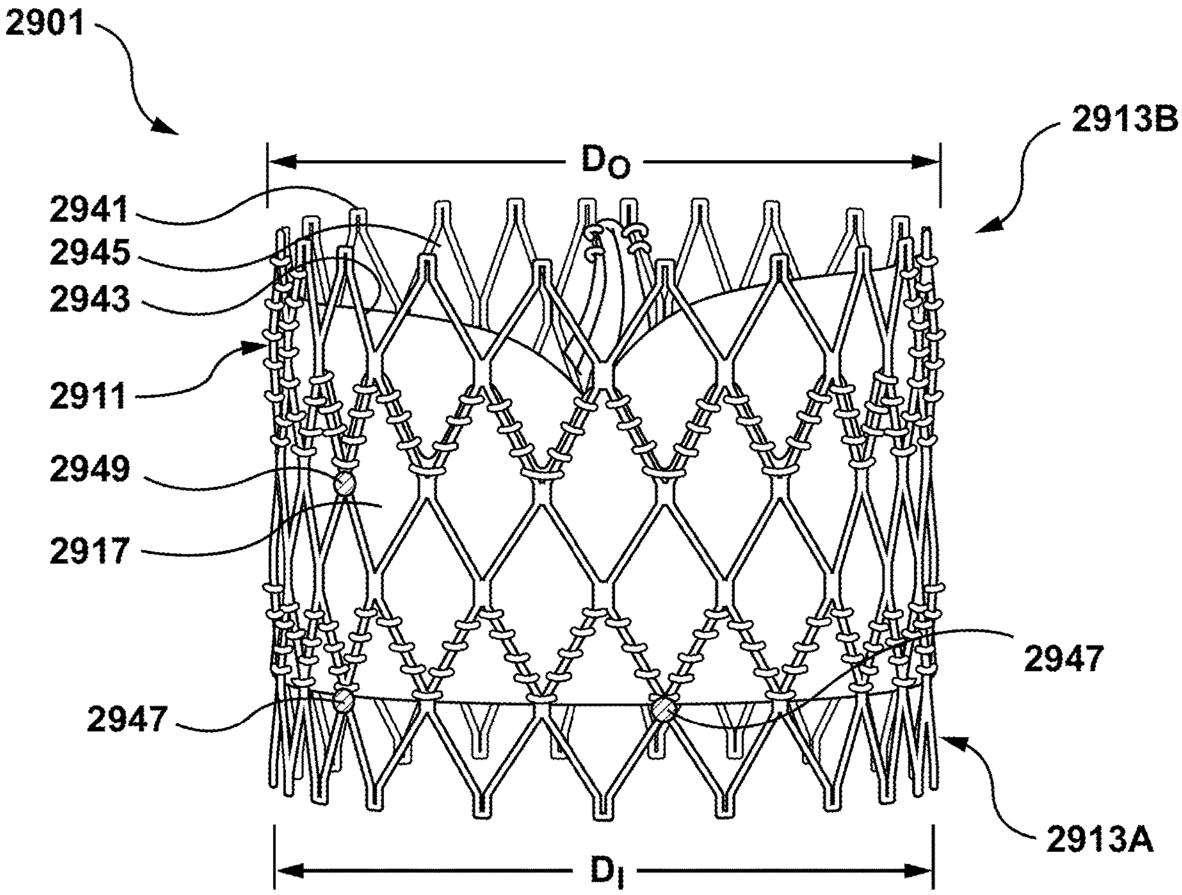
FIG. 29 is a side view of a transcatheter valve prosthesis that may be utilized as the balloon-expandable prosthesis of FIG. 1 in accordance with an embodiment hereof, wherein the transcatheter valve prosthesis is shown in its expanded configuration.
Figure 30:
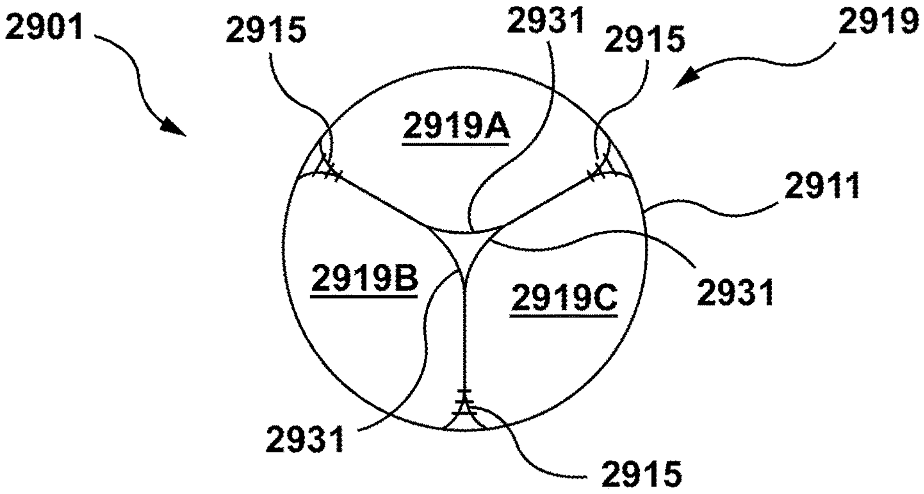
FIG. 30 is an end view of the transcatheter valve prosthesis of FIG. 29.

Turning now to the figures, a delivery system 100 includes a balloon catheter 102 having an inflatable balloon 110 and a balloon-expandable prosthesis 101 mounted on the balloon 110. The balloon catheter 102 has an outer shaft 112 that is configured for improved torque transmission as will be described in more detail herein. The balloon-expandable prosthesis 101 is shown in its delivery or unexpanded configuration in FIG. 1 and is shown in an expanded or deployed configuration in FIG. 2. As will be understood by those of ordinary skill in the art, the balloon-expandable prosthesis 101 is radially expanded or deployed by the balloon 110 and released from the balloon catheter 102 at a desired location in a patient’s body lumen. An exemplary balloon-expandable prosthesis, and the expanded or deployed configuration thereof, is best shown in FIGS. 29 and 30 described in more detail herein. However, the configuration of the balloon-expandable prosthesis 101 described herein is merely exemplary, and it would be apparent to one of ordinary skill in the art that the balloon catheter 102 may be utilized for delivering and deploying various types or configurations of prostheses. Further, although depicted as a delivery catheter for the balloon-expandable prosthesis 101, the balloon catheter 102 is not required to be configured for delivering a prosthesis but rather the balloon catheter 102 may be utilized in other procedures or for other purposes including diagnostic purposes. As will be described in more detail herein, the construction of the outer shaft 112 of the balloon catheter 102 is advantageous in any type of catheter that may require torqueing during navigation in situ. Although the balloon catheter 102 described herein is a stand-alone delivery catheter for delivering the balloon-expandable prosthesis 101, in another embodiment hereof (not shown), the balloon catheter 102 forms an outer tubular component of another type of treatment or delivery system.

The balloon catheter 102 includes a proximal portion 104 that extends out of the patient during clinical use and has a handle 106 which will be described in more detail herein with respect to FIGS. 15-18. As would be understood by one of ordinary skill in the art of balloon catheter design, the handle 106 includes a bifurcated luer 105 or other type of fitting that may be connected to a source of inflation fluid and may be of another construction or configuration without departing from the scope of the present invention. A distal portion 108 of the balloon catheter 102 is positionable at a target treatment location and includes the balloon 110, which is shown in an unexpanded configuration in FIG. 1 and is shown in an expanded or inflated configuration in FIG. 2. Stated another way, the balloon 110 is expandable from a first diameter shown in FIG. 1 to a second diameter shown in FIG. 2, the second diameter being greater than the first diameter. The balloon 110 may be made of a biocompatible material such as a thermoplastic polyurethane (TPU) resin, styrene-ethylene-butadiene-styrene (SEBS), PEBAX®, or other suitable polymeric material used for dilatation balloon manufacturing, and may have an outer diameter in the range of 2-4 mm and a length in the range of 5-15 mm. In an embodiment, the balloon 110 may have an expanded or inflated balloon diameter in the range of 20-50 mm and a length in the range of 10-50 mm when expanded or inflated.

Figure 1:
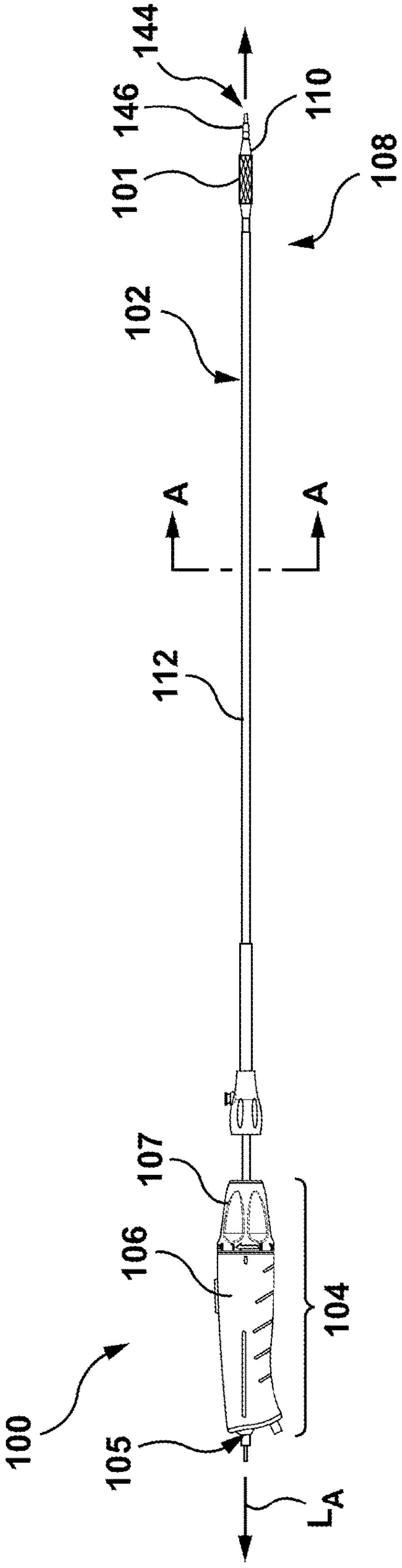
FIG. 1 is a side view of a delivery system according to an embodiment hereof, wherein the delivery system includes an outer shaft configured for improved torque transmission and the delivery system also includes a balloon-expandable prosthesis disposed at a distal portion thereof in its unexpanded configuration, and wherein the outer shaft includes a tubular braid component and a hypotube overlapping only a distal portion of the tubular braid component.
Figure 1A:
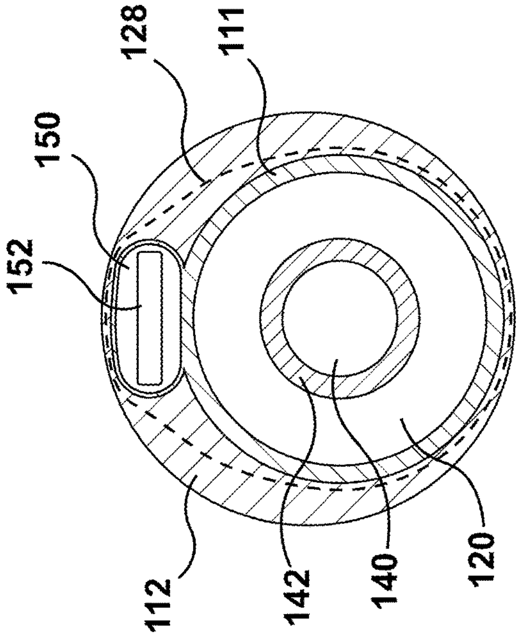
FIG. 1A is a cross-sectional view taken along line A-A of FIG. 1.
Figure 2:
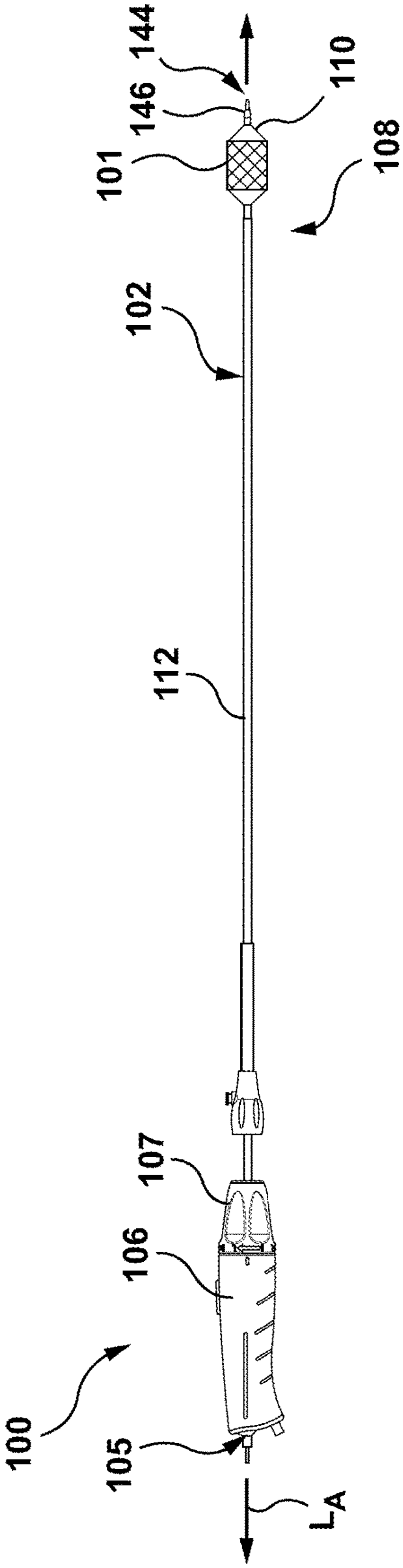
FIG. 2 is a side view of a delivery system according to an embodiment hereof, wherein the balloon-expandable prosthesis is shown in its expanded or inflated configuration.
Figures 6, 7A, 7B, 7C, 8A, 8B, 8C:
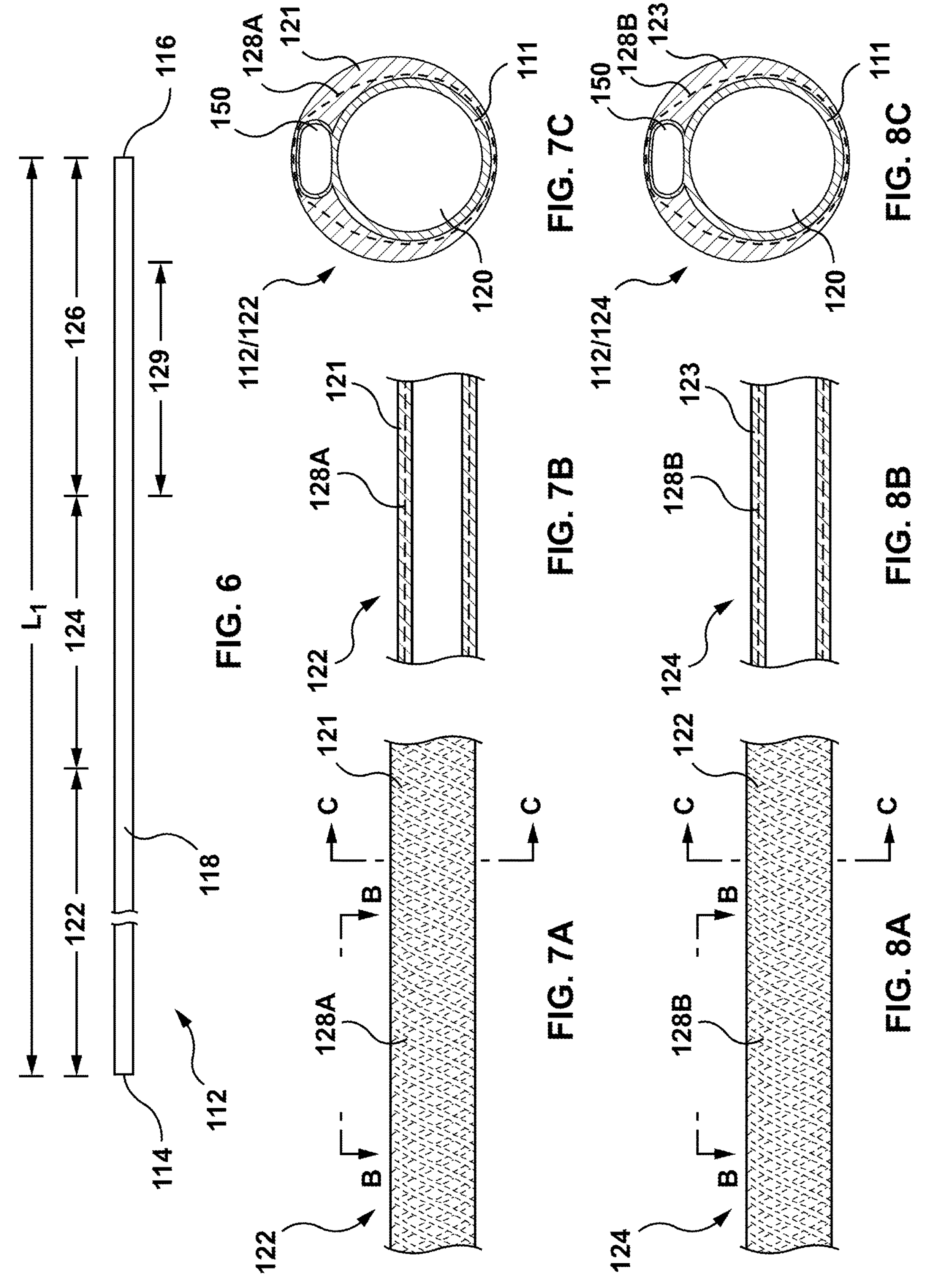
FIG. 6 is a side illustrative view of the outer shaft of the delivery system of FIG. 1, wherein the outer shaft is removed from the delivery system for sake of illustration only.
FIG. 7A is an enlarged side view of a proximal portion of the outer shaft of FIG. 6, wherein the proximal portion of the outer shaft includes the tubular braid component disposed within a first polymer.
FIG. 7B is a sectional view taken along like B-B of FIG. 7A.
FIG. 7C is a cross-sectional view taken along line C-C of FIG. 7A.
FIG. 8A is an enlarged side view of an intermediate portion of the outer shaft of FIG. 6, wherein the intermediate portion of the outer shaft includes a tubular braid component disposed within a second polymer.
FIG. 8B is a sectional view taken along like B-B of FIG. 8A.
FIG. 8C is a cross-sectional view taken along line C-C of FIG. 8A.

With reference to the FIG. 1A which is a cross-sectional view taken along line A-A of FIG. 1, the balloon catheter 102 may have an over-the-wire coaxial catheter configuration with the outer shaft 112 and an inner tubular component or inner shaft 142. With reference to FIG. 6, the outer shaft 112 has an elongate tubular body 118 extending from a proximal end 114 to a distal end 116 and defining a central lumen 120 therethrough. The proximal end 114 of the outer shaft 112 is coupled to the handle 106 and the distal end 116 of the outer shaft 112 is coupled to a proximal end of the balloon 110. The inner shaft 142 is disposed through the central lumen 120 of the elongate tubular body 118 of the outer shaft 112. The inner shaft 142 defines a guidewire lumen 140 extending substantially the entire length of the catheter for accommodating a guidewire (not shown) such that the balloon catheter 102 may be slidingly disposed and tracked over the guidewire. The inner shaft 142 has a proximal end (obscured from view in FIGS. 1 and 2) coupled to the handle 106 and a distal end 146 terminating distally of the balloon 110 and defining a distal guidewire port. Stated another way, the guidewire lumen 140 is open at the distal end 146 of the inner shaft 142. A distal tip 144 is attached to the distal end 146 of the inner shaft 142, and the distal tip 144 forms the distal end of the balloon catheter 102. The inner shaft 142 extends coaxially within the outer shaft 112 such that an annular inflation lumen is defined by the central lumen 120 extending between an inner surface of the outer shaft 112 and an outer surface of the inner shaft 142. The annular inflation lumen is in fluid communication with an interior of the balloon 110, and extends through the outer shaft 112 and into the inner volume of the balloon 110 to allow inflation fluid received through an inflation port of the bifurcated luer 105 of the handle 106 to be delivered to the balloon 110. A distal end of the balloon 110 is coupled to the inner shaft 142 at a position proximal to the distal end 146 of the inner shaft.

Other types of catheter construction are also amendable to the invention, such as, without limitation thereto, a catheter shaft formed by multi-lumen profile extrusion. For example, rather than including coaxial inner and outer catheter shafts, the balloon catheter may include a single catheter shaft that defines an inflation lumen and a guidewire lumen, each extending substantially the entire length of the catheter and parallel to each other. Stated another way, the inflation and guidewire lumens may be defined or preformed in a sidewall of a single catheter shaft. In yet another embodiment, the inflation lumen may alternatively be formed via an elongated inflation tube disposed within and attached to the outer shaft 112, as will be understood by those of ordinary skill in the art of balloon catheter construction. In addition, the balloon catheter 102 may have a rapid-exchange configuration with the guidewire lumen extending only along a distal portion of the catheter, as understood by those of ordinary skill in the art.

In addition to the guidewire lumen 140 and the annular inflation lumen defined by the central lumen 120, the balloon catheter 102 further includes a pull wire lumen 150. The pull wire lumen 150 is defined or preformed in a sidewall of the outer shaft 112. As shown in FIG. 1A, the outer shaft 112 has a non-uniform cross-sectional thickness to provide a thicker wall section for the pull wire lumen 150 which is sized and dimensioned to receive the pull wire 152. The pull wire lumen 150 extends adjacent or parallel to the guidewire lumen 140 and the annular inflation lumen defined by the central lumen 120, and terminates proximal to the distal end 116 of the elongated tubular body 118 of the outer shaft 112. The pull wire lumen 150 is configured to accommodate a pull wire 152 for steering the balloon catheter 102. The pull wire 152 is operable to bend the elongate tubular body 118 of the outer shaft 112 for steering the balloon catheter 102 in situ and may be selectively tensioned via the user. More particularly, the pull wire 152 is slidably disposed within the pull wire lumen 152 such that it may be selectively tensioned by the user to bend the distal portion 108 of the balloon catheter 102. As used herein, “slidably” denotes back and forth movement in a longitudinal direction along or generally parallel to a central longitudinal axis LA of the delivery device 100. While the pull wire 152 is primarily housed or disposed within the pull wire lumen 150 of the outer shaft 112, the proximal end thereof (not shown) proximally extends beyond the proximal end 114 of the outer shaft 112 and is accessible via the handle 106 to be pulled or pushed which results in controlled bending movement of the distal portion 108 of the balloon catheter 102.

More particularly, the proximal end of the pull wire 152 is coupled to an actuator 107 of the handle 106 and a distal end (not shown) of the pull wire 152 is attached to the sidewall of the elongate tubular body 118 of the outer shaft 112, adjacent to the distal end 116 of the outer shaft 112. The pull wire 152 is thus accessible to a user via the actuator 107 of the handle 106 and the curvature of the distal portion 108 of the balloon catheter 102 can be changed based on the user manipulating the pull wire 152 via the actuator 107 of the handle 1906. In the embodiment depicted in FIG. 1, the actuator 107 is a knob that is rotatable relative to the housing of the handle 106. When the knob is rotated in a first direction (i.e., one of clockwise or counter-clockwise), the pull wire 152 is retracted and placed under tension to bend or deflect the distal portion 108 of the balloon catheter 102. Stated another way, when the pull wire 152 is retracted via actuation of the actuator 107, the pull wire 152 is placed under tension and bends the distal portion 108 of the balloon catheter 102. When the knob is rotated in a second direction opposite from the first direction (i.e., the other of clockwise or counter-clockwise), tension on the pull wire 152 is released and the distal portion 108 of the balloon catheter 102 resumes its straightened configuration.

Figure 3:
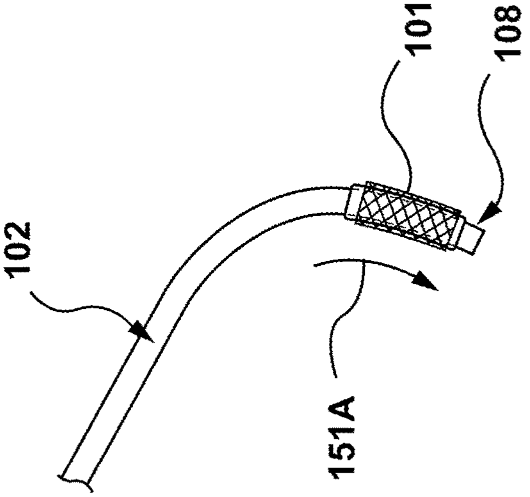
FIG. 3 is a side view of the distal portion of the delivery system of FIG. 1, wherein the distal portion is bent in a first direction via a steering mechanism of the delivery system.

For example, FIG. 3 is a side view of the distal portion 108 of the balloon catheter 102 that illustrates the distal portion 108 of the balloon catheter 102 bent in a first direction via activation of the pull wire 152 as illustrated by directional arrow 151A. If it is desired to bend or deflect the distal portion 108 of the balloon catheter 102 in an opposing direction (i.e., a second direction opposite from the first direction as illustrated by directional arrow 151B in FIG. 4), the balloon catheter 102 may be torqued or rotated approximately 180 degrees and then the pull wire 152 may be actuated to bend the distal portion 108 of the balloon catheter 102. The dimension of the radius of curvature depends upon the intended application of the balloon catheter 102, the target anatomy for use of the balloon catheter 102, and/or the size or profile of the balloon catheter 102. In an embodiment in which the balloon catheter 102 is utilized in a transcatheter aortic valve implantation (TAVI) procedure, the radius of curvature ranges between twenty (20) millimeters and sixty (60) millimeters. In another embodiment hereof in which the balloon catheter 102 is utilized in neurological applications, the radius of curvature may be as small as 0.5 centimeters.

As stated above, when steering the balloon catheter 102 in situ, it may be necessary to torque or rotate the balloon catheter 102 in order to bend or deflect the distal portion 108 of the balloon catheter 102 in an opposing or different direction. In an embodiment hereof, the balloon catheter 102 is torqued via rotation of the handle 106.

In embodiments hereof, the pull wire lumen 150 has an oblong or generally rectangular cross-section in order to accommodate the pull wire 152, which may have a flat or flattened longitudinal profile as shown in FIG. 1A. While other shapes are also acceptable, the flattened construction of the pull wire 152 provides more mass and thus an enhanced steerability. In another embodiment depicted in FIG. 1G, a pull wire 152G has a braided construction which is configured to reduce axial bias that may be produced by the non-uniform cross-sectional thickness of the elongate tubular body 118. As described in more detail herein with respect to FIGS. 1B-1F, uneven or non-uniform cross-sectional thickness of a catheter shaft may produce an axial bias of the elongate tubular body 118 of the outer shaft 112, meaning that the elongate tubular body 118 may have a preferential axis when in a curved configuration in situ. The pull wire 152G formed from a plurality of braided or woven filaments reduces the axial bias of the elongate tubular body 118 of the outer shaft 112. In another embodiment (not shown), a pull wire lumen as well as a pull wire disposed therethrough may have different configurations or shapes including oval or circular. The pull wire 152 is preferably formed from aramid fibre, carbon, or another relatively hard polymeric material. However, in another embodiment hereof, the pull wire 152 may be formed from Nitinol or stainless steel.

Figure 5:
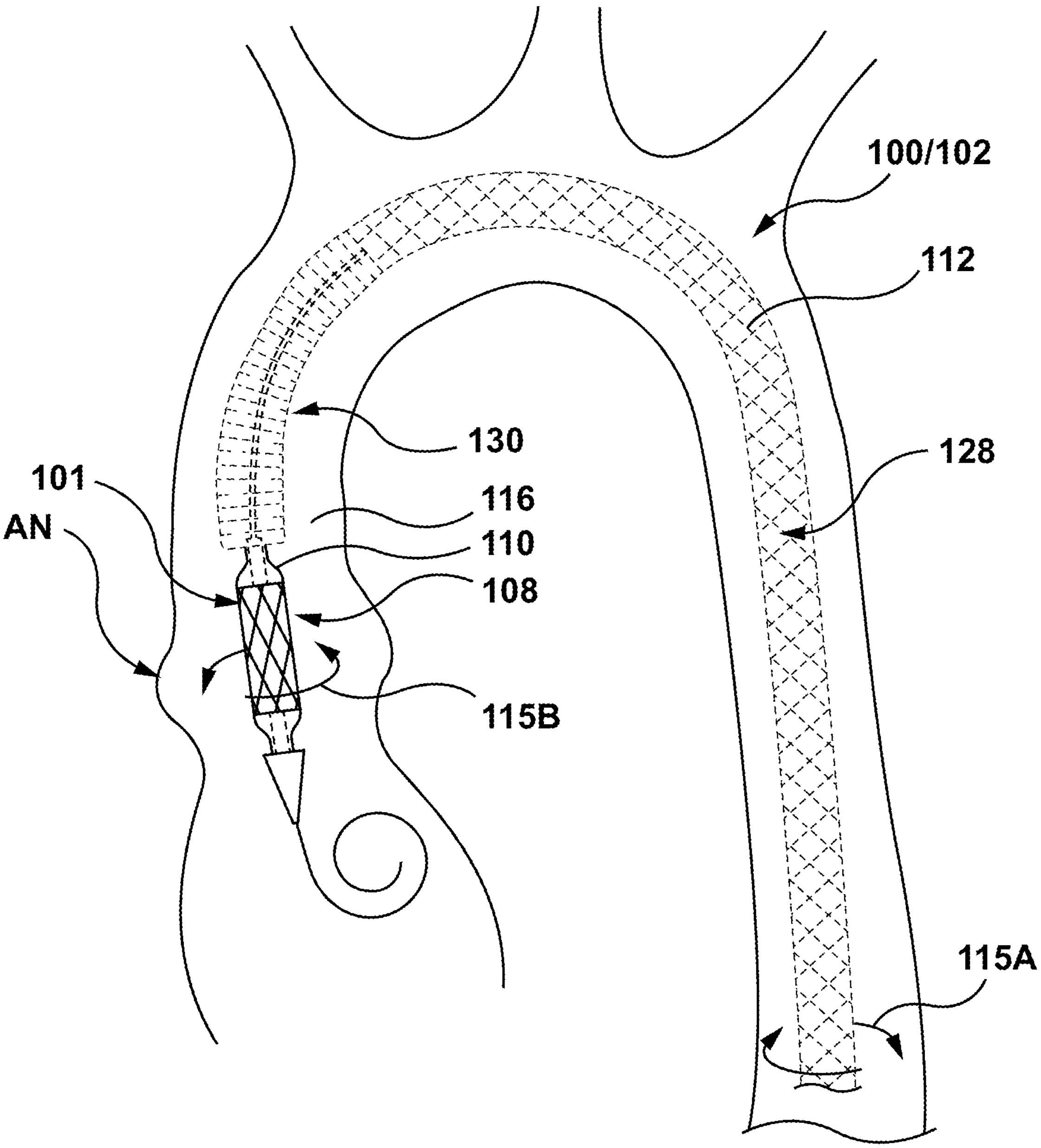
FIG. 5 is a sectional view of the delivery system of FIG. 1 being delivered in situ to a treatment site.

As shown in FIG. 5, when positioned in situ, steering and torqueing of the delivery system 100 is of utmost importance in order to properly position the balloon-expandable prosthesis 101 within a native annulus AN prior to deployment of the balloon-expandable prosthesis 101. Steering of the delivery system 100 is accomplished via manipulation of the pull wire 152 as described above, and permits the user to navigate the delivery system 100 through curved anatomy such as the aortic arch as shown in FIG. 5. Further, steering of the delivery system 100 assists the user in properly aligning the balloon-expandable prosthesis 101 within the target site, i.e., the native annulus AN. For example, the balloon-expandable prosthesis 101 needs to be properly aligned, axially and annularly/circumferentially, so that the balloon-expandable prosthesis 101 properly engages the native leaflets/tissue of the target site, e.g., the aortic annulus, without causing conduction blockages by implanting too deep or causing an embolization of the balloon-expandable prosthesis 101 because it was implanted too high. Torqueing the delivery system 100 is accomplished via rotation of the handle 106, and permits the user to circumferentially align the balloon-expandable prosthesis 101 within the target site, e.g., the native annulus AN, in situ. When being positioned in situ, it is very important to avoid blocking the ostia of the right coronary artery and/or the left main coronary artery. Proper circumferential or rotational orientation within the target site reduces the risk of blocking coronary access. In addition, it may be desired to rotationally align commissures of the balloon-expandable prosthesis 101 with the native valve commissures. Commissure to commissure alignment (prosthesis commissure to native commissure) may improve hemodynamics and leaflet durability of the balloon-expandable prosthesis 101. To circumferentially align the balloon-expandable prosthesis 101, the balloon-expandable prosthesis 101 can rotated in situ by the delivery system 100 to be positioned in a desired circumferential or rotational alignment.

Turning back to FIG. 1A, the outer shaft 112 may include an innermost layer 111 that extends the entire length thereof. In an embodiment, the innermost layer 111 is a liner formed from PEBAX® 55D. Apart from the innermost layer 111, the outer shaft 112 is formed from a polymeric material and includes a tubular braid component 128 embedded within the polymeric material. The tubular braid component 128 will be described in more detail herein. Further, the polymeric material of the outer shaft 112 (apart from the innermost layer 111) varies along a length thereof as will also be described in more detail herein.

As previously stated, as shown in FIG. 1A, the outer shaft 112 has a non-uniform cross-sectional thickness to provide a thicker wall section for the pull wire lumen 150 which is sized and dimensioned to receive the pull wire 152. Stated another way, the sidewall of the elongate tubular body 118 has a non-uniform cross-sectional thickness, with the pull wire lumen 150 extending within a thicker wall section of the sidewall. More particularly, the elongate tubular body 118 has a thickness T2 adjacent to the pull wire lumen 150 and a thickness T1 diametrically opposed to the thickness T2. Thickness T1 is less than thickness T2, such that thickness T1 is between 30-70% of thickness T2. The sidewall of the elongate tubular body 118 thus includes a thicker wall section (i.e., thickness T2) and a thinner wall section (i.e., thickness T1) that is diametrically opposed to the thicker wall section, with the pull wire lumen 150 extending within the thicker wall section of the sidewall. However, other embodiments of the outer shaft are depicted in FIGS. 1B-1F. The embodiments of FIGS. 1B-1F are configured to address the axial bias that may be produced by the non-uniform cross-sectional thickness of the outer shaft 112 as shown in FIG. 1A. Uneven or non-uniform cross-sectional thickness of a catheter shaft may result in an uneven or non-uniform flexibility thereof. More particularly, the non-uniform cross-sectional thickness of FIG. 1A may produce an axial bias of the elongate tubular body 118 of the outer shaft 112, meaning that the elongate tubular body 118 may have a preferential axis when in a curved configuration in situ. If the balloon catheter 102 is rotated beyond 180 degrees when in a curved configuration in situ, the elongate tubular body 118 may have the tendency to return to the axis of least resistance due to the axial bias thereof. Axial bias is therefore problematic during use of a catheter in situ when twisting the catheter around a bend in the vessel. Resistance to the twisting motion is encountered by the stiffer portions of the catheter which subsequently whip around the bend when sufficient twisting is applied. Such irregular movements are undesirable when positioning a catheter in situ. The embodiments of FIGS. 1B-1F reduce the axial bias of the elongate tubular body 118 of the outer shaft 112.

Figure 1B:
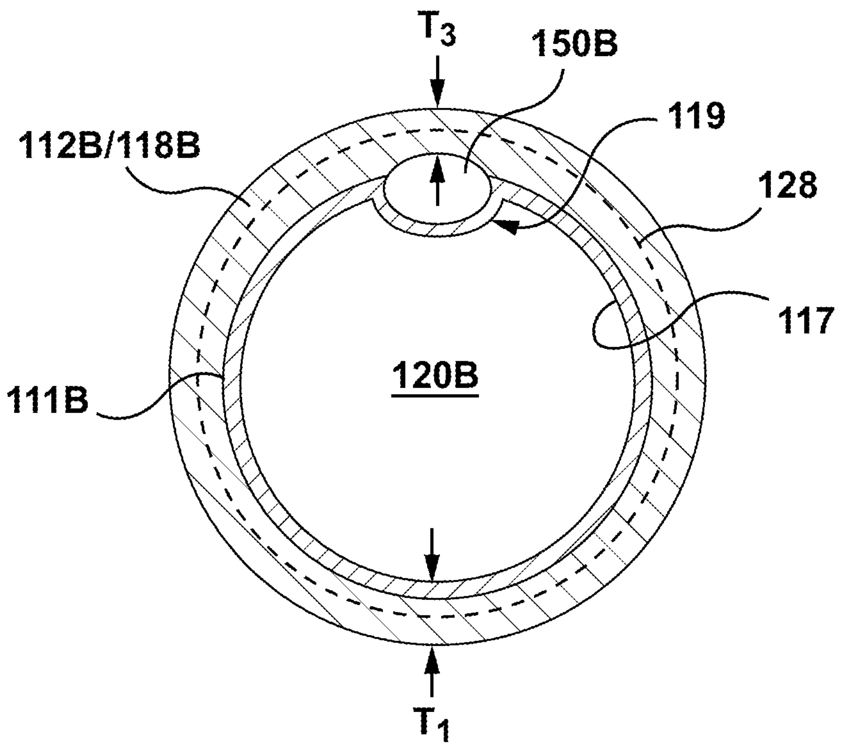
FIG. 1B is a cross-sectional view taken along line A-A of FIG. 1 according to an alternative embodiment hereof, wherein a pull wire lumen is offset or off-centered within the polymeric material of the outer shaft.

In the embodiment of FIG. 1B, an outer shaft 112B having an elongate tubular body 118B may include an innermost layer 111B that is similar to the innermost layer 111. Further, similar to the outer shaft 112, the outer shaft 112B defines a central lumen 120B, is formed from a polymeric material that varies along a length thereof as will also be described in more detail herein and includes the tubular braid component 128 embedded within the polymeric material, which will also be described in more detail herein. A pull wire lumen 150B is formed within the elongate tubular body 118B as an elongated radial protrusion 119 that axially extends along an inner surface 117 of the elongate tubular body 118B and radially extends or protrudes into the central lumen 120B of the elongate tubular body 118B. The elongated radial protrusion 119 extends in an axial direction for an entire length or substantially the entire length of the elongate tubular body 118B. By moving the pull wire lumen 150B toward the central lumen 120B of the elongate tubular body 118B, the axial bending stiffness of the elongate tubular body 118B is more balanced and the axial bias of the outer shaft 112B is reduced relative to the outer shaft 112. The axial bending stiffness of the elongate tubular body 118B is more balanced because the amount of polymeric material around a circumference of the elongate tubular body 118B is more uniform compared to the amount of polymeric material around a circumference of the elongate tubular body 118. More particularly, rather than the pull wire lumen 150 being centered within the polymeric material of the elongate tubular body 118, the pull wire lumen 150B is offset or off-centered within the polymeric material of the elongate tubular body 118B such that the pull wire lumen 150B is disposed closer to the central lumen 120B of the elongate tubular body 118B than the outer surface of the elongate tubular body 118B. Radially above the pull wire lumen 150B, the polymeric material has a thickness T3 while the elongate tubular body 118B has a thickness T1 diametrically opposed to the thickness T3. Thickness T3 is equal to or substantially similar to thickness T1, such that thickness T3 is between 75-100% of thickness T1. Since thicknesses T1 and T3 are substantially similar, the axial bending stiffness of the elongate tubular body 118B is more balanced and the axial bias of the outer shaft 112B is reduced relative to the outer shaft 112.

Figure 1C:
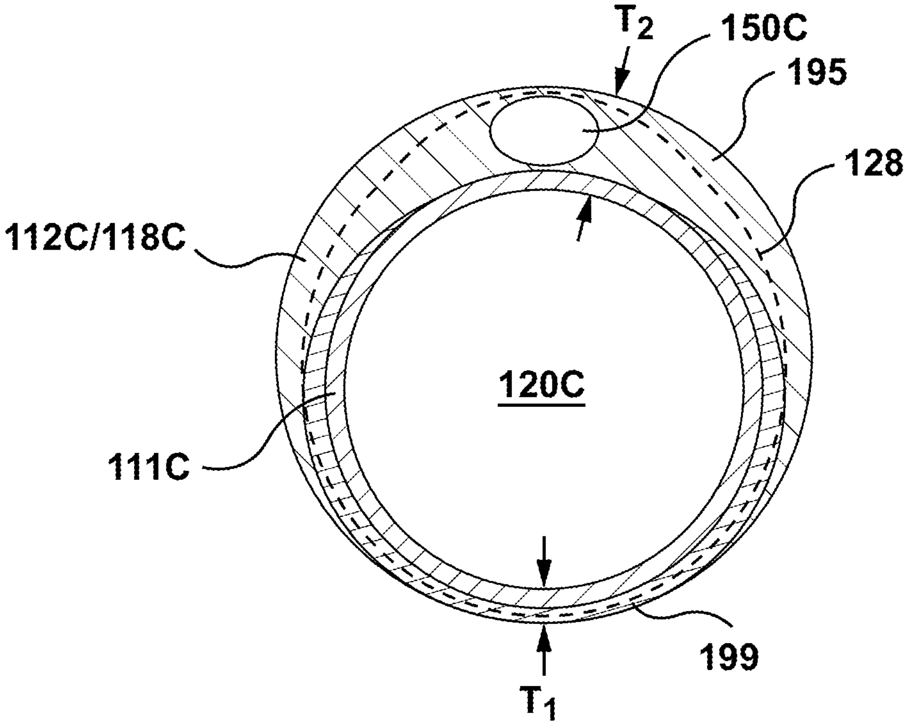
FIG. 1C is a cross-sectional view taken along line A-A of FIG. 1 according to an alternative embodiment hereof, wherein the outer shaft is formed with a stiffer material diametrically opposed to a pull wire lumen.

In the embodiment of FIG. 1C, an outer shaft 112C having an elongate tubular body 118C may include an innermost layer 111C that is similar to the innermost layer 111. Further, similar to the outer shaft 112, the outer shaft 112C defines a central lumen 120C, is formed from a polymeric material that varies along a length thereof as will also be described in more detail herein and includes the tubular braid component 128 embedded within the polymeric material, which will also be described in more detail herein. The outer shaft 112C has a non-uniform cross-sectional thickness to provide a thicker wall section for a pull wire lumen 150C which is sized and dimensioned to receive a pull wire (not shown). Stated another way, the sidewall of the elongate tubular body 118C has a non-uniform cross-sectional thickness, with the pull wire lumen 150C extending within a thicker wall section of the sidewall. More particularly, the elongate tubular body 118C has a thickness T2 adjacent to the pull wire lumen 150C and a thickness T1 diametrically opposed to the thickness T2. Thickness T1 is less than thickness T2, such that thickness T1 is between 30-70% of thickness T2. The sidewall of the elongate tubular body 118C thus includes a thicker wall section (i.e., thickness T2) and a thinner wall section (i.e., thickness T1) that is diametrically opposed to the thicker wall section, with the pull wire lumen 150C extending within the thicker wall section of the sidewall. However, in this embodiment, the elongate tubular body 118C is formed by first and second axial segments 195, 199 that are formed from different polymeric materials and are diametrically opposed to each other around the circumference of the elongate tubular body 118C. Each of the first and second axial segments 195, 199 extends in an axial direction for an entire length or substantially the entire length of the elongate tubular body 118C. The polymer of the second axial segment 199 has a higher modulus than the polymer of the first axial segment 195. Stated another way, the polymer of the second axial segment 199 is stiffer than the polymer of the first axial segment 195. By forming the elongate tubular body 118C with a stiffer material diametrically opposed to the pull wire lumen 150C, the axial bending stiffness of the elongate tubular body 118C is more balanced and the axial bias of the outer shaft 112C is reduced relative to the outer shaft 112. The axial bias is reduced because even though the second axial segment 199 is thinner than the first axial segment 195, the second axial segment 199 is formed from a stiffer material than the first axial segment 195. The polymer of the first axial segment 195 varies along a length thereof, i.e., the stiffness thereof varies along proximal, intermediate, and distal sections of the elongate tubular body, as will be described in more detail herein with respect to FIGS. 6-9C. The polymer of the second axial segment 199 is consistent or uniform along a length thereof and forms the thinner wall section of the sidewall. The first axial segment 195 may include first, second, and third polymers along the proximal, intermediate, and distal sections of the elongate tubular body as will be described in more detail herein with respect to FIGS. 6-9C, and accordingly the polymer of the second axial segment 199 may be considered a fourth polymer of the elongate tubular body 118C. The fourth polymer of the second axial segment 199 is stiffer than each of the first, second, and third polymers of the first axial segment 195.

The second axial segment 199 extends only partially around the circumference of the elongate tubular body 118C with the second axial segment 199 being diametrically opposed to the pull wire lumen 150C. In an embodiment, the second axial segment 199 extends around between 60-80% of the circumference of the elongate tubular body 118C. The thickness of the second axial segment 199 varies such that the thickest portion thereof (thickness T1) is diametrically opposed to the pull wire lumen 150C, and the thickness of the second axial segment 199 decreases or gradually tapers as it circumferentially extends away from the thickest portion thereof. As the thickness of the second axial segment 199 decreases or gradually tapers, the first axial segment 195 overlaps or overlays the second axial segment 199 to form a smooth transition between the first and second axial segments 195, 199.

The first axial segment 195 also extends only partially around the circumference of the elongate tubular body 118C with the pull wire lumen 150C being formed in the thickest portion (thickness T2) of the first axial segment 195. In an embodiment, the first axial segment 195 extends around between 60-80% of the circumference of the elongate tubular body 118C. The thickness of the first axial segment 195 varies such that the thickness of the first axial segment 195 decreases or gradually tapers as it circumferentially extends away from the thickest portion thereof. As the thickness of the first axial segment 195 decreases or gradually tapers, the first axial segment 195 overlaps or overlays the second axial segment 199 to form a smooth transition between the first and second axial segments 195, 199.

As stated above, the polymer of the second axial segment 199 has a higher modulus than the polymer of the first axial segment 195. Exemplary materials for the polymers of the first axial segment 195 and the second axial segment 199 include thermoplastic elastomers of varying durometers. For example, the second axial segment 199 may be PEBAX 72D while the first axial segment 195 may be PEBAX 63D which has a softer durometer than PEBAX 72D.

Alternatively, thermoplastic elastomers such as PEBAX may be used as the polymer of the first axial segment 195 in combination with nylon (AESNO or VESTAMID) as the polymer of the second axial segment 199. A similar configuration may be achieved with polyethylenes of different molecular weights.

Figure 1D:
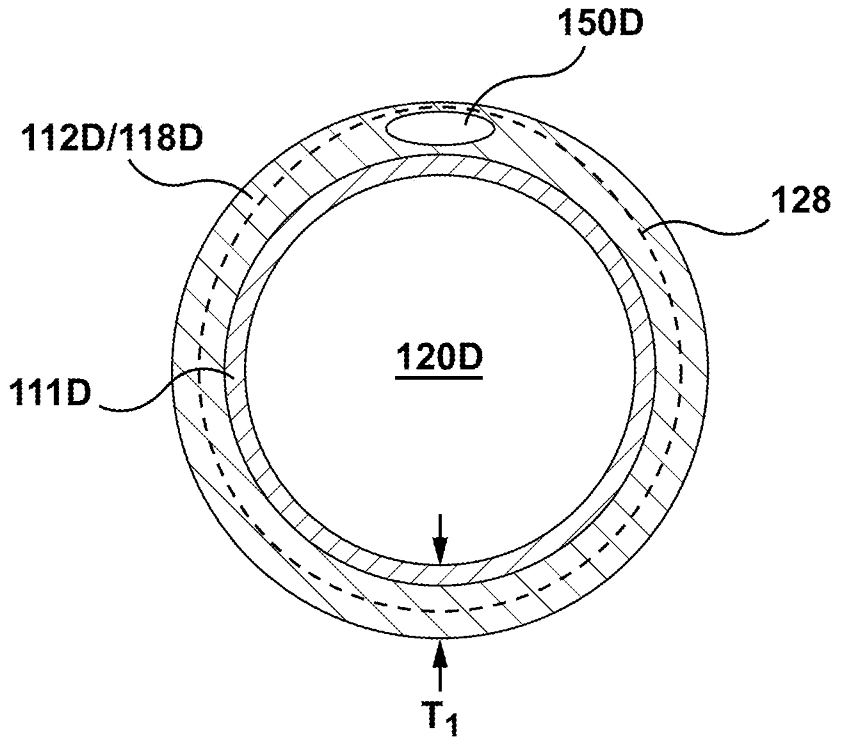
FIG. 1D is a cross-sectional view taken along line A-A of FIG. 1 according to an alternative embodiment hereof, wherein the outer shaft has a uniform thickness with a pull wire lumen having a flattened oval configuration.

In the embodiment of FIG. 1D, an outer shaft 112D having an elongate tubular body 118D may include an innermost layer 111D that is similar to the innermost layer 111. Further, similar to the outer shaft 112, the outer shaft 112D defines a central lumen 120D, is formed from a polymeric material that varies along a length thereof as will also be described in more detail herein and includes the tubular braid component 128 embedded within the polymeric material, which will also be described in more detail herein. The sidewall of the elongate tubular body 118D has a uniform cross-sectional thickness and a pull wire lumen 150D has an oblong or flattened oval configuration that is particularly configured to receive a flat pull wire (not shown). Although not shown with a pull wire, the pull wire may have a flat or flattened profile such as pull wire 152 shown in FIG. 1A. Forming the pull wire lumen 150D as a flattened oval enables the elongate tubular body 118D to have a uniform wall thickness, thereby reducing the axial bias of the outer shaft 112B relative to the outer shaft 112. The elongate tubular body 118D has a uniform thickness T1 around the entire circumference thereof.

Figure 1E:
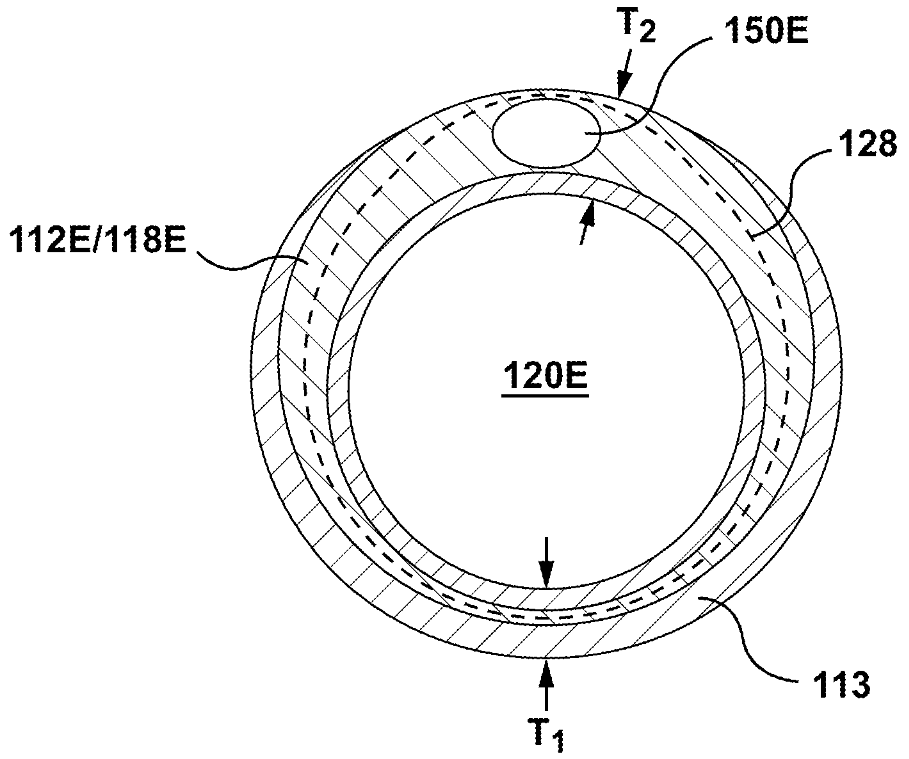
FIG. 1E is a cross-sectional view taken along line A-A of FIG. 1 according to an alternative embodiment hereof, wherein the outer shaft has a uniform thickness due to a jacket added thereto.

In the embodiment of FIG. 1E, an outer shaft 112E having an elongate tubular body 118E may include an innermost layer 111E that is similar to the innermost layer 111. Further, similar to the outer shaft 112, the outer shaft 112E defines a central lumen 120E, is formed from a polymeric material that varies along a length thereof as will also be described in more detail herein and includes the tubular braid component 128 embedded within the polymeric material, which will also be described in more detail herein. The sidewall of the elongate tubular body 118E has a substantially uniform cross-sectional thickness and a pull wire lumen 150E is formed in the sidewall of the elongate tubular body. More particularly, the elongate tubular body 118E has a thickness T2 adjacent to the pull wire lumen 150E and a thickness T1 diametrically opposed to the thickness T2. Thickness T1 is equal to or substantially similar to thickness T2, such that thickness T1 is between 75-100% of thickness T2. The elongate tubular body 118E is initially formed as the elongate tubular body 118, and a jacket 113 of the polymer material thereof is added locally during a secondary fuse step to result in thickness T1 being equal to or substantially similar to thickness T2. Jacket 113 extends only partially over the circumferential surface, with the jacket 113 being diametrically opposed to the pull wire lumen 150E. The thickness of the jacket 113 varies such that the thickest portion thereof is diametrically opposed to the pull wire lumen 150E, and the thickness of the jacket 113 decreases or gradually tapers as it circumferentially extends away from the thickest portion thereof to form a smooth transition between the jacket 113 and the elongate tubular body 118 as initially formed.

Figure 1F:
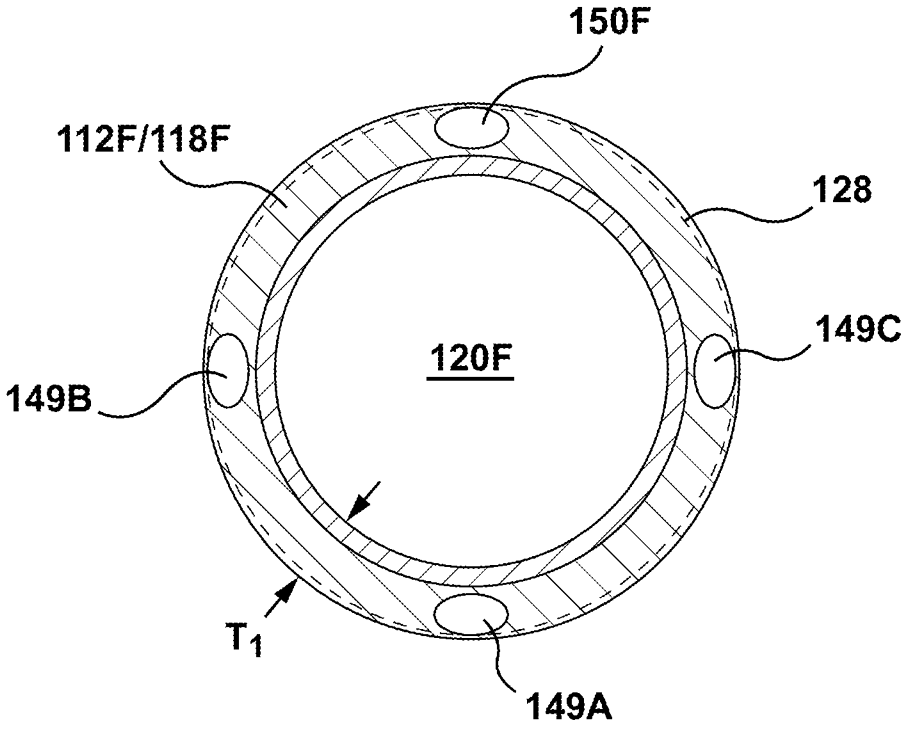
FIG. 1F is a cross-sectional view taken along line A-A of FIG. 1 according to an alternative embodiment hereof, wherein the outer shaft includes a pull wire lumen formed therein in addition to first, second, and third balancing lumens formed therein.
Figure 1G:
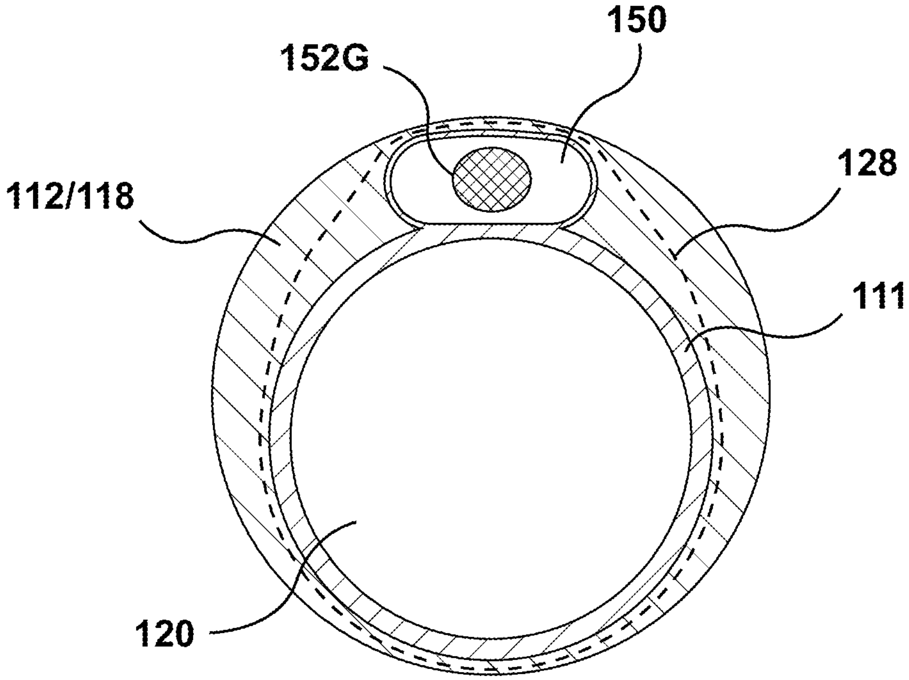
FIG. 1G is a cross-sectional view taken along line A-A of FIG. 1 according to an alternative embodiment hereof, wherein a pull wire disposed in a pull wire lumen of the outer shaft has a braided configuration.

In the embodiment of FIG. 1F, an outer shaft 112F having an elongate tubular body 118F may include an innermost layer 111F that is similar to the innermost layer 111. Further, similar to the outer shaft 112, the outer shaft 112F defines a central lumen 120F, is formed from a polymeric material that varies along a length thereof as will also be described in more detail herein and includes the tubular braid component 128 embedded within the polymeric material, which will also be described in more detail herein. The sidewall of the elongate tubular body 118F has a uniform cross-sectional thickness and a pull wire lumen 150F is formed in the sidewall of the elongate tubular body 118F. The elongate tubular body 118F has a uniform thickness T1 around the entire circumference thereof. A first balancing lumen 149A is also defined in the sidewall of the elongate tubular body 118F, and the first balancing lumen 149A is diametrically opposed to the pull wire lumen 150F. The first balancing lumen 149A is of the same size and shape as the pull wire lumen 150F. In an embodiment, a first pull wire (i.e., pull wire 152) is slidingly disposed through the pull wire lumen 150F, and a second pull wire (not shown) is slidingly disposed through the first balancing lumen 149A. Each of the first and second pull wires include a distal end coupled to the sidewall of the elongate tubular body 118F and is operable to bend the elongate tubular body 118F for steering the balloon catheter 102 in situ as described above with respect to the pull wire 152. In another embodiment, a pull wire (i.e., pull wire 152) is slidingly disposed through the pull wire lumen 150F and the first balancing lumen 149A is empty, i.e., does not include a pull wire slidingly disposed therethrough. Regardless of whether a pull wire is disposed through the first balancing lumen 149A, the first balancing lumen 149A is provided through the elongate tubular body 118F such that the axial bending stiffness of the elongate tubular body 118F is more balanced and the axial bias of the outer shaft 112F is reduced relative to the outer shaft 112.

Although not required, as shown in FIG. 1F, a second balancing lumen 149B is also defined in the sidewall of the elongate tubular body 118F and the second balancing lumen 149B is offset by approximately ninety degrees from the pull wire lumen 150F. The second balancing lumen 149B is of the same size and shape as the pull wire lumen 150F. A third balancing lumen 149C is also defined in the sidewall of the elongate tubular body 118F and the third balancing lumen 149C is diametrically opposed to the second balancing lumen 149B. The third balancing lumen 149B is also of the same size and shape as the pull wire lumen 150F. In an embodiment, a third pull wire (not shown) is slidingly disposed through the second balancing lumen 149B, and a fourth pull wire (not shown) is slidingly disposed through the third balancing lumen 149C. Each of the third and fourth pull wires include a distal end coupled to the sidewall of the elongate tubular body 118F and is operable to bend the elongate tubular body 118F for steering the balloon catheter 102 in situ as described above with respect to the pull wire 152. The third and fourth pull wires add additional planes of steering to the balloon catheter. In another embodiment, the second and third balancing lumens 149B, 149C are empty, i.e., do not include a pull wire slidingly disposed therethrough. Regardless of whether a pull wire is disposed through the second and third balancing lumens 149B, 149C, the second and third balancing lumens 149B, 149C are provided through the elongate tubular body 118F such that the axial bending stiffness of the elongate tubular body 118F is more balanced and the axial bias of the outer shaft 112F is reduced relative to the outer shaft 112. Additional balancing lumens may be incorporated into the elongate tubular body 118F as long as each balancing lumen is diametrically opposed from another balancing lumen, and all of the balancing lumens are spaced at equal intervals around a circumference of the elongate tubular body 118F.

Each balancing lumen need only provide a corresponding resistance to bending as the diametrically opposed lumen. Thus, it is not required that pairs of diametrically opposed balancing lumens have the exact same shape or configuration. In an embodiment, one or more of the balancing lumens are filled with a core or strip of softer material that is configured to provide a corresponding resistance to bending as a respective diametrically opposed balancing lumen. Stated another way, rather than reproducing a corresponding balancing lumen with the same shape and materials of a diametrically opposed balancing lumen, the same result may be achieved with a balancing lumen having a different shape and/or material.

Although the alternative embodiments of FIGS. 1B-1G are incorporated into an outer shaft in which the stiffness varies along a length thereof, i.e., the stiffness thereof varies along proximal, intermediate, and distal sections of the elongate tubular body as described in more detail herein with respect to FIGS. 6-9C, it will be understood by one of ordinary skill in the art that these embodiments may be incorporated into a catheter shaft in which the stiffness does not vary along a length thereof in order to reduce axial bias thereof. Stated another way, the embodiments of FIGS. 1B-1G may be incorporated into any catheter shaft having a lumen formed in a sidewall thereof, i.e. a pull wire lumen, that may have a preferential axis when in a curved configuration and may have the tendency to return to the axis of least resistance due to the axial bias thereof when rotated in situ.

Figure 4:
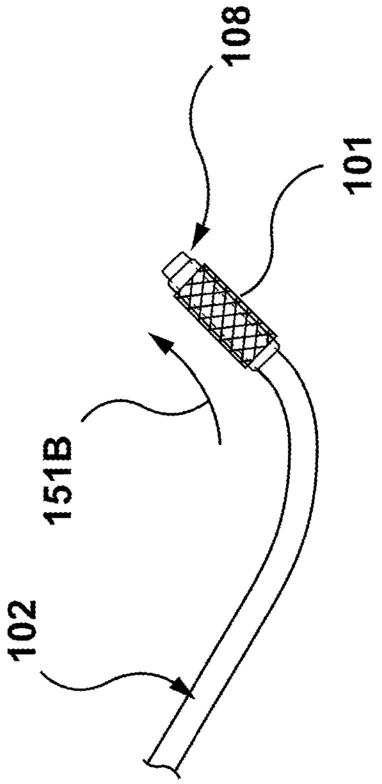
FIG. 4 is a side view of the distal portion of the delivery system of FIG. 1, wherein the distal portion is bent in a second or opposing direction via the steering mechanism of the delivery system.

The configuration of the outer shaft 112 greatly improves the torsional strength of the balloon catheter 102 so that rotational force applied at the proximal portion 104 of the balloon catheter 102 may be transferred to the distal portion 108 of the balloon catheter 102, which includes the balloon-expandable prosthesis 101. This increase in torsional strength is provided without any substantial decrease in the deflection capability of the distal portion 108 of the balloon catheter 102. The outer shaft 112 of the balloon catheter 102 has a high torsional stiffness and is configured for improved torque transmission such that torque or rotation at or near the proximal end 114 of the outer shaft 112 (represented by directional arrow 115A) exhibits a highly sensitive and functional response ratio compared to rotation or torque of the distal portion 108 of the balloon catheter 102 (represented by directional arrow 115*b*) when the outer shaft 112 is rotated 360 degrees, even when the delivery system 100 is in a bent or curved position as shown in FIGS. 3 and 4 above. The outer shaft 112, and effectively the balloon catheter 102 and the balloon-expandable prosthesis 101 mounted thereon, is thus operable to be rotated 360 degrees without kinking or building up recoil or tension in the outer shaft 112 when the outer shaft 112 is rotated. As such, the outer shaft 112 is configured to result in improved circumferential positioning of the balloon-expandable prosthesis 101 in situ to avoid blocking the ostia of the coronary arteries and/or to align commissures of the balloon-expandable prosthesis 101 with the native valve commissures as described above.

As shown in the side of FIG. 6, which is a side view of the outer shaft 112 removed from the balloon catheter 102 for sake of illustration only, the elongated tubular body 118 has a length L1 from the proximal end 114 to the distal end 116 thereof. For illustrative purposes only, the elongate tubular body 118 of the outer shaft 112 is described herein as having three longitudinal portions, i.e., a proximal portion 122, a distal portion 126, and an intermediate portion 124 extending between the proximal portion 122 and the distal portion 126. The portions 122, 124, 126 are integral or continuous portions of the elongate tubular body 118 but have different constructions as described herein. While the elongated tubular body is described herein as including the proximal, intermediate, and distal portions 122, 124, 126, the outer shaft 112 may include additional portions or segments proximal to the proximal portion 122 or distal to the distal portion 126 without departing from the scope of the invention. The proximal, intermediate, and distal portions 122, 124, 126 are the integral portions of the outer shaft 112 that are sufficiently flexible to bend. However, the outer shaft 112 may include additional portions or segments proximal to the proximal portion 122 or distal to the distal portion 126 that are relatively rigid and not configured to flex or bend. For example, the outer shaft 112 may include a proximal-most portion proximal to the proximal portion 122 that is configured to permit passage of the pull wire 152 into the handle 106, and such a proximal-most portion is configured to be relatively rigid and not sufficiently flexible to bend. In another example, the outer shaft 112 may include a distal-most portion distal to the distal portion 126 that is configured to facilitate bonding of the outer shaft 112 to the balloon 110 and connection to the distal end of the pull wire 152, and such a distal-most portion is configured to be relatively rigid and not sufficiently flexible to bend.

In an embodiment, the proximal portion 122 extends between 75-90% of the length L1 of the elongated tubular body 118, the intermediate portion extends 124 between 5-10% of the length L1 of the elongated tubular body 118, and the distal portion 126 extends between 5-15% of the length L1 of the elongated tubular body 118. In an embodiment, the proximal portion 122 extends between 82-86% of the length L1 of the elongated tubular body 118 with a length of approximately 1040 mm, the intermediate portion extends 124 between 6-8% of the length L1 of the elongated tubular body 118 with a length of approximately 70 mm, and the distal portion 126 extends between 8-10% of the length L1 of the elongated tubular body 118 with a length of approximately 86 mm. The respective lengths of portions 122, 124, and 126 are configured to correspond to arc lengths within the anatomy through which the delivery system 100 is tracked, i.e., arc lengths within the aortic arch. In an embodiment, the elongated tubular body 118 has an outer diameter that is constant along the length L1. In another embodiment (not shown), the elongated tubular body 118 has a first outer diameter that is constant along the proximal portion 122 and a second outer diameter that is constant along the intermediate portion 124 and the distal portion 126, the first outer diameter being greater than the second outer diameter. In another embodiment (not shown), the elongated tubular body 118 has a first outer diameter that is constant along the proximal portion 122, a second outer diameter that is constant along the intermediate portion 124, and a third outer diameter that is constant along the distal portion 126, the first outer diameter being greater than each of the second outer diameter and the third outer diameter and the third outer diameter of the distal portion 126 being slightly greater than the second outer diameter of the intermediate portion 124.

Figures 9A, 9B, 9C, 9D:
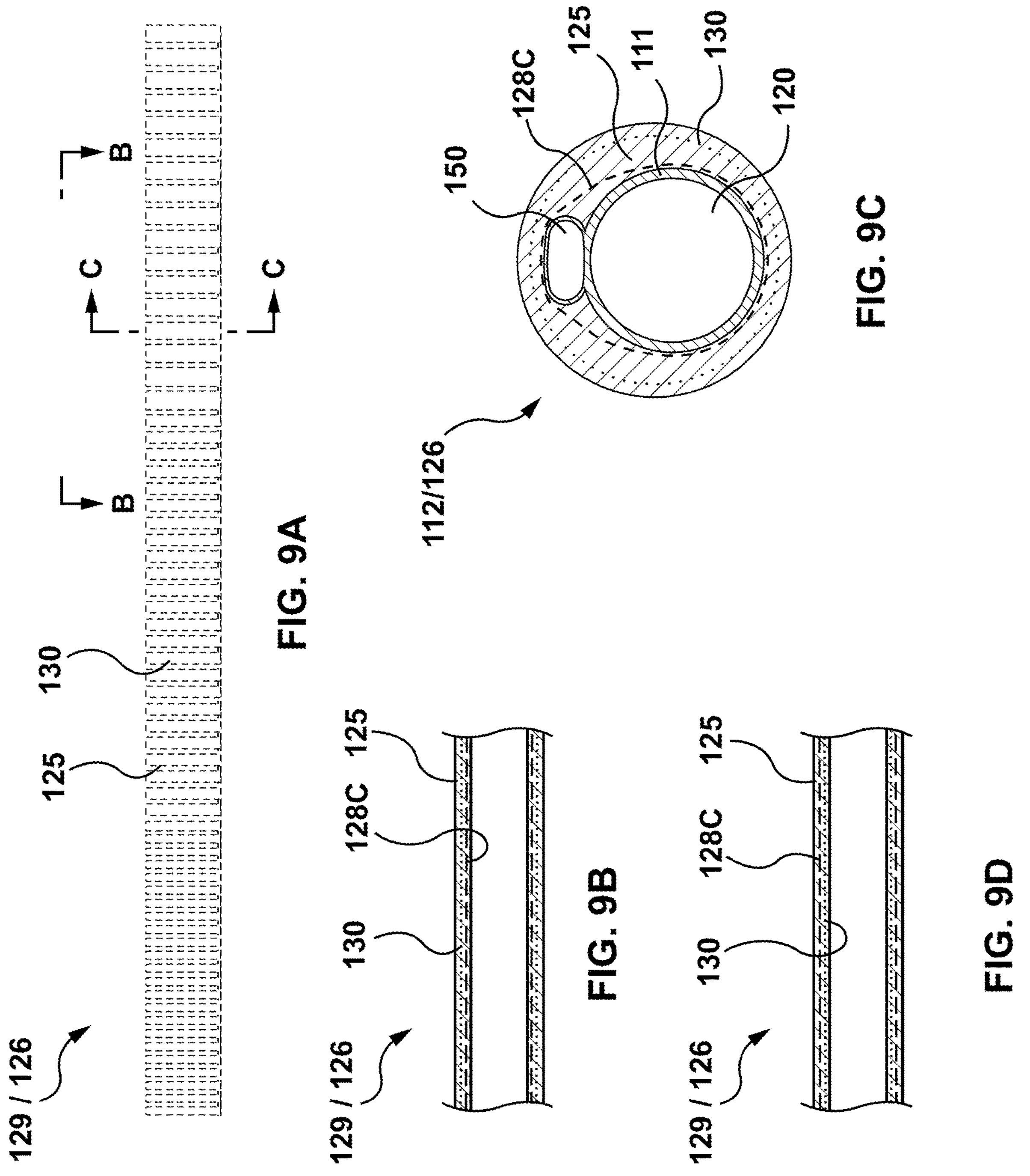
FIG. 9A is an enlarged side view of a distal portion of the outer shaft of FIG. 6, wherein the distal portion of the outer shaft includes the tubular braid component and the hypotube disposed within a third polymer.
FIG. 9B is a sectional view taken along like B-B of FIG. 9A.
FIG. 9C is a cross-sectional view taken along line C-C of FIG. 9A.
FIG. 9D is a sectional view taken along line B-B of FIG. 9A according to an alternative embodiment hereof.

FIG. 7A is an enlarged side view of a portion of the proximal portion 122 of the outer shaft 112, while FIG. 7B is a sectional view taken along line B-B of FIG. 7A and FIG. 7C is a cross-sectional view taken along line C-C of FIG. 7A. The proximal portion 122 of the elongate tubular body 118 of the outer shaft 112 includes a first polymer 121 having a first stiffness. FIG. 8A is an enlarged side view of a portion of the intermediate portion 124 of the outer shaft 112, while FIG. 8B is a sectional view taken along line B-B of FIG. 8A and FIG. 8C is a cross-sectional view taken along line C-C of FIG. 8A. The intermediate portion 124 of the elongate tubular body 118 of the outer shaft 112 includes a second polymer 123 having a second stiffness. FIG. 9A is an enlarged side view of a portion of the distal portion 126, while FIG. 9B is a sectional view taken along line B-B of FIG. 9A and FIG. 9C is a cross-sectional view taken along line C-C of FIG. 9A. The distal portion 126 of the elongate tubular body 118 of the outer shaft 112 includes a third polymer 125 having a third stiffness. The second stiffness of the second polymer 123 is less than the first stiffness of the first polymer 121 and the third stiffness of the third polymer 125 is less than the second stiffness of the second polymer 123. The portions 122, 124, 126 may be formed of one or more polymeric materials including polyamide family members or polyethylene of varying molecular weights. In an embodiment, the first polymer 121 is VESTAMID® ML24, the second polymer 123 is PEBAX® 63D, and the third polymer 125 is PEBAX® 35D.

As shown in each of the side views of FIGS. 7A, 8A, and 9A, the outer shaft 112 includes the tubular braid component 128 that extends the entire length L1 of the outer shaft 112, from the proximal end 114 to the distal end 116 thereof. Stated another way, a length of the tubular braid component 128 is the same as or substantially the same as the length L1 of the elongate tubular body 118 of the outer shaft 112. For illustrative purposes only, the tubular braid component 128 is described herein as having three longitudinal portions, i.e., a first portion 128A, a second portion 128B, and a third portion 128C. However, portions 128A, 128B, 128C are integral or continuous portions of the tubular braid component 128 and have the same braided construction. More particularly, the proximal portion 122 of the elongate tubular body 118 of the outer shaft 112 includes the first portion 128A of the tubular braid component 128 extending or embedded within the first polymer 121. The intermediate portion 124 of the elongate tubular body 118 of the outer shaft 112 includes the second portion 128B of the tubular braid component 128 extending or embedded within the second polymer 123. The distal portion 126 of the elongate tubular body 118 of the outer shaft 112 includes the third portion 128C of the tubular braid component 128 extending or embedded within the third polymer 125. In addition to the third portion 128C of the tubular braid component 128, along an overlap segment 129, the distal portion 126 of the elongate tubular body 118 of the outer shaft 112 also includes a hypotube 130. The third polymer 125 is disposed in and around the third portion 128C of the tubular braid component 128 and the hypotube 130 along the overlap segment 129 of the distal portion 126. The third portion 128C of the tubular braid component 128 and the hypotube 130 overlap each other along the overlap segment 129. More particularly, the hypotube 130 overlaps or overlays the third portion 128C of the tubular braid component 128 as shown in the sectional view of FIG. 9B, or alternatively the third portion 128C of the tubular braid component 128 may overlap or overlay the hypotube 130 as shown in the sectional view of FIG. 9D, such that only the distal portion 126 of the outer shaft 112 includes both the tubular braid component 128 and the hypotube 130. Stated another way, the hypotube 130 may be disposed or incorporated either under or over the third portion 128C of the tubular braid component 128. Such an arrangement has improved torqueability compared to other catheter shafts having braided and/or axial wire reinforcements. Since the hypotube 130 is disposed only at the distal portion 126 of the outer shaft 112, which includes the third polymer 125 having the third stiffness, the hypotube 130 is disposed at the most flexible portion of the outer shaft 112 in order to improve torsional performance while still maintaining local flexibility due to the laser cut pattern of the hypotube 130 which will be described in more detail below. The hypotube 130 is reflowed with the third polymer 125 to facilitate flexibility, because the third polymer 125 fills the voids formed by the laser cut pattern of the hypotube 130.

The tubular braid component 128 may be formed of a material such as stainless steel, Nitinol, tungsten, carbon, aramid, glass fibre, a stainless steel that has been reinforced with polyimide, or molybdenum. Preferably, the material utilized for the tubular braid component 128 has an Ultimate Tensile Strength (UTS) in the range of 200,000 to 350,000 lbs/in$^2$. In an embodiment, the material utilized for the tubular braid component 128 is high temper stainless steel type 2913B ribbon wire. The material utilized for the tubular braid component 128 can be terminated by welding the ribbon wires where the ribbon wires cross (pic crossings).

The tubular braid component 128 may be woven in many different types of patterns. In the embodiment depicted herein, the tubular braid component 128 is a one-over, one-under woven or braided pattern and is a sixteen carrier flat wire design including eight ribbon wires or strands extending in a clockwise direction and eight ribbon wires or strands extending in a counter-clockwise direction. The tubular braid component 128 is formed from ribbon wire having a rectangular cross-section having a width between 0.004-0.020 inches. While other shapes are also acceptable, the flattened construction of the filament that forms the tubular braid component 128 provides more mass and thus an enhanced steerability. Preferably, the ribbon wire has a thickness less than 0.0020 inches. In an embodiment, the tubular braid component 128 is woven from ribbon wire that is 0.0015 thick and 0.010 inches wide, and has a pic count between 25 and 50. In an embodiment, the pic count is between 25-35. Pic count is a measurement of the tightness of the weave of the tubular braid component 128. Pic count is calculated by counting the number of times the ribbon wires in the first direction and the ribbon wires in a second direction cross within a one-inch line drawn longitudinally along the outer shaft 112. It is important to maintain a pic count that is not so great that deflection capability of the outer shaft 112 is impacted. Stated another way, it is desirable for the weave of the tubular braid component 128 to include spaces between woven ribbon wires to allow the strands to move slightly when the outer shaft 112 is bent, deflected, or otherwise manipulated in situ during steering. If the ribbon wires are woven so tightly that no spaces remain, more force must be applied to the pull wire 152 to achieve bending of the outer shaft 112.

Figure 10:
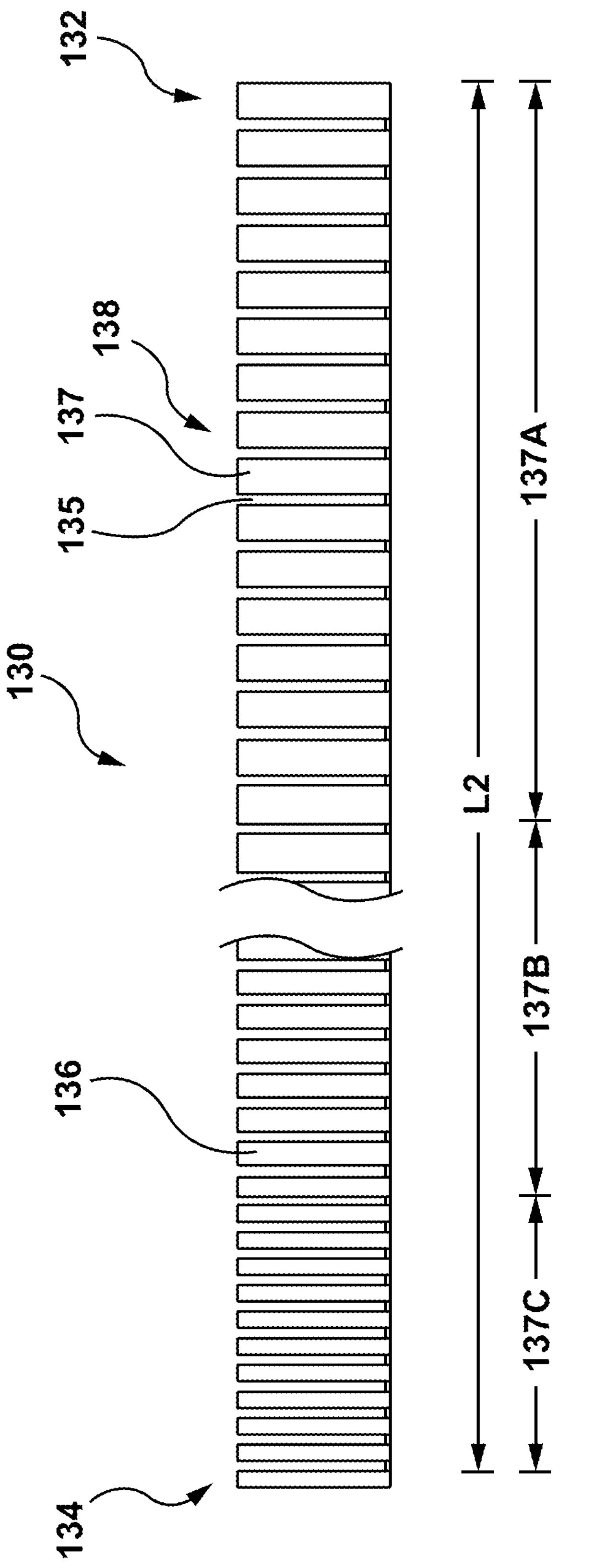
FIG. 10 is a side view of the hypotube of FIG. 9A, wherein the hypotube is removed from the outer shaft for sake of illustration.

The hypotube 130 is a tubular component configured for elastic deformation. In some embodiments, the hypotube 130 is a Nitinol super elastic material. In another embodiment, the hypotube is formed from stainless steel and the geometry of the hypotube 130 (i.e., a cut pattern 138 described below) configures the hypotube 130 for elastic deformation. As shown in FIG. 10, which is a side view of the hypotube 130 removed from the outer shaft 112 for illustrative purposes, the hypotube 130 has a proximal end 132, a distal end 134, a length L2 between the proximal end 132 and the distal end 134, and a sidewall 136 having the cut pattern 138. The cut pattern 138 is configured so as to not create a significant directional bias or limit the degrees of freedom. The cut pattern 138 includes a continuous coil or helical configuration with a slot 135 that spirals around the sidewall 136 to form a plurality of generally circumferentially extending successive windings 137. In an embodiment, the plurality of successive windings 137 includes a first plurality of successive windings 137A, a second plurality of successive windings 137B, and a third plurality of successive windings 137C. The second plurality of successive windings 137B are disposed distal to the first plurality of successive windings 137A and the third plurality of successive windings 137C being disposed distal to the second plurality of successive windings 137B. Each winding of the first plurality of successive windings 137A has a first width, each winding of the second plurality of successive windings 137B has a second width, and each winding of the third plurality of successive windings 137C has a third width, with the second width being greater than the third width and the first width being greater than the second width. The width of slot 135 is constant, but the width of the plurality of successive windings 137 decreases in a distal direction. As a result, the stiffness of the hypotube 130 also varies along a length thereof and decreases in a distal direction such that the distal end thereof is the most flexible. When incorporated into the outer shaft 112, the varying flexibility of the hypotube 130 is imparted onto the outer shaft 112 such that the overlap segment 129 would also have a variable flexibility that decreases in a distal direction such that the distal end thereof is the most flexible. The slot 135 and the plurality of windings 137 are formed via laser-cutting the hypotube 130 and are configured to impart non-kinking flexibility to the hypotube 130 that allows the hypotube 130 to bend when the pull wire 152 is selectively tensioned, thereby reducing the pulling force required for bending the hypotube 130.

As described above, each of the proximal portion 122 and the intermediate portion 124 of the outer shaft 112 includes the first and second portion 128A, 128B of the tubular braid component 128, respectively. The distal portion 126 of the outer shaft 112 includes the third portion 128C of the tubular braid component 128, and further includes the hypotube 130 along the overlap segment 129. Along the overlap segment 129 of the distal portion 126, each of the third portion 128C of the tubular braid component 128 and the hypotube 130 extends within the third polymer 125. As shown in FIG. 9B, the length L2 of the hypotube 130 may be disposed over the third portion 128C of the tubular braid component 128 or alternatively as shown in FIG. 9D, the third portion 128C of the tubular braid component 128 may be disposed over the length L2 of the hypotube 130. The third polymer 125 is disposed in and around the third portion 128C of the tubular braid component 128 and the length L2 of the hypotube 130 along the overlap segment 129 of the distal portion 126. In an embodiment, the third polymer 125 extends through the slot 135 of the cut pattern 138 of the hypotube 130 as well as through the spaces between woven ribbon wires of the third portion 128C of the tubular braid component 128. The third polymer 125 may be reflowed during manufacture to allow the polymeric material to pass through the slot 135 of the cut pattern 138 of the hypotube 130 as well as through the spaces or voids of the third portion 128C of the tubular braid component 128. In an embodiment, reflowing of the third polymer 125 occurs in two separate processing steps. In a first processing step, a first jacket of the third polymer 125 is reflowed over the third portion 128C of the tubular braid component 128, one or more mandrels configured to form the pull wire lumen 150, and the innermost layer 111. The first processing step results in a subassembly, and the hypotube 130 is then positioned over the subassembly after the first processing step. In a second processing step, performed after the first processing step, a second jacket of the third polymer 125 is reflowed over the hypotube 130 and the subassembly. The two processing steps collectively result in both the hypotube 130 and the third portion 128C of the tubular braid component 128 being embedded within the third polymer 125.

As shown on FIG. 6, distal to the overlap segment 129, the third portion 128C of the tubular braid component 128 extends distally beyond the distal end 134 of the hypotube 130. Stated another way, the third portion 128C of the tubular braid component 128 has a distal end that longitudinally terminates distal to the distal end 134 of the hypotube 130. In another embodiment (not shown), the third portion 128C of the tubular braid component 128 has a distal end that longitudinally terminates with the distal end 134 of the hypotube 130 such that the tubular braid component 128 does not extend distally beyond the distal end 134 of the hypotube 130.

The stiffness of the proximal portion 122 of the outer shaft 112 which includes the first polymer 121 and the first portion 128A of the tubular braid component 128, is constant along a length thereof. In an embodiment, the stiffness or flexural modulus of the proximal portion 122 is between 50,000 and 80,000 N-mm$^2$, or 7,250,000 and 11,600,000 psi. Similarly, the stiffness of the intermediate portion 124 of the outer shaft 112 which includes the second polymer 123 and the second portion 128B of the tubular braid component 128, is also constant along a length thereof. In an embodiment, the stiffness or flexural modulus of the intermediate portion 124 is between 7,000 and 9,000 N-mm$^2$, or 1,015,000 and 1,305,000 psi. The stiffness of the distal portion 126 of the outer shaft 112 varies along a length thereof since a proximal portion thereof includes the third polymer 125, the third portion 128C of the tubular braid component 128, and the hypotube 130, while a distal portion thereof includes the third polymer 125 and the third portion 128C of the tubular braid component 128. Further, the stiffness of the distal portion 126 depends upon the cut pattern 138 of the hypotube 130. The stiffness of the hypotube 130 may further vary along the length L2 of the hypotube 130 as described above with respect to FIG. 10. In an embodiment, the stiffness or flexural modulus of the distal portion 126 is between 1,500 and 2,000 N-mm$^2$, or 217,500 and 290,075 psi.

Figure 10A:
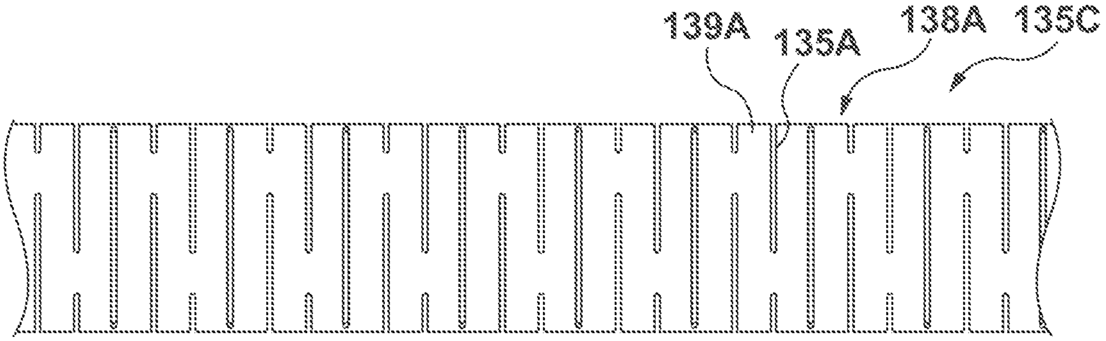
FIG. 10A is a side view of a hypotube configured for use within the outer shaft according to another embodiment hereof, wherein the hypotube is removed from the outer shaft for sake of illustration.

Although described above with the cut pattern 138, the hypotube 130 may include other cut patterns that result in the desired torquability transmission and transverse articulation of the outer shaft 112. For example, alternative cut patterns are shown in FIGS. 10A-10E. In the embodiment of FIG. 10A, a cut pattern 138A of a hypotube 130A is shown. The cut pattern 138A includes a plurality of voids or slots 135A longitudinally separated, or demarcated, by a plurality of ribs 139A, such that generally each rib 139A is separated from an adjacent rib 139A by a pair of circumferentially aligned slots 135A. Each slot 135A of the pair of circumferentially aligned slots 135A are circumferentially discontinuous, with each slot 135A of the pair extending less than 180°. The plurality of ribs 139A and the plurality of slots 135A substantially extend in a circumferential direction around the longitudinal axis LA of the delivery system 100. The plurality of ribs 139A and the plurality of slots 135A are formed via laser-cutting the hypotube 130A and are configured to impart non-kinking flexibility to the hypotube 130A that allows the hypotube 130A to bend when the pull wire 152 is selectively tensioned, thereby reducing the pulling force required for bending the hypotube 130A.

Figure 10B:
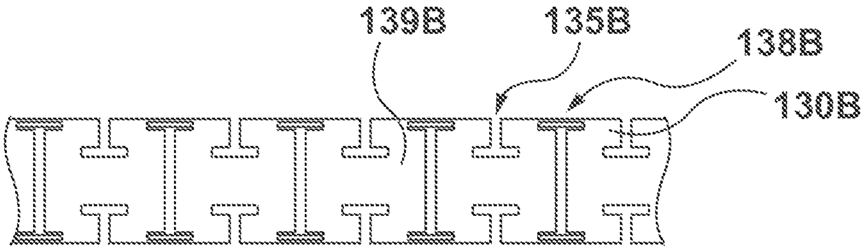
FIG. 10B is a side view of a hypotube configured for use within the outer shaft according to another embodiment hereof, wherein the hypotube is removed from the outer shaft for sake of illustration.

In the embodiment of FIG. 10B, a cut pattern 138B of a hypotube 130B is shown. The cut pattern 138B includes a plurality of voids or slots 135B longitudinally separated, or demarcated, by a plurality of ribs 139B, such that generally each rib 139B is separated from an adjacent rib 139B by a pair of circumferentially aligned slots 135B. Each slot of the pair of circumferentially aligned slots 135B is circumferentially discontinuous, with each slot 135B of the pair extending less than 180°. The plurality of ribs 139B and the plurality of slots 135B substantially extend in a circumferential direction around the longitudinal axis LA of the delivery system 100. The cut pattern 138B is similar to the cut pattern 138A except that each slot 135B includes a transverse or longitudinally-extending portion 133 at the ends thereof.

Figure 10C:
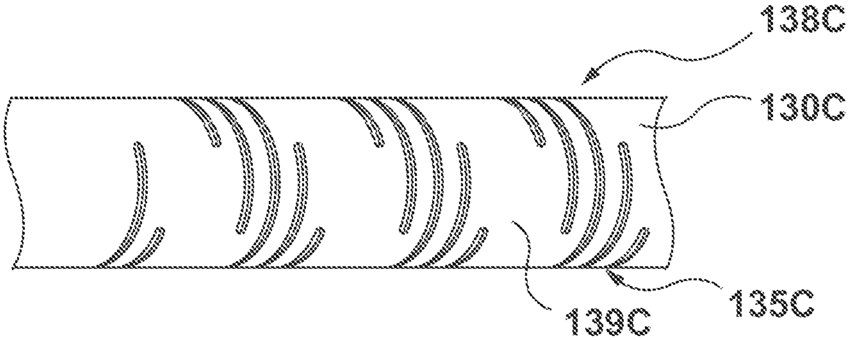
FIG. 10C is a side view of a hypotube configured for use within the outer shaft according to another embodiment hereof, wherein the hypotube is removed from the outer shaft for sake of illustration.

In the embodiment of FIG. 10C, a cut pattern 138C of a hypotube 130C is shown. The cut pattern 138C includes a plurality of voids or slots 135C longitudinally spaced apart from each other along the length of the hypotube to form a plurality of generally circumferentially extending ribs 139C. Each slot 135C has a partial coil or helix-like configuration such that the slot 135C spirals around the hypotube.

Figure 10D:
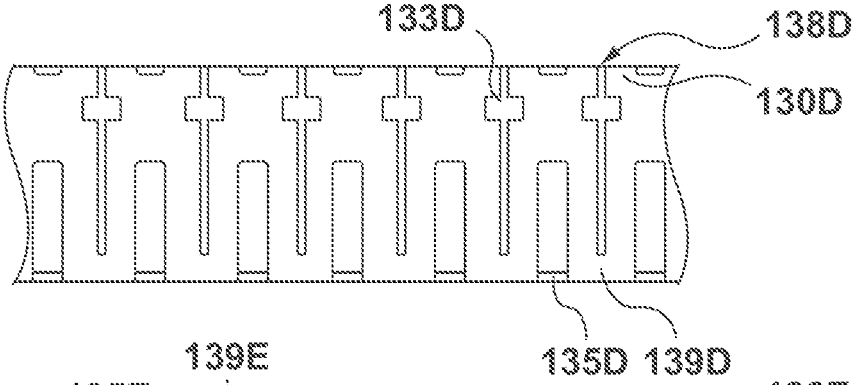
FIG. 10D is a side view of a hypotube configured for use within the outer shaft according to another embodiment hereof, wherein the hypotube is removed from the outer shaft for sake of illustration.

In the embodiment of FIG. 10D, a cut pattern 138D of a hypotube 130D is shown. The cut pattern 138D includes a plurality of voids or slots 135D longitudinally separated, or demarcated, by a plurality of ribs 139D, such that generally each rib 139D is separated from an adjacent rib 139D by a pair of circumferentially slots 135D. Each slot 135D of the pair of circumferentially aligned slots 135D are circumferentially discontinuous, with each slot 135D of the pair extending less than 180°. The plurality of ribs 139D and the plurality of slots 135D substantially extend in a circumferential direction around the longitudinal axis LA of the delivery system. The cut pattern 138D is similar to the cut pattern 138A except that the width of every other pair of circumferentially aligned slots 135D is relatively widened. Further, the relatively thinner pairs of circumferentially aligned slots 135E include an intermediate widened portion 133D along a length thereof.

Figure 10E:
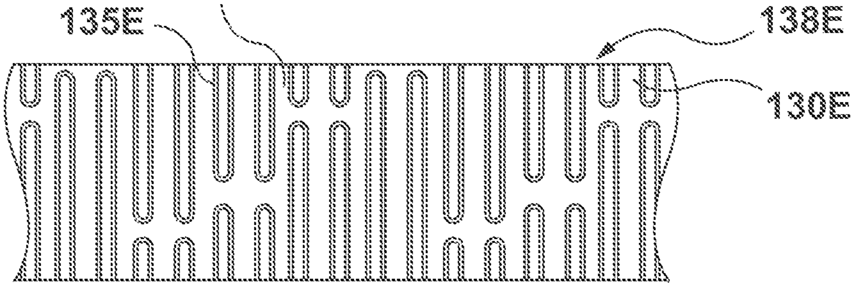
FIG. 10E is a side view of a hypotube configured for use within the outer shaft according to another embodiment hereof, wherein the hypotube is removed from the outer shaft for sake of illustration.

In the embodiment of FIG. 10E, a cut pattern 138E of a hypotube 130E is shown. The cut pattern 138E includes a plurality of U-shaped voids or slots 135E longitudinally spaced apart from each other along the length of the hypotube to form a plurality of ribs 139E, such that generally each rib 139E is separated from an adjacent rib 139E by a pair of circumferentially aligned U-shaped slots 135E. Each U-shaped slot 135E of the pair of U-shaped slots 135E are circumferentially discontinuous, with each U-shaped slot 135E of the pair extending less than 180°. The plurality of ribs 139E and the plurality of U-shaped slots 135E substantially extend in a circumferential direction around the longitudinal axis LA of the delivery system.

Figure 11:
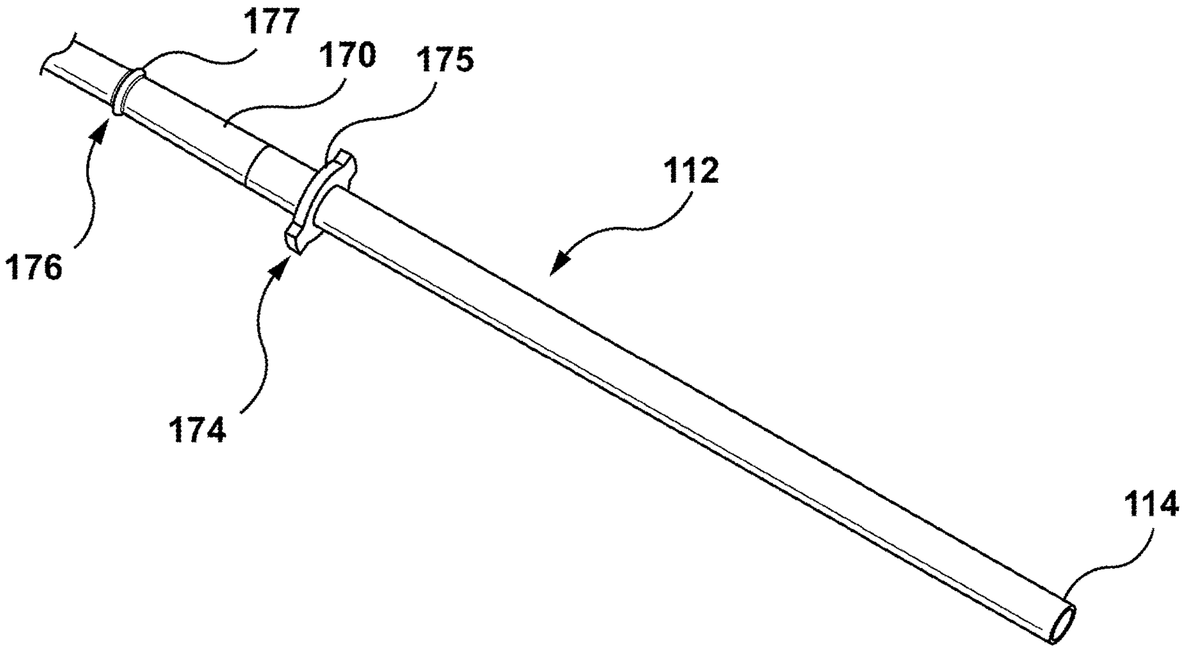
FIG. 11 is a perspective view of a portion of the outer shaft of the delivery system of FIG. 1 and a strain relief segment disposed over the outer shaft, wherein the outer shaft and the strain relief segment are removed from the delivery system for illustrative purposes.

As best shown in FIG. 11, the outer shaft 112 may further include a strain relief component 170 concentrically disposed over a portion of the outer shaft 112 proximate to the handle 106 that functions to relieve stress from the outer shaft 112 as it exits from the distal end of the housing 106. The strain relief component 170 is a relatively short tubular component that defines a lumen therethrough that extends from a proximal end 174 to a distal end 176 thereof. The proximal end 174 includes a radial flange 175 that is attached to the interior of the distal end of the handle 106. The distal end 176 of the strain relief component 170 extends or protrudes from a distal end of the handle 106 and includes a circumferential bump or raised ring 177 that is configured to mate with a valve relief component 180 as will be described in more detail herein with respect to FIGS. 12-14. As will be described in more detail herein, the valve relief component 180 is a component that is slidingly disposed over an outer surface of the outer shaft 112 and is configured to be selectively disposed over the balloon-expandable prosthesis 101 to protect the balloon-expandable prosthesis 101 during insertion into an introducer sheath. The valve relief component 180 serves also to relieve strain of the distal portion of the balloon catheter 102 when the catheter is inserted through an introducer sheath. The strain relief component 170 is configured to serve as a docking station for the valve relief component 180 when the valve relief component 180 is not disposed over the balloon-expandable prosthesis 101 to ensure it does not slide on the balloon catheter 102 during the procedure. The valve relief component 180 is secured or docked onto the raised ring 177 of the strain relief component 170 through an interference fit.

Figure 12:
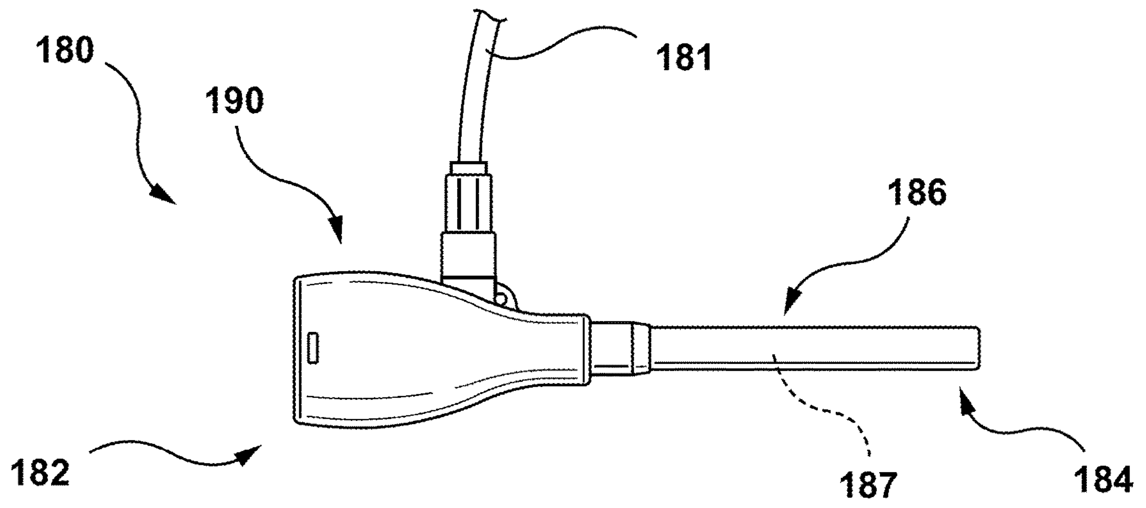
FIG. 12 is a side view of a valve relief component that may be utilized with the delivery system of FIG. 1.

As shown on FIG. 12, the valve relief component 180 includes a proximal end 182 and a distal end 184. A hub 190 including a hemostasis valve or seal is disposed at the proximal end 182 of the valve relief component 180. A flush port 181 is provided on the hub 190. The hemostasis valve or seal of the hub 190 may be formed from a flexible material such as silicone and may include a lubricious coating such as parylene or silicone oil. The hemostasis valve or seal of the hub 190 is configured to passively or actively seal against the outer shaft 112 when the outer shaft 112 is disposed therethrough, creating hemostasis.

Distally extending from the hub 190 is a sheath 186. The sheath 186 is a tubular or cylindrical element defining a single lumen 187 therethrough. The sheath 186 is sized to be used with an introducer sheath with the lumen 187 being sized or configured to slidingly receive the outer shaft 112 of the balloon catheter 102, including the distal portion of the outer shaft 112 having the balloon-expandable prosthesis 101 disposed thereon. The sheath 186 is of a sufficient length to cover or extend over the full or entire length of the balloon-expandable prosthesis 101 in its delivery or compressed configuration, and thus the particular length of the sheath 186 may vary depending upon the application and length of the balloon-expandable prosthesis 101.

The sheath 186 may be formed of one or more relatively rigid polymeric materials such as but not limited to polyethylene. Optionally, the sheath 186 or some portion thereof may be formed as a composite having a reinforcement layer incorporated within a polymeric body in order to enhance strength and/or flexibility. Suitable reinforcement layers include braiding, wire mesh layers, embedded axial wires, embedded helical or circumferential wires, hypotubes, and the like. In one embodiment, for example, the entire length of the sheath 186 is formed from a reinforced polymeric tube. In this embodiment, the sheath 186 is opaque. In another embodiment, the sheath 186 is translucent to allow visual inspection of the balloon-expandable prosthesis 101 when the sheath 186 is disposed thereover.

Figure 13:
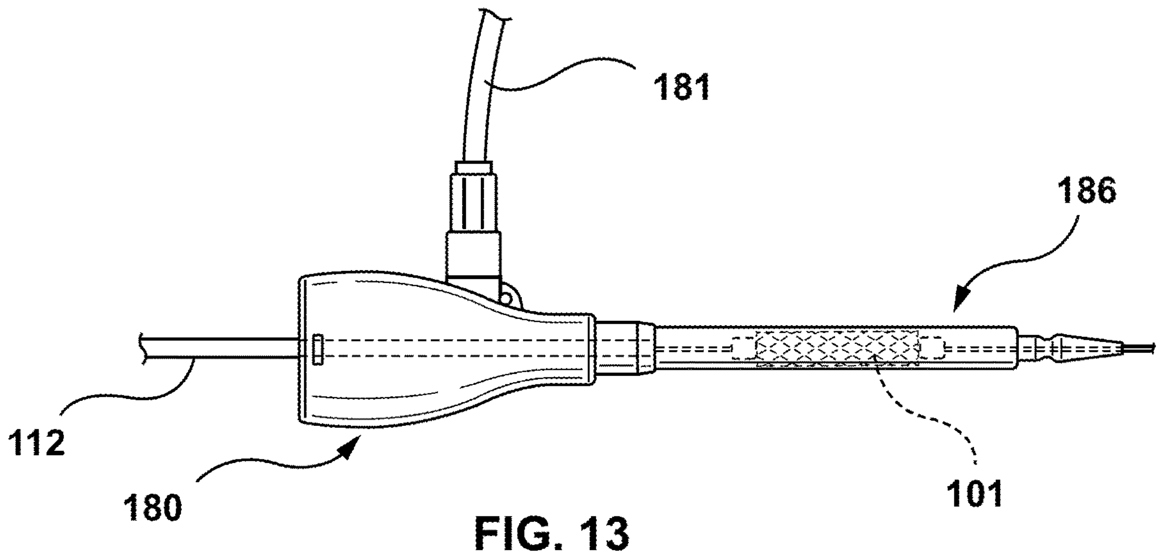
FIG. 13 is a side view of the distal portion of the delivery system of FIG. 1, wherein the valve relief component of FIG. 12 is disposed over the balloon-expandable prosthesis.

The valve relief component 180 is slidable relative to the outer shaft 112 of the balloon catheter 102 such that the valve relief component 180 may be easily moved along the outer shaft 112 in a longitudinal direction. As such, the valve relief component 180 is configured to be selectively disposed over the balloon-expandable prosthesis 101 to protect the balloon-expandable prosthesis 101 during insertion into an introducer sheath. More particularly, FIG. 13 is a side view of the distal portion 108 of the balloon catheter 102 with the sheath 186 of the valve relief component 180 disposed over the balloon-expandable prosthesis 101. When positioned over the balloon-expandable prosthesis 101, the valve relief component 180 reduces or eliminates the external forces that the balloon-expandable prosthesis 101 experiences when loaded through a hemostatic valve of an introducer sheath (not shown).

For example, in an embodiment, the balloon-expandable prosthesis 101 is a transcatheter aortic valve replacement prosthesis. When such a transcatheter aortic valve replacement prosthesis is inserted into an introducer sheath, tissue of the transcatheter aortic valve replacement prosthesis comes in contact with the hemostasis valve of the introducer sheath. The hemostasis valve of the introducer sheath may impart enough force on the transcatheter aortic valve replacement prosthesis to damage and/or displace the transcatheter aortic valve replacement prosthesis. However, when the valve relief component 180 is positioned over the transcatheter aortic valve replacement prosthesis, the valve relief component 180 protects the transcatheter aortic valve replacement prosthesis from damage or displacement by reducing or eliminating the external forces that the transcatheter aortic valve replacement prosthesis experiences when loaded through a hemostatic valve of the introducer sheath.

Figure 14:
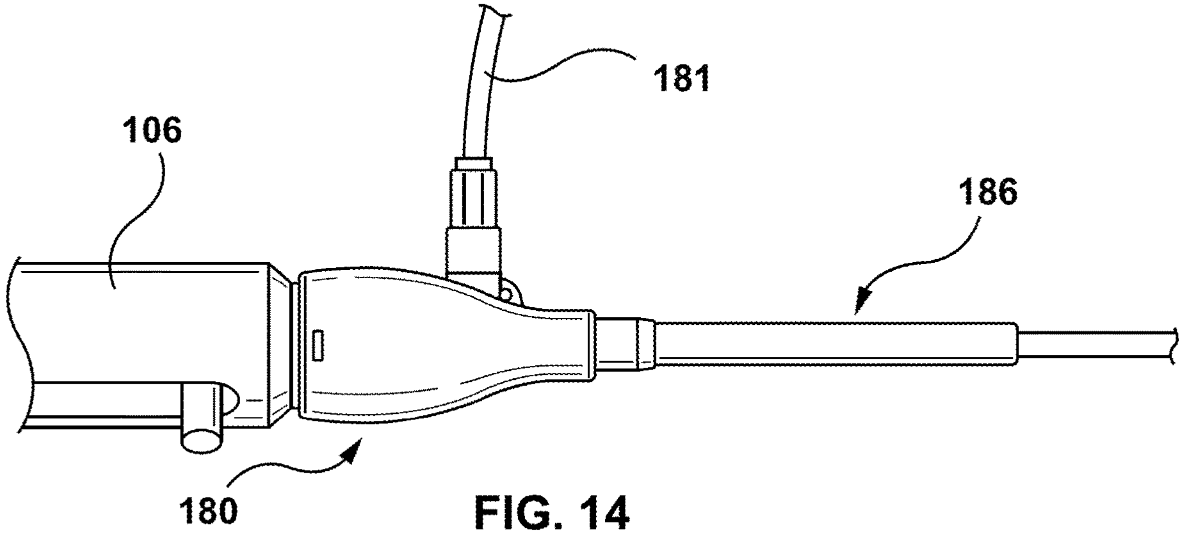
FIG. 14 is a side view of a proximal portion of the delivery system of FIG. 1, wherein the valve relief component of FIG. 12 is docked onto the strain relief component of the delivery system.

After being advanced through an introducer sheath, it is no longer required to have the valve relief component 180 disposed over the balloon-expandable prosthesis 101 at the site of insertion. As such, the valve relief component 180 is configured to dock onto the strain relief component 170 of the balloon catheter 102 as shown in FIG. 14. More particularly, the strain relief component 170 of the balloon catheter 102 is configured to serve as a docking station for the valve relief component 180 when the valve relief component 180 is not disposed over the balloon-expandable prosthesis 101. As described above, the distal end 176 of the strain relief component 170 extends or protrudes from a distal end of the handle 106 and includes the raised ring 177. The valve relief component 180 is secured or docked onto the raised ring 177 of the strain relief component 170 through an interference fit between the raised ring 177 and the inner surface of the valve relief component 180. Steering may still be actuated via the actuator 107 when the valve relief component 180 is docked or secured onto the strain relief component 170. After being docked onto the strain relief component 170, the valve relief component 180 does not freely slide along the balloon catheter 102 which may be bothersome to the user.

Other valve relief components may be utilized herein. More particularly, any valve relief component described in U.S. patent application Ser. No. 16/907,466, filed Jun. 22, 2020, which is herein incorporated by reference in its entirety and is assigned to the same assignee as the present disclosure, may be utilized herein.

Figure 15:
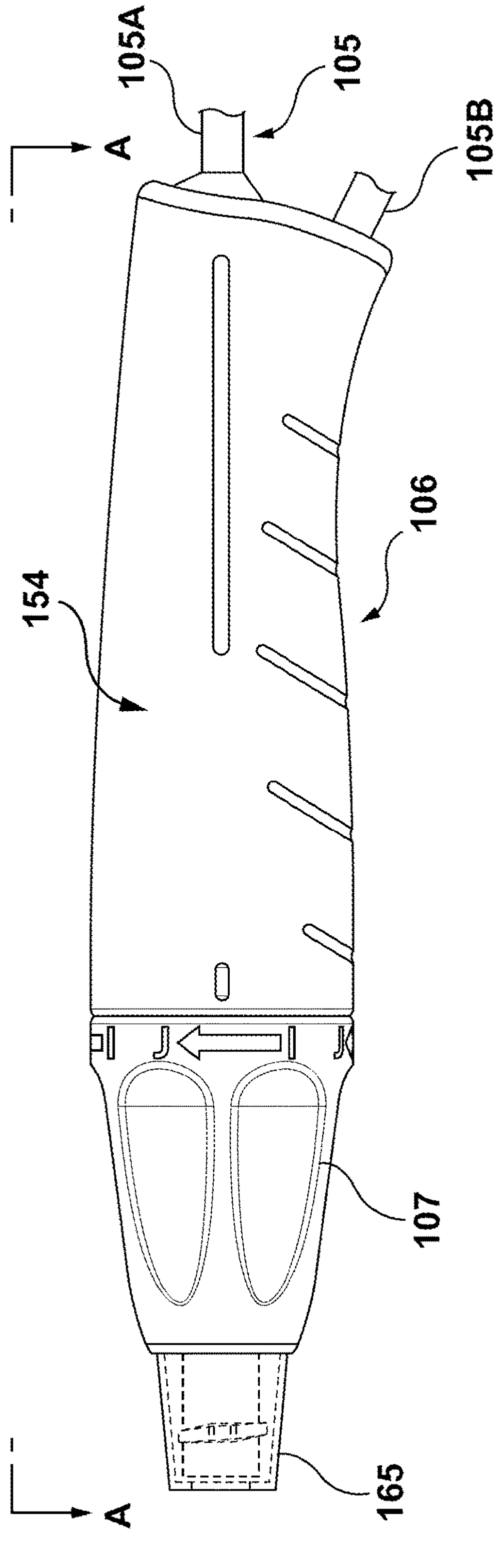
FIG. 15 is an enlarged side view of a handle of the delivery system of FIG. 1.
Figure 15A:
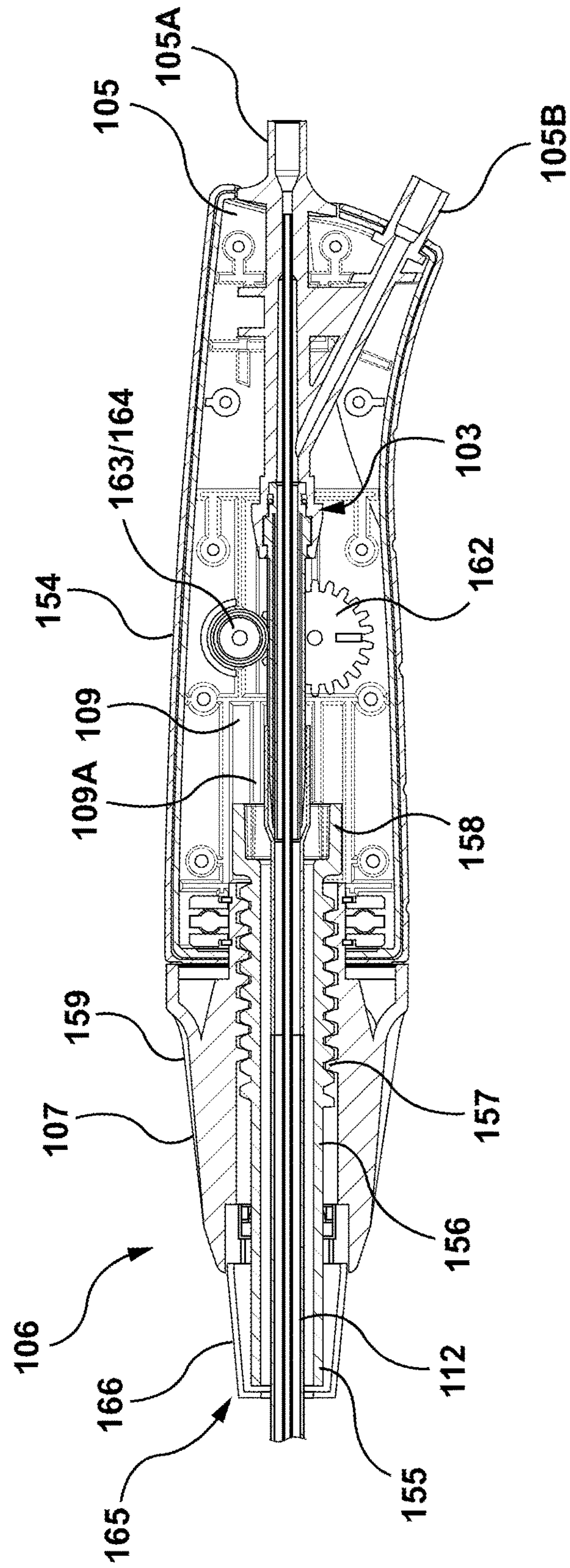
FIG. 15A is a sectional view of the handle of FIG. 15.

The handle 106 will now be described in more detail with respect to FIGS. 15-18. The handle 106 is adapted to house the steering mechanism therein to operate the pull wire 152. As described above, the handle 106 includes the actuator 107 which may be a knob operable to be rotationally manipulated by a user to selectively tension the pull wire 152. The actuator 107 is disposed at a distal end of the handle 106. The handle 106 includes a housing 154 that houses the internal components of the steering mechanism, which are operatively coupled to the actuator 107 and the proximal end of the pull wire 152 as best shown in the sectional view of FIG. 15A taken along line A-A of FIG. 15 as well as the perspective illustrative view of select components shown in FIG. 16. The steering mechanism includes the actuator 107, a slider 158, a driving gear 162, a reel gear 163, and a reel 164 attached to the reel gear 163. The slider 158 includes at a distal portion thereof a threaded rod 156 that is configured to interact with the actuator 107 and at a proximal portion thereof a rack 160 having a plurality of teeth 161 thereon that is configured to interact with the driving gear 162. The actuator 107 includes an internal threaded portion 159 that is configured to mate with threads 157 of the threaded rod 156 of the slider 158. The slider 158 is configured with a lumen therethrough that is configured to permit passage of the proximal end 114 of the outer shaft 112. The slider 158 (including the threaded rod 156 and the rack 160) is configured for translation relative to the actuator 107, and moves linearly or in a longitudinal direction when the actuator 107 is rotated due to the mating relationship between the actuator 107 and the threaded rod 156.

Figure 16:
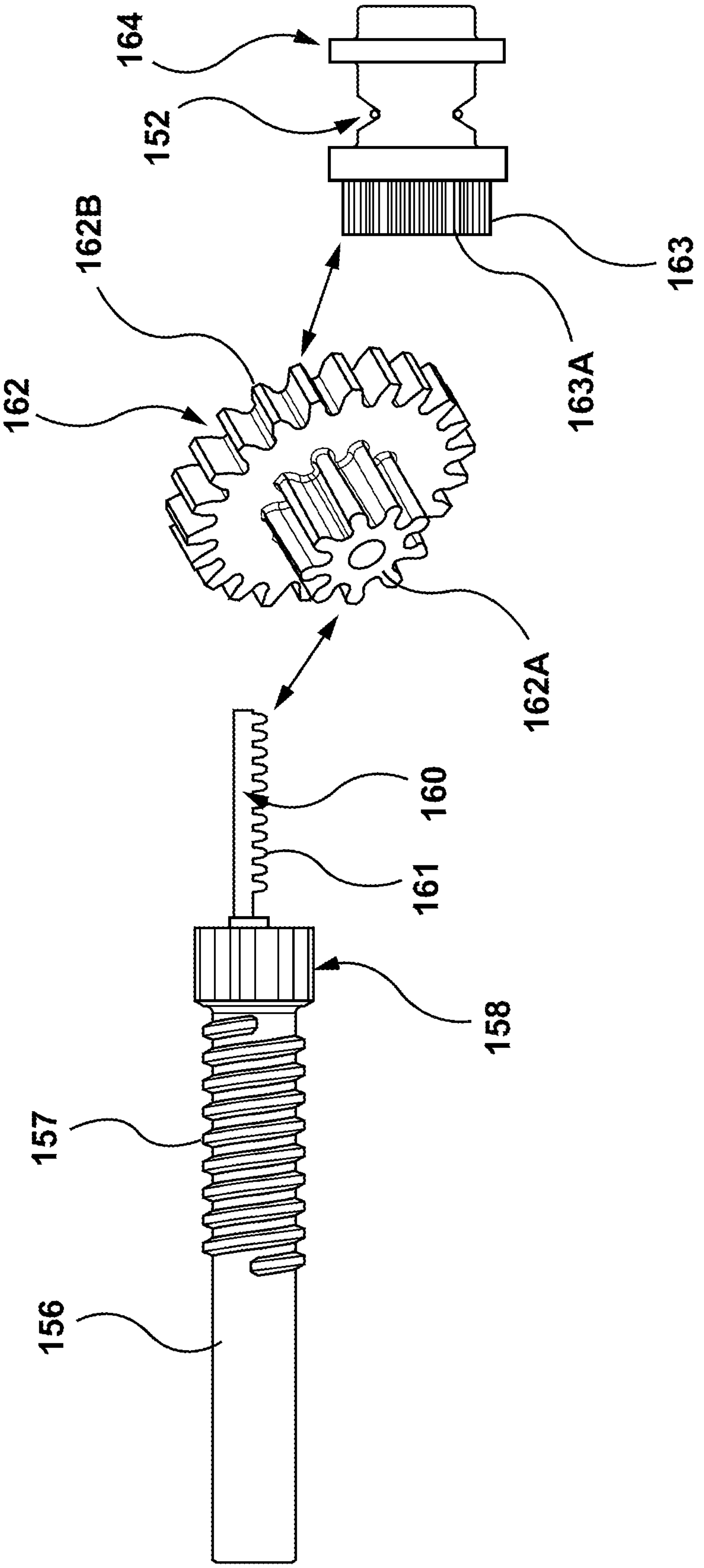
FIG. 16 is a perspective view of select components of the handle of FIG. 15, wherein the components are removed from a housing of the handle for sake of illustration only.
Figure 17:
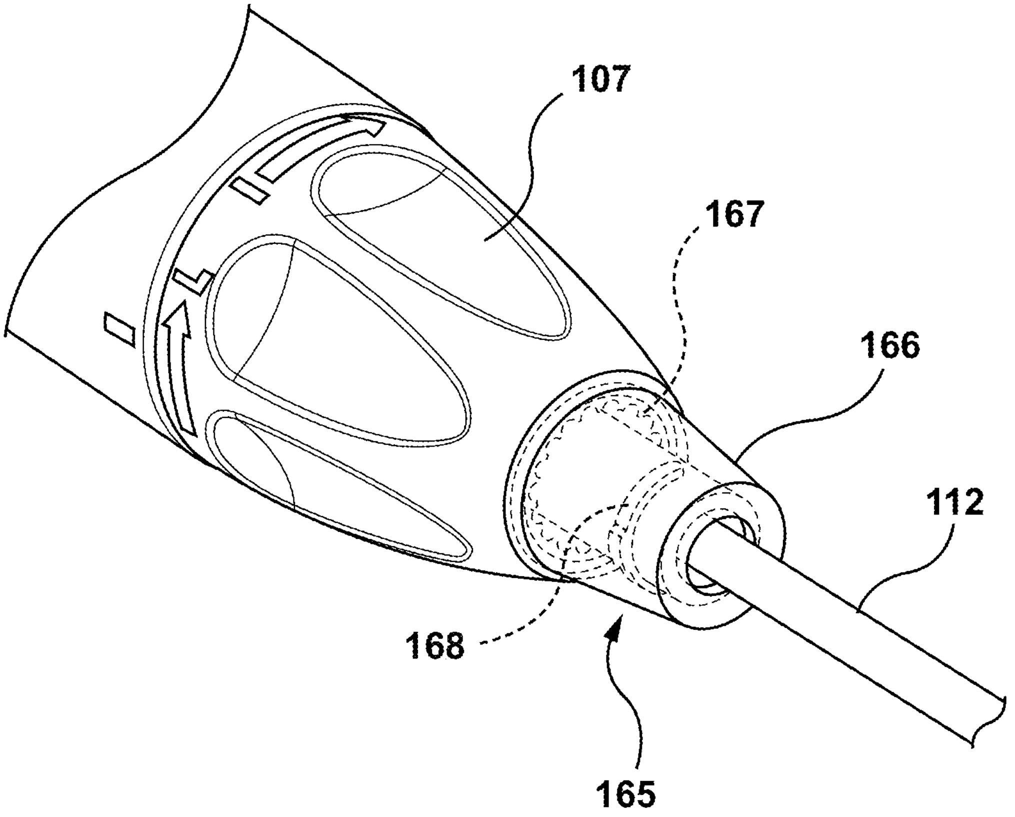
FIG. 17 is an enlarged perspective view of an actuator and a steering indicator of the handle of FIG. 15.
Figure 18:
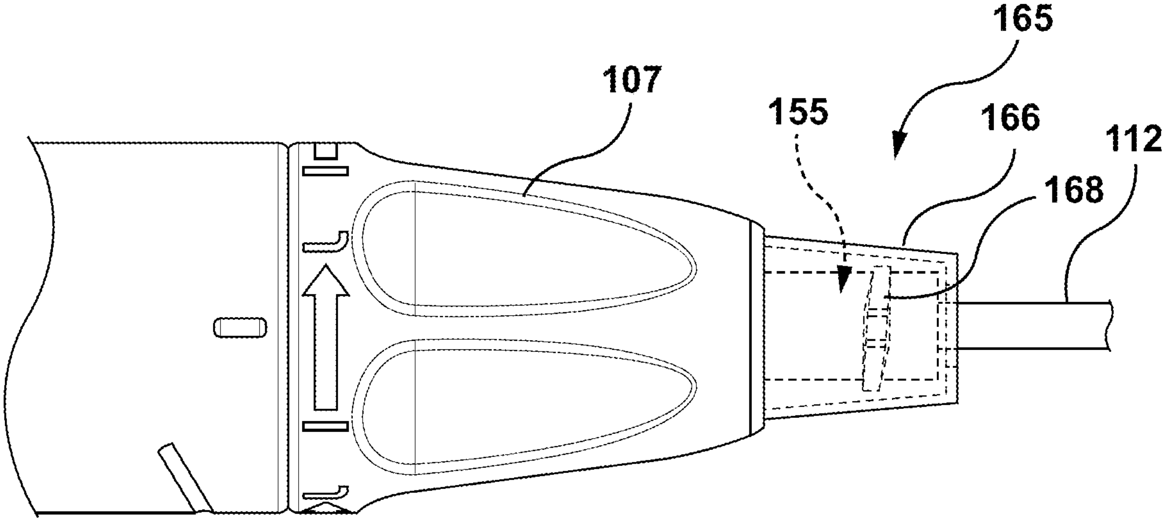
FIG. 18 is an enlarged side view of the actuator and the steering indicator of the handle of FIG. 15.

As best shown in the perspective view of FIG. 16, which illustrates select components removed from the housing 154 of the handle 106 for illustrative purposes only for description of the operation thereof, the driving gear 162 is coupled to the slider 158 via the rack 160 and is configured to engage with the teeth 161 of the rack 160. As the rack 160 moves linearly, the teeth 161 of the rack 160 mesh with teeth 162A of the driving gear 162. As a result, the driving gear 162 rotates in a first direction (i.e., clockwise or counter-clockwise) and teeth 162B of the driving gear 162 mesh with teeth 163A of the reel gear 163 to cause rotation thereof in a second or opposing direction (i.e., the other of clockwise of counter-clockwise). The reel gear 163 is attached to the reel 164 to rotate therewith, and thus rotation of the reel gear 163 similarly rotates the reel 164 to wind pull wire 152 thereon. Stated another way, the pull wire 152 is attached to the reel 164 such that rotation of the reel 164 causes the pull wire 152 to wind or unwind around the reel 164.

In the embodiment provided, the actuator 107 is configured to rotate about the longitudinal axis LA of the delivery system 100 to drive the translation of the slider 158 relative to the housing 154 of the handle 106. More particularly, rotation by the actuator 107 translates the slider 158 in a generally proximal direction. Translation of the slider 158 engages the driving gear 162 via the rack 160 causing rotation of the driving gear 162, which causes rotation of the reel gear 163 and the reel 164 attached thereto. Rotation of the reel 164 acts to wind the pull wire 152. A ratio of the amount of rotation of the actuator 107 to an amount of rotation of the reel 164 is controlled by several factors, including the pitch of the thread 157 on the rod 156, the number of teeth 161 on the rack 160, the number of teeth 162A, 162B of the driving gear 162, the number of teeth 163A of the reel gear 163, and the diameter of the reel 164. According to one embodiment, if two full turns comprises a number of turns of the actuator 107 deemed to be satisfactory by a clinician to achieve deflection of the distal tip of the catheter, the design parameters can be selected to achieve this design goal.

In another embodiment (not shown), the handle 106 may be modified such that the reel gear 163 and the reel 164 attached thereto translate in addition to rotate as described in U.S. Pat. No. 10,188,833, herein incorporated by reference in its entirety. Translation of the reel tensions the pull wire 152, and thus a travel distance of the pull wire 152 comprises a combination of a linear travel of the reel and an amount of winding or unwinding due to rotation of the reel.

The handle 106 includes a seal tube 109 disposed therein that is attached to a proximal end 114 of the outer shaft 112. An overmould 109A may be utilized to sealingly attach a distal end of the seal tube 109 to the proximal end 114 of the outer shaft 112. A proximal end of the seal tube 109 is coupled to the bifurcated luer 105 via a snap-fit connection 103 for ease of manufacture. As previously described, the bifurcated luer 105 may be connected to a source of inflation fluid. Bifurcated luer 105 has an inflation port 105B configured to receive inflation fluid, the inflation port 105B being in fluid communication with the inflation lumen of the balloon catheter 102, which corresponds to the central lumen 120 of the outer shaft 112. In an embodiment, the bifurcated luer 105 of the handle 106 further includes a guidewire entry port 105A configurated to slidingly receive a guidewire therethrough, the guidewire entry port 105A being in fluid communication with the guidewire lumen 140 of the balloon catheter 102.

Figure 15B:
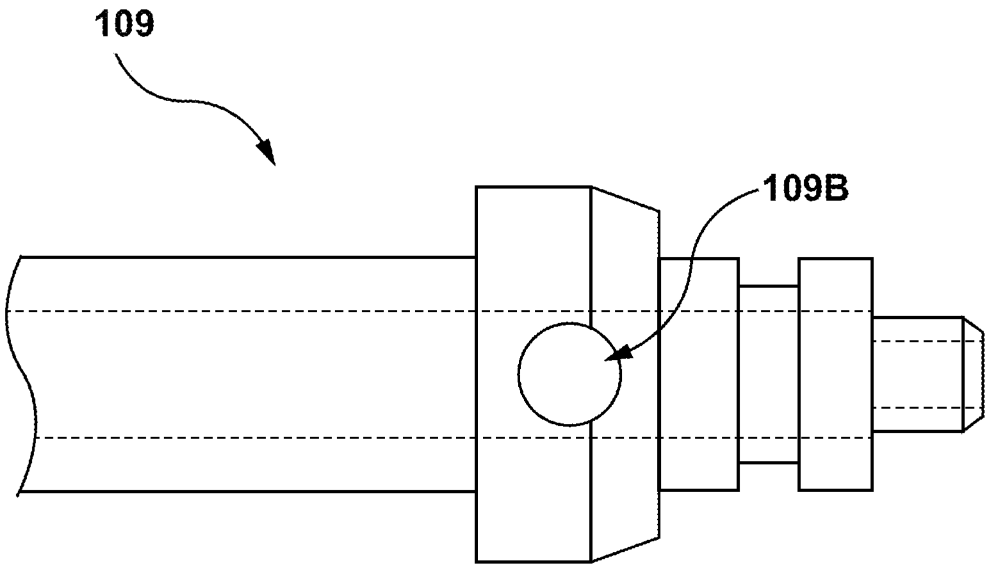
FIG. 15B is an enlarged perspective view of a portion of a seal tube of the handle of FIG. 15.

As shown on FIG. 15B, which is an enlarged perspective view of the proximal end of the seal tube 109 removed from the handle 106 for illustrative purposes, the seal tube 109 includes an opening or hole 109B formed through the sidewall thereof. The opening or hole 109B is sized or configured to receive or interface with a peg (not shown) extending radially inward from the housing of the handle 106. The opening or hole 109B functions to absorb any axial or torsional loads that may transfer between the handle 106 and the outer shaft 112 in order to avoid such loads acting at the snap-fit connection 103 between the seal tube 109 and the bifurcated luer 105. It is desirable to avoid any loads acting at the snap-fit connection 103 between the seal tube 109 and the bifurcated luer 105 in order to avoid comprising the seal of the bifurcated luer 105, which is typically provided via an O-ring within the bifurcated luer 105.

The handle 106 further includes a steering indicator 165 that displays to the user an amount or degree of bending of the elongate tubular body 118 of the outer shaft 112. As best shown on FIGS. 17 and 18, the steering indicator 165 includes a transparent tube 166 disposed over a distal end 155 of the slider 158. The distal end 155 of the slider 158 extends distally beyond the actuator 107 of the handle 106 to be visible to a user within the transparent tube 166. The longitudinal position of the distal end 155 of the slider 158 within the transparent tube 166 corresponds to the amount of bending of the elongate tubular body 118 of the outer shaft 112, and thus alerts to the user to how much steering is engaged or left in the delivery system at any given time. The transparent tube 166 is disposed at a distal end of the handle 106, and permits 360 degree visibility of the distal end 155 of the slider 158 disposed therein so that the user may easily see how much the steering mechanism within the handle 106 has been engaged. 360 degree visibility is an important feature because the distal end 155 of the slider 158 is visible to the user at any angle of rotation if the delivery system 100 (and handle 106 thereon) is torqued.

In an embodiment, teeth 168 may be machined onto the distal end 155 of the slider 158. Teeth 168 are configured to provide haptic feedback to a user when the maximum amount of steering or bending permitted by the delivery system 100 is reached. More particularly, when the maximum amount of steering or bending permitted by the delivery system 100 is reached, the teeth 168 on the slider 158 engage with teeth 167 formed on an inner surface of the transparent tube 166 and the engagement may be felt and heard (i.e., a rumbling noise may be emitted) by the user.

Figure 19:
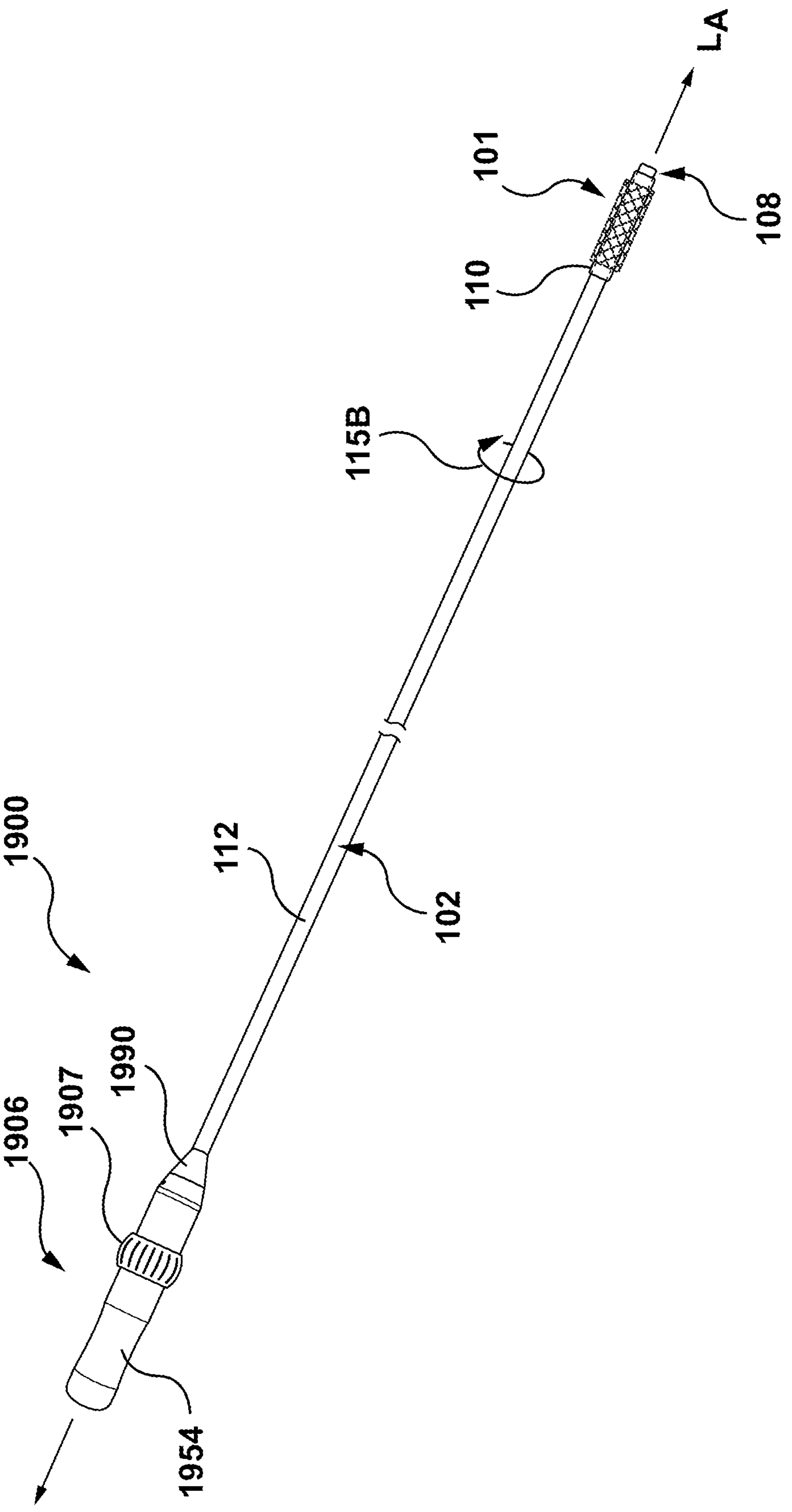
FIG. 19 is a side view of a delivery system according to another embodiment hereof, wherein the delivery system includes an outer shaft configured for improved torque transmission and the delivery system also includes a balloon-expandable prosthesis disposed at a distal portion thereof in its unexpanded configuration, and wherein the delivery system includes a handle including both a torqueing mechanism and a steering mechanism.
Figure 20:
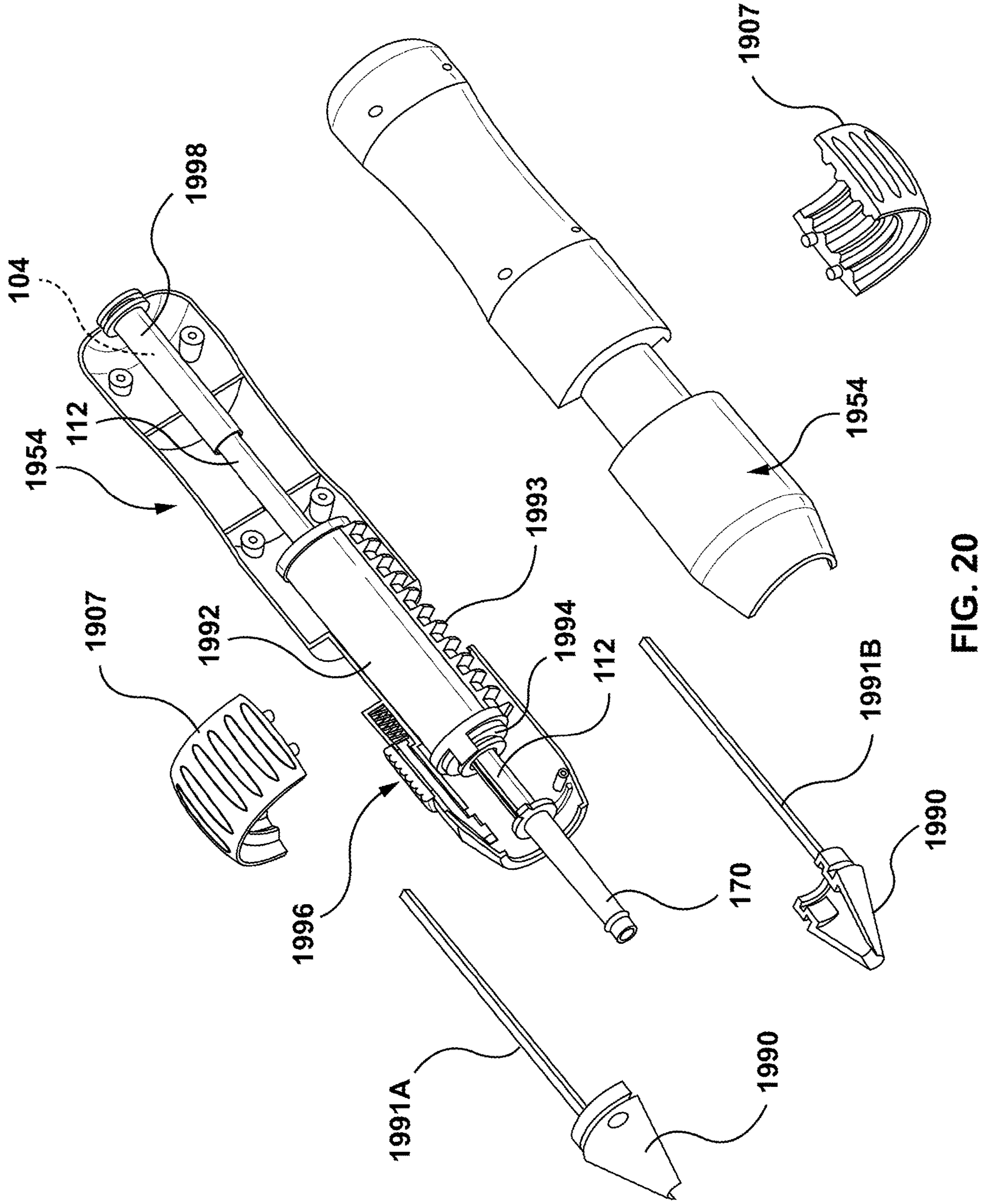
FIG. 20 is an exploded perspective view of the handle of the delivery system of FIG. 19.
Figure 21:
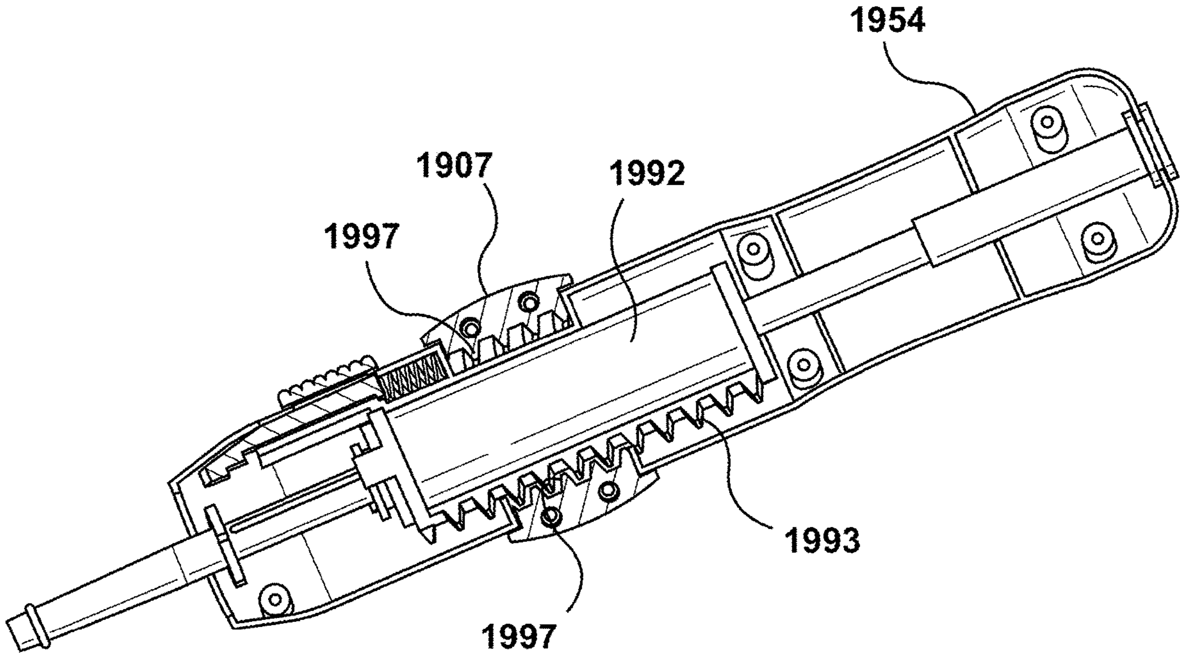
FIG. 21 is a sectional view of the handle of the delivery system of FIG. 19.

As previously stated, when it is desired to rotate or torque the balloon catheter 102, the balloon catheter 102 is rotated by rotation of the handle 106. However, in another embodiment hereof, the handle may include another actuator for rotating the balloon catheter 102. More particularly, FIGS. 19-21 illustrate another embodiment hereof in which an alternative handle 1906 is utilized with the balloon catheter 102. The handle 1906 includes a housing or shell 1954 which houses the internal components of the handle 1906. FIG. 20 is an exploded perspective view of the handle 1906, and FIG. 21 is a cross-sectional view of the handle 1906. In addition to the housing 1954, the handle 1906 includes the nosecone 1990 which is rotatable relative to the housing 1954, a bearing 1994 which is disposed within the housing 1954 and is concentrically disposed over the outer shaft 112, a rack 1992 coupled to the bearing 1994, a locking mechanism 1996, the strain relief component 170 disposed over a portion of the outer shaft 112 at a distal end of the housing 1954, and a luer 1998 disposed over a portion of the shaft 102 at a proximal end of the housing 1954. In an embodiment, the luer 1998 is attached to the housing 1954 and the outer shaft 112 is disposed through the luer 1998 such that the outer shaft 112 is configured to freely rotate or spin within the luer 1998 and thus be rotatable relative to the housing 1954. In another embodiment, the outer shaft 112 is attached or fixed relative to the luer 1998 and the luer 1998 is coupled to the housing such that it can freely rotate or spin relative thereto.

The rack 1992 is a tubular component defining a lumen therethrough such that the outer shaft 112 extends through the rack 1992. The rack 1992 includes a series of protrusions 1993 formed on an outer surface thereof for interacting with the knob 1907. More particularly, the knob 1907 is accessible and operable from an exterior of the housing 1954. The knob 1907 is concentrically disposed over the rack 1992 as best shown in FIG. 21. The knob 1907 includes a thread 1997 on an inner surface thereof that is configured to mate with or engage the series of protrusions 1993 formed on the outer surface of the rack 1992. Stated another way, the threaded inner surface of the knob 1907 is threadedly engaged with the outer surface of the rack 1992.

The nosecone 1990 includes first and second fingers 1991A, 1991B proximally extending from the proximal end surface of the nosecone 1990. The first and second fingers 1991A, 1991B are disposed at circumferentially opposing locations of the nosecone 1990, and serve to couple the nosecone 1990 to the bearing 1994.

The handle 1906 includes both a torqueing mechanism and a steering mechanism which are integrated into the handle 1906 such that operation of the torqueing mechanism does not interfere with operation of the steering mechanism and operation of the steering mechanism does not interfere with operation of the torqueing mechanism. The steering mechanism, which is operable to tension the pull wire 152, is actuated by rotation of the knob 1907. The torqueing mechanism, which is operable to rotate or torque the balloon catheter 102, is actuated by rotation of the nosecone 1990. The torqueing mechanism permits the distal portion 108 of the balloon catheter 102 to be rotated or torqued by turning the nosecone 1990 disposed at the distal end of the handle 1906 while holding the proximal end of the handle 1906 which contains the remaining controls. The torqueing mechanism includes the nosecone 1990 and the bearing 1994, which are rotatably coupled together such that rotation of the nosecone 1990 also results in rotation of the bearing 1994. The bearing 1994 is also rotatably coupled to the outer shaft 112 such that rotation of the bearing 1994, which is concentrically disposed over the outer shaft 112, further results in rotation of the outer shaft 112. Stated another way, the outer surface of the outer shaft 112 is in sufficient contact with the inner surface of the bearing 1994 such that the outer shaft 112 rotates with the bearing 1994. Thus, the torqueing mechanism permits the distal portion 108 of the balloon catheter 102 to be rotated by turning a nosecone 1990 of the handle 1906. In another embodiment, the bearing 1994 may be a roller-type or ball spline bearing, or other bearing known in the art, that transmits torque to a shaft and also permits axial movement relative to the shaft.

When the steering mechanism is actuated via rotation of the knob 1907, the rack 1992 and the bearing 1994 coupled thereto move axially or longitudinally relative to the outer shaft 112 and the nosecone 1990 without interfering with the torqueing mechanism. When the torqueing mechanism is actuated via rotation of the nosecone 1990, the bearing 1994 rotates the outer shaft 112 and rotates relative to or spins freely within the rack 1992 without interfering with the steering mechanism. The pull wire 152 attached at its proximal end to the bearing 1994 rotates to the same degree as the outer shaft 112 when the balloon catheter 102 is being torqued via rotation of the nosecone 1990. The handle 1906 and operation thereof is further described in more detail in U.S. patent application Ser. No. 16/907,466, filed Jun. 22, 2020, previously incorporated by reference in its entirety and assigned to the same assignee as the present disclosure.

Figure 22:
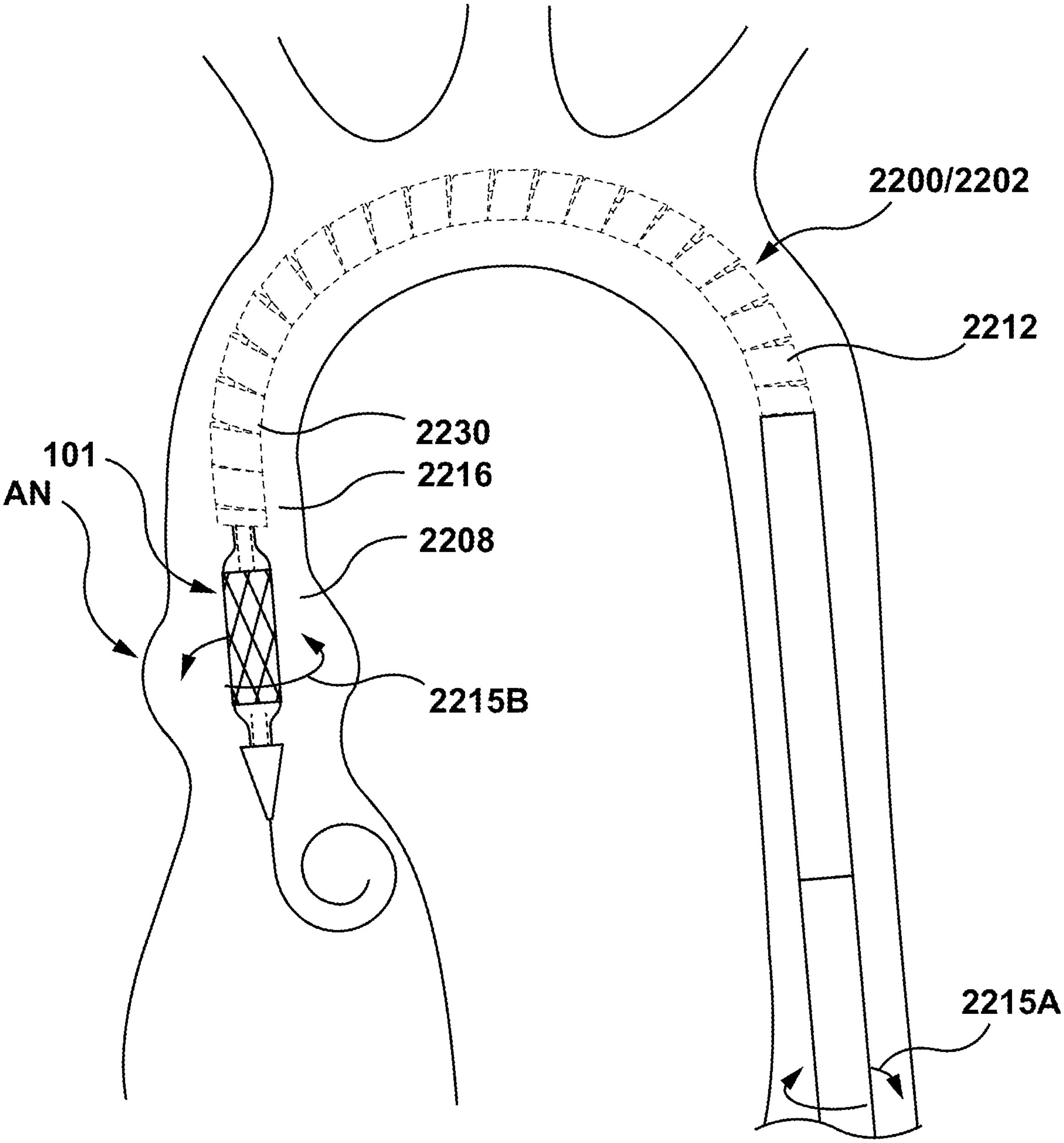
FIG. 22 is a sectional view of a delivery system according to another embodiment hereof being delivered in situ to a treatment site, wherein the delivery system includes an outer shaft configured for improved torque transmission and the delivery system also includes a balloon-expandable prosthesis disposed at a distal portion thereof in its unexpanded configuration, and wherein the outer shaft includes a tubular braid component and a hypotube overlapping the full length of the tubular braid component.

Turning now to FIG. 22, another embodiment of an outer shaft 2212 is shown that may be utilized as the outer shaft of a balloon catheter 2202 of a delivery system 2200. In the embodiment of FIG. 22, the balloon catheter 2202 is the same as the balloon catheter 102 described above except for the construction of the outer shaft 2212. As such, the other components of the balloon catheter 2202 are not described herein. The configuration of the outer shaft 2212 greatly improves the torsional strength of the balloon catheter 2202 so that rotational force applied at a proximal portion (not shown on FIG. 22) of the balloon catheter 2202 may be transferred to a distal portion 2208 of the balloon catheter 2202, which includes the balloon-expandable prosthesis 101. This increase in torsional strength is provided without any substantial decrease in the deflection capability of the distal portion 2208 of the balloon catheter 2202. The outer shaft 2212 of the balloon catheter 2202 has a high torsional stiffness and is configured for improved torque transmission such that torque or rotation at or near a proximal end 2214 of the outer shaft 2212 (represented by directional arrow 2215A) exhibits a highly sensitive and functional response ratio compared to rotation or torque of the distal portion 2208 of the balloon catheter 2202 (represented by directional arrow 2215*b*) when the outer shaft 2212 is rotated 360 degrees, even when the delivery system 100 is in a bent or curved position as shown in FIGS. 3 and 4 above. The outer shaft 2212, and effectively the balloon catheter 2202 and the balloon-expandable prosthesis 101 mounted thereon, is thus operable to be rotated 360 degrees without kinking or building up recoil or tension in the outer shaft 2212 when the outer shaft 2212 is rotated. As such, the outer shaft 2212 is configured to result in improved circumferential positioning of the balloon-expandable prosthesis 101 in situ to avoid blocking the ostia of the coronary arteries and/or to align commissures of the balloon-expandable prosthesis 101 with the native valve commissures as described above.

Figure 23:
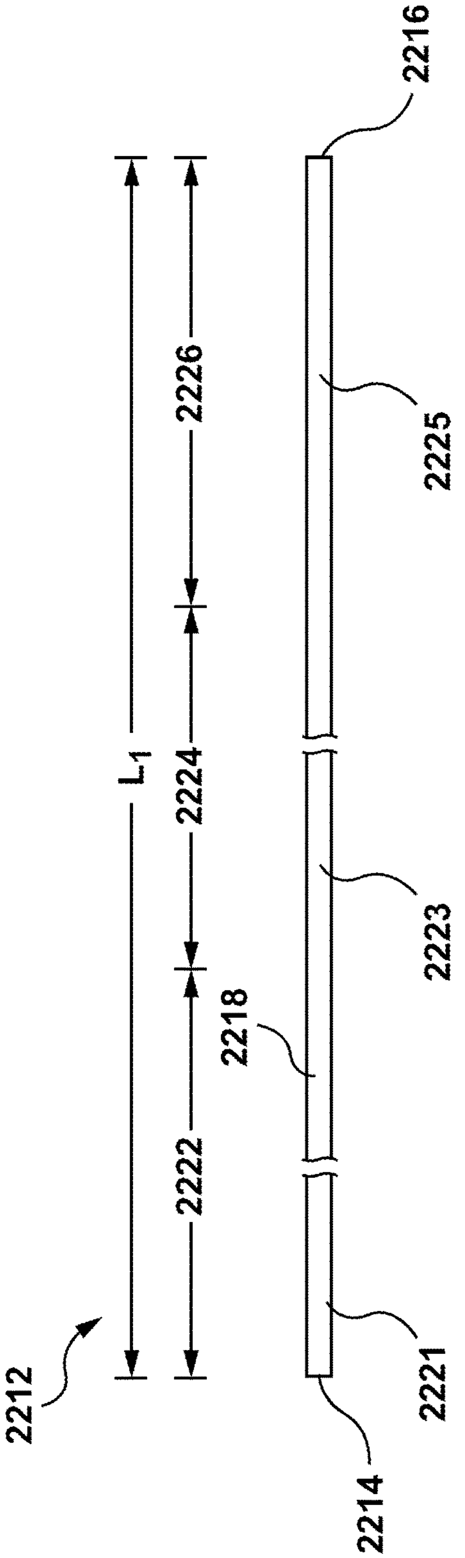
FIG. 23 is a side illustrative view of the outer shaft of the delivery system of FIG. 22, wherein the outer shaft is removed from the delivery system for sake of illustration only.

As shown in the side view of FIG. 23, which is a side view of the outer shaft 2212 removed from the balloon catheter 2202 for sake of illustration only, an elongated tubular body 2218 of the outer shaft 2212 has a length L1 from the proximal end 2214 to a distal end 2216 thereof. For illustrative purposes only, the elongate tubular body 2218 of the outer shaft 2212 is described herein as having three longitudinal portions, i.e., a proximal portion 2222, a distal portion 2226, and an intermediate portion 2224 extending between the proximal portion 2222 and the distal portion 2226. The portions 2222, 2224, 2226 are integral or continuous portions of the elongate tubular body 2218 but have different constructions as described herein. In an embodiment, the proximal portion 2222 extends between 75-90% of the length L1 of the elongated tubular body 2218, the intermediate portion extends 2224 between 5-10% of the length L1 of the elongated tubular body 2218, and the distal portion 2226 extends between 5-15% of the length L1 of the elongated tubular body 2218. In an embodiment, the proximal portion 2222 extends between 82-86% of the length L1 of the elongated tubular body 2218, the intermediate portion extends 2224 between 6-8% of the length L1 of the elongated tubular body 2218, and the distal portion 2226 extends between 8-10% of the length L1 of the elongated tubular body 2218. The respective lengths of portions 2222, 2224, and 2226 are configured to correspond to arc lengths within the anatomy through which the delivery system 100 is tracked, i.e., arc lengths within the aortic arch. In an embodiment, the elongated tubular body 2218 has an outer diameter that is constant along the length L1. In another embodiment (not shown), the elongated tubular body 2218 has a first outer diameter that is constant along the proximal portion 2222 and a second outer diameter that is constant along the intermediate portion 2224 and the distal portion 2226, the first outer diameter being greater than the second outer diameter.

The proximal portion 2222 of the elongate tubular body 2218 of the outer shaft 2212 includes a first polymer 2221 having a first stiffness. The intermediate portion 2224 of the elongate tubular body 2218 of the outer shaft 2212 includes a second polymer 2223 having a second stiffness. The distal portion 2226 of the elongate tubular body 2218 of the outer shaft 2212 includes a third polymer 2225 having a third stiffness. The second stiffness of the second polymer 2223 is less than the first stiffness of the first polymer 2221 and the third stiffness of the third polymer 2225 is less than the second stiffness of the second polymer 2223. The portions 2222, 2224, 2226 may be formed of one or more polymeric materials including polyamide family members or polyethylene of varying molecular weights. In an embodiment, the first polymer 2221 is VESTAMID® ML24, the second polymer 2223 is PEBAX® 63D, and the third polymer 2225 is PEBAX® 35D.

Similar to the outer shaft 112, the outer shaft 2212 includes a tubular braid component 2228 that extends the entire length L1 of the outer shaft 2212, from the proximal end 2214 to the distal end 2216 thereof. Stated another way, a length of the tubular braid component 2228 is the same as or substantially the same as the length L1 of the elongate tubular body 2218 of the outer shaft 2212. The tubular braid component 2228 is the same as the tubular braid component 128 described above, and thus the details of the construction of the tubular braid component 2228 will not be repeated. The proximal portion 2222 of the elongate tubular body 2218 of the outer shaft 2212 includes the tubular braid component 2228 extending within the first polymer 2221, the intermediate portion 2224 of the elongate tubular body 2218 of the outer shaft 2212 includes the tubular braid component 2228 extending within the second polymer 2223, and the distal portion 2226 of the elongate tubular body 2218 of the outer shaft 2212 includes the tubular braid component 2228 extending within the third polymer 2225.

Figure 24B:
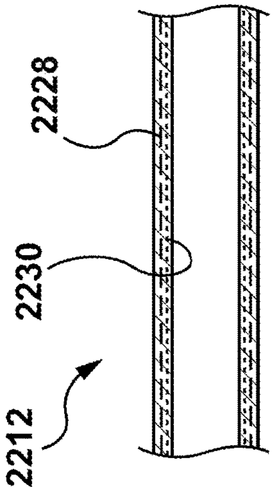
FIG. 24B is a sectional view of FIG. 23 according to an alternative embodiment hereof.
Figure 24A:
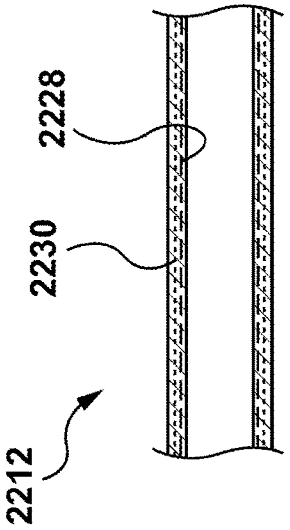
FIG. 24A is a sectional view of FIG. 23.

In addition to the tubular braid component 2228, the outer shaft 2212 includes a hypotube 2230 that extends the entire length L1 of the outer shaft 2212, from the proximal end 2214 to the distal end 2216 thereof. Stated another way, a length of the hypotube 2230 is the same as or substantially the same as the length L1 of the elongate tubular body 2218 of the outer shaft 2212. The hypotube 2230 is a tubular component configured for elastic deformation. In some embodiments, the hypotube 2230 is a Nitinol super elastic material. In another embodiment, the hypotube 2230 is formed from stainless steel and the geometry of the hypotube 2230 (i.e., a cut pattern described below) configures the hypotube 2230 for elastic deformation. The hypotube 2230 includes a sidewall having a cut pattern which may be any cut pattern described above with respect to FIGS. 10A-10E. The cut pattern is configured so as to not create a significant directional bias or limit the degrees of freedom. The tubular braid component 2228 and the hypotube 2230 overlap each other along the length L1 of the elongate tubular body 2218 of the outer shaft 2212. More particularly, the tubular braid component 2228 overlaps the hypotube 2230 as shown in FIG. 24A, or the hypotube 2230 overlaps the tubular braid component 2228 as shown in FIG. 24B, such that the full or entire length L1 of the outer shaft 2212 includes both the tubular braid component 2228 and the hypotube 2230. Stated another way, the hypotube 2230 may be disposed or incorporated either under or over the tubular braid component 2228.

The hypotube 2230 is disposed along the entire length of the outer shaft 2212 in order to improve torsional performance while still maintaining local flexibility due to the laser cut pattern of the hypotube 2230. The hypotube 2230 is reflowed with the first, second, and third polymers 2221, 2223, 2225, respectively, to facilitate flexibility, because the flexible polymers fill the voids formed by the laser cut pattern of the hypotube 2230. In an embodiment, the first, second, and third polymers 2221, 2223, 2225, respectively, extend through the voids formed by the laser cut pattern of the hypotube 2230 as well as through the spaces between woven ribbon wires of the tubular braid component 2228. The first, second, and third polymers 2221, 2223, 2225, respectively, may be reflowed during manufacture to allow the polymeric material to pass through the voids formed by the laser cut pattern of the hypotube 2230 as well as through the spaces of the tubular braid component 2228. The tubular braid component 2228 has a distal end that longitudinally terminates distal to the distal end of the hypotube 2230.

The stiffness of the proximal portion 2222 of the outer shaft 2212 which includes the first polymer 2221, the tubular braid component 2228, and the hypotube 2230, is constant along a length thereof unless the cut pattern of the hypotube 2230 is configured to have variable flexibility along a length thereof. Similarly, the stiffness of the intermediate portion 2224 of the outer shaft 2212 which includes the second polymer 2223, the tubular braid component 2228, and the hypotube 2230, is constant along a length thereof unless the cut pattern of the hypotube 2230 is configured to have variable flexibility along a length thereof. Similarly, the stiffness of the distal portion 2226 of the outer shaft 2212 which includes the third polymer 2225, the tubular braid component 2228, and the hypotube 2230, is constant along a length thereof unless the cut pattern of the hypotube 2230 is configured to have variable flexibility along a length thereof. For example, in an embodiment, the distal portion 2226 may include a cut pattern similar to that shown in FIG.

10E described above in which the stiffness of the hypotube 2230 decreases in a distal direction along the length of the hypotube 2230.

Figure 25:
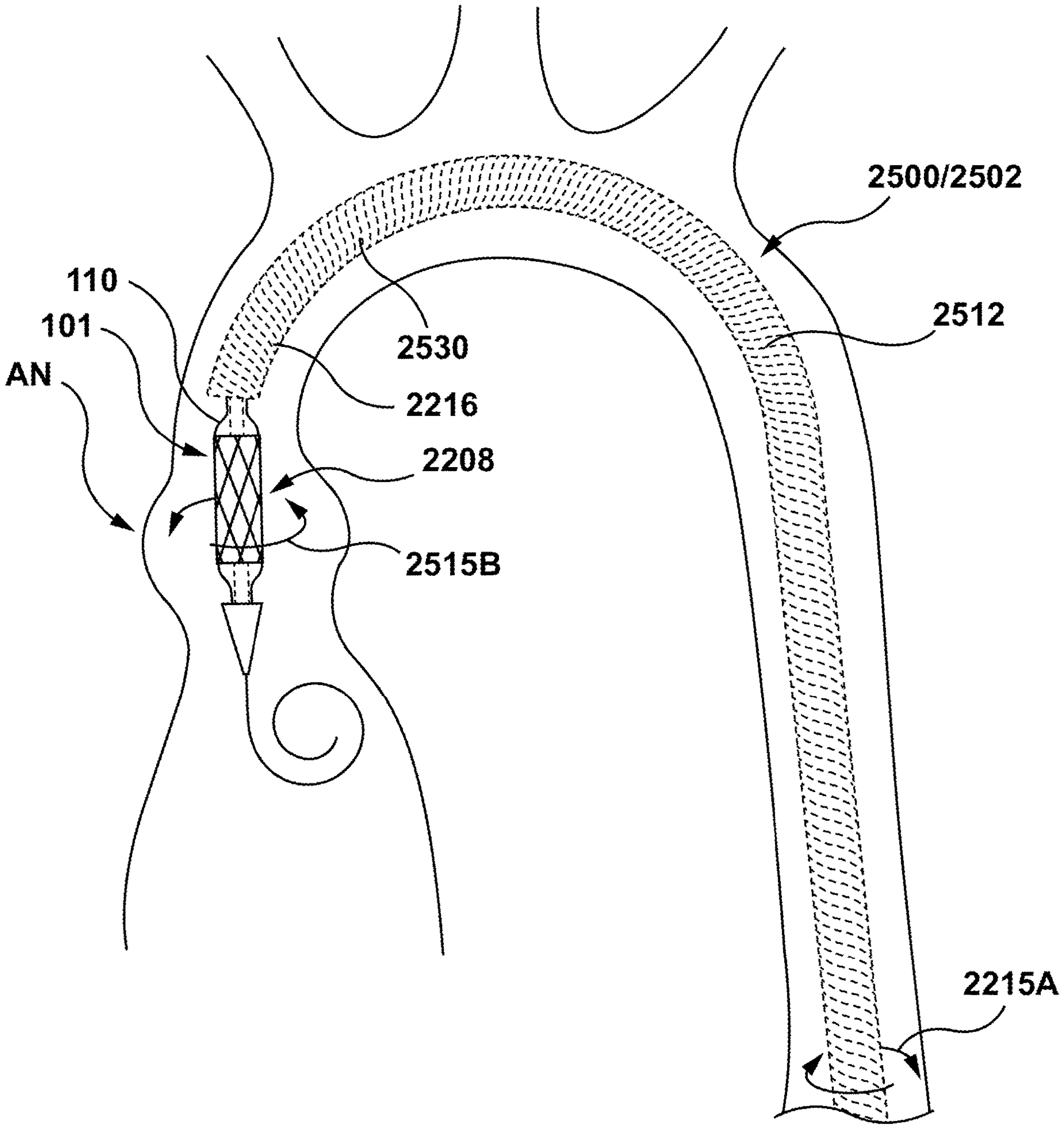
FIG. 25 is a sectional view of a delivery system according to another embodiment hereof being delivered in situ to a treatment site, wherein the delivery system includes an outer shaft configured for improved torque transmission and the delivery system also includes a balloon-expandable prosthesis disposed at a distal portion thereof in its unexpanded configuration, and wherein the outer shaft includes a tubular braid component and a helical hollow strand overlapping the full length of the tubular braid component.

Turning now to FIG. 25, another embodiment of an outer shaft 2512 is shown that may be utilized as the outer shaft of a balloon catheter 2502 of a delivery system 2500. In the embodiment of FIG. 25, the balloon catheter 2502 is the same as the balloon catheter 102 described above except for the construction of the outer shaft 2512. As such, the other components of the balloon catheter 2502 are not described herein. The configuration of the outer shaft 2512 greatly improves the torsional strength of the balloon catheter 2502 so that rotational force applied at a proximal portion (not shown on FIG. 25) of the balloon catheter 2502 may be transferred to a distal portion 2508 of the balloon catheter 2502, which includes the balloon-expandable prosthesis 101. This increase in torsional strength is provided without any substantial decrease in the deflection capability of the distal portion 2508 of the balloon catheter 2502. The outer shaft 2512 of the balloon catheter 2502 has a high torsional stiffness and is configured for improved torque transmission such that torque or rotation at or near a proximal end 2514 of the outer shaft 2512 (represented by directional arrow 2515A) exhibits a highly sensitive and functional response ratio compared to rotation or torque of the distal portion 2508 of the balloon catheter 2502 (represented by directional arrow 2515*b*) when the outer shaft 2512 is rotated 360 degrees, even when the delivery system 100 is in a bent or curved position as shown in FIGS. 3 and 4 above. The outer shaft 2512, and effectively the balloon catheter 2502 and the balloon-expandable prosthesis 101 mounted thereon, is thus operable to be rotated 360 degrees without kinking or building up recoil or tension in the outer shaft 2512 when the outer shaft 2512 is rotated. As such, the outer shaft 2512 is configured to result in improved circumferential positioning of the balloon-expandable prosthesis 101 in situ to avoid blocking the ostia of the coronary arteries and/or to align commissures of the balloon-expandable prosthesis 101 with the native valve commissures as described above.

Figure 26:
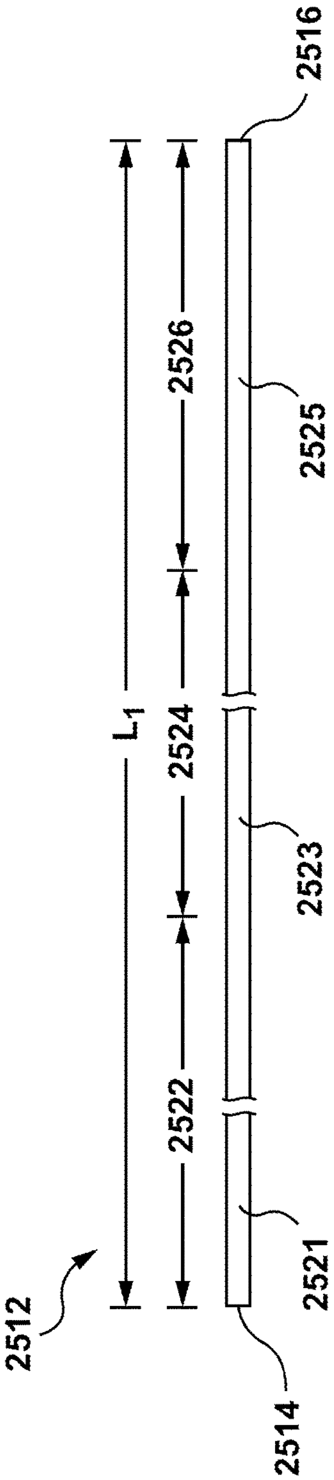
FIG. 26 is a side illustrative view of the outer shaft of the delivery system of FIG. 25, wherein the outer shaft is removed from the delivery system for sake of illustration only.

As shown in the side view of FIG. 26, which is a side view of the outer shaft 2512 removed from the balloon catheter 2502 for sake of illustration only, an elongated tubular body 2518 of the outer shaft 2512 has a length L1 from the proximal end 2514 to a distal end 2516 thereof. For illustrative purposes only, the elongate tubular body 2518 of the outer shaft 2512 is described herein as having three longitudinal portions, i.e., a proximal portion 2525, a distal portion 2526, and an intermediate portion 2524 extending between the proximal portion 2525 and the distal portion 2526. The portions 2525, 2524, 2526 are integral or continuous portions of the elongate tubular body 2518 but have different constructions as described herein. In an embodiment, the proximal portion 2525 extends between 75-90% of the length L1 of the elongated tubular body 2518, the intermediate portion extends 2524 between 5-10% of the length L1 of the elongated tubular body 2518, and the distal portion 2526 extends between 5-15% of the length L1 of the elongated tubular body 2518. In an embodiment, the proximal portion 2522 extends between 82-86% of the length L1 of the elongated tubular body 2518, the intermediate portion extends 2524 between 6-8% of the length L1 of the elongated tubular body 2518, and the distal portion 2526 extends between 8-10% of the length L1 of the elongated tubular body 2518. The respective lengths of portions 2522, 2524, and 2526 are configured to correspond to arc lengths within the anatomy through which the delivery system 100 is tracked, i.e., arc lengths within the aortic arch. In an embodiment, the elongated tubular body 2518 has an outer diameter that is constant along the length L1. In another embodiment (not shown), the elongated tubular body 2518 has a first outer diameter that is constant along the proximal portion 2525 and a second outer diameter that is constant along the intermediate portion 2524 and the distal portion 2516, the first outer diameter being greater than the second outer diameter.

The proximal portion 2525 of the elongate tubular body 2518 of the outer shaft 2512 includes a first polymer 2521 having a first stiffness. The intermediate portion 2524 of the elongate tubular body 2518 of the outer shaft 2512 includes a second polymer 2523 having a second stiffness. The distal portion 2526 of the elongate tubular body 2518 of the outer shaft 2512 includes a third polymer 2525 having a third stiffness. The second stiffness of the second polymer 2523 is less than the first stiffness of the first polymer 2521 and the third stiffness of the third polymer 2525 is less than the second stiffness of the second polymer 2523. The portions 2522, 2524, 2526 may be formed of one or more polymeric materials including polyamide family members or polyethylene of varying molecular weights. In an embodiment, the first polymer 2521 is VESTAMID® ML24, the second polymer 2523 is PEBAX® 63D, and the third polymer 2525 is PEBAX® 35D.

Similar to the outer shaft 112, the outer shaft 2512 includes a tubular braid component 2528 that extends the entire length L1 of the outer shaft 2512, from the proximal end 2514 to the distal end 2516 thereof. Stated another way, a length of the tubular braid component 2528 is the same as or substantially the same as the length L1 of the elongate tubular body 2518 of the outer shaft 2512. The tubular braid component 2528 is the same as the tubular braid component 128 described above, and thus the details of the construction of the tubular braid component 2528 will not be repeated. The proximal portion 2525 of the elongate tubular body 2518 of the outer shaft 2512 includes the tubular braid component 2528 extending within the first polymer 2521, the intermediate portion 2524 of the elongate tubular body 2518 of the outer shaft 2512 includes the tubular braid component 2528 extending within the second polymer 2523, and the distal portion 2526 of the elongate tubular body 2518 of the outer shaft 2512 includes the tubular braid component 2528 extending within the third polymer 2525.

Figure 28A:
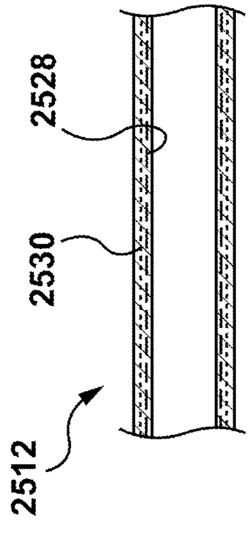
FIG. 28A is a sectional view of FIG. 26.
Figure 28B:
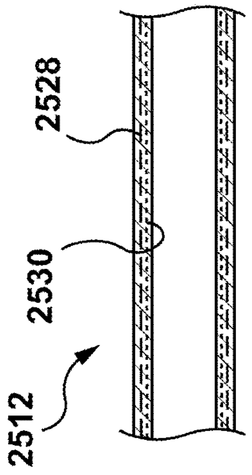
FIG. 28B is a sectional view of FIG. 26 according to an alternative embodiment hereof.

In addition to the tubular braid component 2528, the outer shaft 2512 includes a helical hollow strand 2530 that extends the entire length L1 of the outer shaft 2512, from the proximal end 2514 to the distal end 2516 thereof. Stated another way, a length of the helical hollow strand 2530 is the same as or substantially the same as the length L1 of the elongate tubular body 2518 of the outer shaft 2512. The tubular braid component 2528 and the helical hollow strand 2530 overlap each other along the length L1 of the elongate tubular body 2518 of the outer shaft 2512. More particularly, the tubular braid component 2528 overlaps the helical hollow strand 2530 as shown in FIG. 28A, or the helical hollow strand 2530 overlaps the tubular braid component 2528 as shown in FIG. 28B, such that the full or entire length L1 of the outer shaft 2512 includes both the tubular braid component 2528 and the helical hollow strand 2530. Stated another way, the helical hollow strand 2530 may be disposed or incorporated either under or over the tubular braid component 2528.

Figure 27:
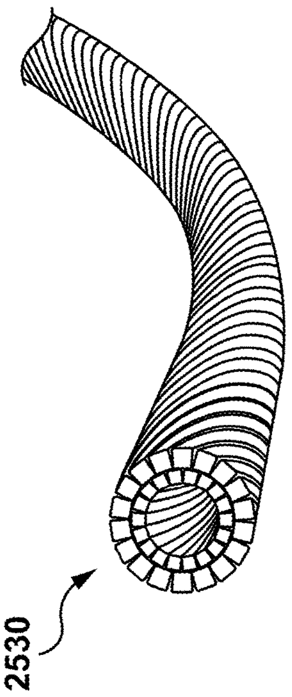
FIG. 27 is a perspective view of the helical hollow strand of FIG. 25, wherein the helical hollow strand is removed from the outer shaft for sake of illustration only.

The helical hollow strand 2530 is disposed along the entire length of the outer shaft 2512 in order to improve torsional performance while still maintaining local flexibility. A perspective view of a portion of the helical hollow strand 2530 is shown in FIG. 27 removed from the outer shaft 2512 for sake of illustration only. Helical hollow strands or tubes are commerically available components that may be configured to achieve desired flexibility due to various factors include wire size, filar wire count, and the frequency of welds between windings. The helical hollow strand 2530 is reflowed with the first, second, and third polymers 2521, 2523, 2525, respectively, to facilitate flexibility, because the flexible polymers fill the voids between the windings of the helical hollow strand 2530. In an embodiment, the first, second, and third polymers 2521, 2523, 2525, respectively, extend between the windings of the helical hollow strand 2530 as well as through the spaces between woven ribbon wires of the tubular braid component 2228. The first, second, and third polymers 2521, 2523, 2525, respectively, may be reflowed during manufacture to allow the polymeric material to between the windings of the helical hollow strand 2530 as well as through the spaces of the tubular braid component 2528. The tubular braid component 2528 has a distal end that longitudinally terminates distal to the distal end of the helical hollow strand 2530.

The stiffness of the proximal portion 2525 of the outer shaft 2512 which includes the first polymer 2521, the tubular braid component 2528, and the helical hollow strand 2530, is constant along a length thereof unless the windings pattern of the helical hollow strand 2530 is configured to have variable flexibility along a length thereof. Similarly, the stiffness of the intermediate portion 2524 of the outer shaft 2512 which includes the second polymer 2523, the tubular braid component 2528, and the helical hollow strand 2530, is constant along a length thereof unless the windings pattern of the helical hollow strand 2530 is configured to have variable flexibility along a length thereof. Similarly, the stiffness of the distal portion 2526 of the outer shaft 2512 which includes the third polymer 2525, the tubular braid component 2528, and the helical hollow strand 2530, is constant along a length thereof unless the windings pattern of the helical hollow strand 2530 is configured to have variable flexibility along a length thereof.

FIG. 29 and FIG. 30 illustrate side perspective and end views, respectively, of a transcatheter valve prosthesis 2901 that may be utilized as the balloon-expandable prosthesis 101 according to an embodiment hereof. The configuration of the transcatheter prosthesis 2901 is merely exemplary and it is understood that the balloon-expandable prostheses 101 may have any number of alternative configurations and can be used with the delivery devices and methods described herein. In another embodiment hereof, the balloon-expandable prosthesis 101 may have any configuration described in described in co-pending U.S. patent application Ser. No. 16/778,688 to Peterson et al., which is assigned to the same assignee as the present disclosure and which is herein incorporated by reference in its entirety. In addition, although the transcatheter valve prosthesis 2901 is a valve prosthesis, the delivery devices described herein may also be used with other balloon-expandable prostheses such as stent-graft prostheses, uncovered stents, bare metal stents, drug eluting stents, and any balloon-expandable structure.

Transcatheter valve prosthesis 2901 includes a radially-expandable stent 2911 and a prosthetic valve 2919. FIG. 29 is a side view of the transcatheter valve prosthesis 2901 in the expanded configuration, while FIG. 30 is an end view illustration of the transcatheter valve prosthesis 2901 to show to the prosthetic valve 2919 disposed within the stent 2911. When the transcatheter valve prosthesis 2901 is deployed within the valve annulus of a native heart valve, the stent 2911 of the transcatheter valve prosthesis 2901 is configured to be radially expanded within native valve leaflets of the patient's defective valve, to thereby retain the native valve leaflets in a permanently open state. In embodiments hereof, the transcatheter valve prosthesis 2901 is configured for replacement for an aortic valve such that an inflow end 2913A of the transcatheter valve prosthesis 2901 extends into and anchors within the aortic annulus of a patient's left ventricle, while an outflow end 2913B of the transcatheter valve prosthesis 2901 is positioned within the aortic sinuses.

The stent 2911 of the transcatheter valve prosthesis 2901 is a unitary frame or scaffold that supports the prosthetic valve 2919 including one or more valve leaflets 2919A, 2919B, 2919C within the interior of the stent 2911. The prosthetic valve 2919 is capable of blocking flow in one direction to regulate flow there-through via the valve leaflets 2919A, 2919B, 2919C that may form a bicuspid or tricuspid replacement valve. FIG. 30 is an end view of FIG. 29 taken from the outflow end 2913B of the prosthesis and illustrates an exemplary tricuspid valve having three valve leaflets 2919A, 2919B, 2919C, although a bicuspid leaflet configuration may alternatively be used in embodiments hereof More particularly, as the transcatheter valve prosthesis 2901 is configured for placement within a native aortic valve having three leaflets, the prosthetic valve 2919 may include three valve leaflets 2919A, 2919B, 2919C. However, the transcatheter valve prosthesis 2901 is not required to have the same number of leaflets as the native valve. If the transcatheter valve prosthesis 2901 is alternatively configured for placement within a native valve having two leaflets such as the mitral valve, the prosthetic valve 2919 may include two or three valve leaflets. The valve leaflets 2919A, 2919B, 2919C may be attached to a graft material 2917 which encloses or lines a portion of the stent 2911 as would be known to one of ordinary skill in the art of prosthetic tissue valve construction. The valve leaflets 2919A, 2919B, 2919C are sutured or otherwise securely and sealingly attached along their bases to the interior surface of the graft material 2917, or otherwise attached to the stent 2911. Adjoining pairs of leaflets are attached to one another at their lateral ends to form commissures 2915, with the free edges 2931 of the valve leaflets 2919A, 2919B, 2919C forming coaptation edges that meet in an area of coaptation.

The valve leaflets 2919A, 2919B, 2919C may be made of pericardial material; however, the valve leaflets 2919A, 2919B, 2919C may instead be made of another material. Natural tissue for the valve leaflets 2919A, 2919B, 2919C may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as the valve leaflets 2919A, 2919B, 2919C include DACRON® polyester commercially available from Invista North America S.A.R.L. of Wilmington, DE, other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 2917 may enclose or line the stent 2911 as would be known to one of ordinary skill in the art of prosthetic tissue valve construction. Graft material 2917 may be a natural or biological material such as pericardium or another membranous tissue such as intestinal submucosa. Alternatively, graft material 2917 may be a low-porosity woven fabric, such as polyester, Dacron fabric, or PTFE, which creates a one-way fluid passage when attached to the stent. In one embodiment, graft material 2917 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

As previously stated, the stent 2911 is balloon or mechanically expandable as would be understood by one of ordinary skill in the art. As such, the stent 2911 is made from a plastically deformable material such that when expanded by a dilatation balloon such as the balloon 110 of the balloon catheter 102, the stent 2911 maintains its radially expanded configuration. The stent 2911 may be formed from stainless steel or other suitable metal, such as platinum iridium, cobalt chromium alloys such as MP35N, or various types of polymers or other materials known to those skilled in the art, including said materials coated with various surface deposits to improve clinical functionality. The stent 2911 is configured to be rigid such that it does not deflect or move when subjected to in-vivo forces, or such that deflection or movement is minimized when subjected to in-vivo forces. In an embodiment, the radial stiffness (i.e., a measurement of how much the stent 2911 deflects when subjected to in-vivo forces) of the stent 2911 is between 80 N/m and 120 N/m, and the radial stiffness of the stent 2911 scaled across the deployed height thereof is approximately 5 $N/mm^2$. In an embodiment, the radial stiffness of the stent 2911 is greater than 100 N/m. Further, in an embodiment, the device recoil (i.e., a measurement of how much the stent 2911 relaxes after balloon deployment) is below 15% and the approximately recoil after deployment is between 1 mm and 2 mm. Further, in an embodiment, the device crush or yield (i.e., the radial force at which the stent 2911 yields) is approximately 200 N.

Delivery of the transcatheter valve prosthesis 2901 may be accomplished via a percutaneous transfemoral approach or a transapical approach directly through the apex of the heart via a thoracotomy, or may be positioned within the desired area of the heart via different delivery methods known in the art for accessing heart valves. The transcatheter valve prosthesis 2901 has a crossing profile of between 15-30 Fr, the crossing profile being defined as the outside diameter (OD) of the transcatheter valve prosthesis 2901 after it is crimped onto the balloon 110 and allowed to recoil from the crimping action. During delivery, the transcatheter valve prosthesis 2901 remains compressed until it reaches a target diseased native heart valve, at which time the balloon 110 of the balloon catheter 102 is inflated in order to radially expand the transcatheter valve prosthesis 2901 in situ. The balloon catheter 102 is then removed and the transcatheter valve prosthesis 2901 remains deployed within the native target heart valve.

The stent 2911 will now be described in more detail. The stent 2911 is a tubular component defining a central lumen or passageway, and further defines the inflow or proximal end 2913A and the outflow or distal end 2913B of the transcatheter valve prosthesis 2901. When expanded, a diameter Di of the inflow end 2913A of the stent 2911 is the same as a diameter Do of the outflow end 2913B of the stent 2911. In an embodiment, the diameters Di and Do may range between 18 and 30 mm in order to accommodate dimensions of the native valve anatomy. Stated another way, it may be desirable for the transcatheter valve prosthesis 2901 to be available in varying size increments to accommodate varying diameters or sizes of a patient's native annulus. The stent 2911 may be formed by a laser-cut manufacturing method and/or another conventional stent forming method as would be understood by one of ordinary skill in the art. The cross-section of the stent 2911 may be circular, ellipsoidal, rectangular, hexagonal, square, or other polygonal shape, although at present it is believed that circular or ellipsoidal may be preferable with the transcatheter valve prosthesis 2901 being provided for replacement of an aortic valve. The stent 2911 has an expanded configuration, which is shown in the perspective and side views of FIG. 29, and a non-expanded or crimped configuration (not shown). Non-expanded or crimped configuration as used herein refers to the configuration of the stent 2911 after crimping onto a balloon of a balloon catheter for delivery.

The stent 2911 includes a plurality of crowns 2941 and a plurality of struts 2943 with each crown 2941 being formed between a pair of opposing struts 2943. Each crown 2941 is a curved segment or bend extending between opposing struts 2943. The stent 2911 is tubular, with a plurality of side openings 2945 being defined by the plurality of crowns 2941 and the plurality of struts 2943. In an embodiment, the plurality of side openings 2945 may be diamond-shaped.

An inflow portion is formed proximate to the inflow end 2913A of the stent 2911, and an outflow portion is formed proximate to the outflow end 2913B of the stent 2911. The stent 2911 includes one or more inflow markers 2947 positioned at the inflow portion of the stent 2911 and a first outflow marker 2949 positioned at the outflow portion of the stent 2911. In embodiments, the inflow markers 2947 and the first outflow marker 2949 can be utilized in orientation (e.g., axial/annular alignment, tilt alignment, circumferential (rotational) alignment, etc.) of the transcatheter valve prosthesis 2901, in situ, as discussed in detail below. While the transcatheter valve prosthesis 2901 is described herein as including the one or more inflow markers 2947 and the first outflow marker 2949, one skilled in the art will realize that the transcatheter valve prosthesis 2901 can include additional markers.

In the embodiment, the inflow markers 2947 form a ring of distinct marker points around the circumference of the stent 2911, wherein each distinct marker point is equal distance from the inflow end 2913A. For example, as illustrated in FIG. 29, the inflow markers 2947 can be positioned at the inflow portion of the stent 2911 at every third intersection of a pair of the struts 2943. In another embodiment (not shown), the inflow markers 2947 can be positioned at the inflow portion of the stent 2911 at every other intersection of a pair of the struts 2943. The inflow markers 2947 are circumferentially aligned with each other around a circumference of the stent 2911. One skilled in the art will realize that the stent 2911 may include any number of the inflow markers 2947, which are positioned at any location within the inflow portion. The inflow markers 2947 are preferably located at the lengthwise location of the stent 2911 that is desired to be aligned with the annulus of the native heart valve when the transcatheter valve prosthesis 2901 is deployed at the native heart valve. For example, inflow markers 2947 allows for better depth positioning of the transcatheter valve prosthesis 2901, in a crimped or compressed state, such that it can be more accurately deployed and reduce the incidence rate of permanent pacemaker (PPM) post-implantation.

While FIG. 29 illustrates one example of the positioning and number of inflow markers 2947, one skilled in the art will realize that the stent 2911 can include any number of inflow markers 2947, positioned at any location within the inflow portion thereof. For example, the inflow markers 2947 can be positioned on the struts 2943. Likewise, for example, the inflow markers 2947 can be asymmetrically aligned, circumferentially, around a circumference of the stent 2911, e.g., with different circumferential distances between the inflow markers 2947. Additionally, for example, the inflow markers 2947 can be positioned at different distances from the inflow end 2913A.

In embodiments, the inflow markers 2947 can be formed in any shape to assist in the alignment of the transcatheter valve prosthesis 2901. In embodiments, as illustrated in FIG. 29, the inflow markers 2947 can be formed having a circular cross-sectional shape. In other embodiments, the inflow markers 2947 can be formed in any other 2D or 3D shape, which has any type of 2D or 3D cross-sectional shape, such as pins, dots, ovals, spheres, triangles, cones, squares, cubes, bars, crosses, bands, rings, letters, and combination thereof. One skilled in the art will realize that other configurations and shapes of the inflow markers 2947 may be provided to provide a benefit for a given application.

In embodiments, the inflow markers 2947 include radiopaque or other material that allow the inflow markers 2947 to be detected and/or viewed during the installation of the transcatheter valve prosthesis 2901. Examples of radiopaque materials include metals, e.g., stainless steel, titanium, tungsten, tantalum, gold, platinum, platinum-iridium, and/or other polymeric materials, e.g., nylon, polyurethane, silicone, PEBAX, PET, polyethylene, that have been mixed or compounded with compounds of barium, bismuth and/or zirconium, e.g., barium sulfate, zirconium oxide, bismuth sub-carbonate, etc.

In embodiments, the inflow markers 2947 can be attached to the stent 2911 within a containment member (not shown). The containment member is described in U.S. Patent Application No. 62/985,124 to Peterson et al., assigned to the same assignee of the present invention and herein incorporated by reference in its entirety, and can be configured as a hollow structure or opening in the stent 2911 which can receive the inflow markers 2947. In an embodiment, the containment member can be open to the interior and exterior of the stent 2911, thereby allowing the inflow markers 2947 to be exposed to the interior and exterior of the stent 2911 and increasing visibility at multiple angles. In some embodiments, the containment member can be open only to the interior or exterior of the stent 2911, thereby forming a cavity or depression in the stent 2911.

The transcatheter valve prosthesis 2901 also includes the first outflow marker 2949 to assist with the alignment of the commissures 2915 of the prosthetic valve 2919. The first outflow marker 2949 can operate to assist in rotational orientation of the stent 2911, as described below. Additionally, the first outflow marker 2949 can operate as a guide for determining a front or rear location the first outflow marker 2949 in 2D image during implantation, as described below. The first outflow marker 2949 is positioned towards the outflow end 2913B of the stent 2911.

In an embodiment, the first outflow marker 2949 can be circumferentially aligned with one of the inflow markers 2947, as illustrated in FIG. 29. The first outflow marker 2949 include radiopaque or other material that allow the first outflow marker 2949 to be detected and/or viewed during the installation of the transcatheter valve prosthesis 2901. Examples of radiopaque materials include metals, e.g., stainless steel, titanium, tungsten, tantalum, gold, platinum, platinum-iridium, and/or other polymeric materials, e.g., nylon, polyurethane, silicone, PEBAX, PET, polyethylene, that have been mixed or compounded with compounds of barium, bismuth and/or zirconium, e.g., barium sulfate, zirconium oxide, bismuth sub-carbonate, etc. The first outflow marker 2949 may be any size and shape described above with respect to the inflow markers 2947, and may be attached to the stent 2911 in any manner described above with respect to the inflow markers 2947.

Figure 31B:
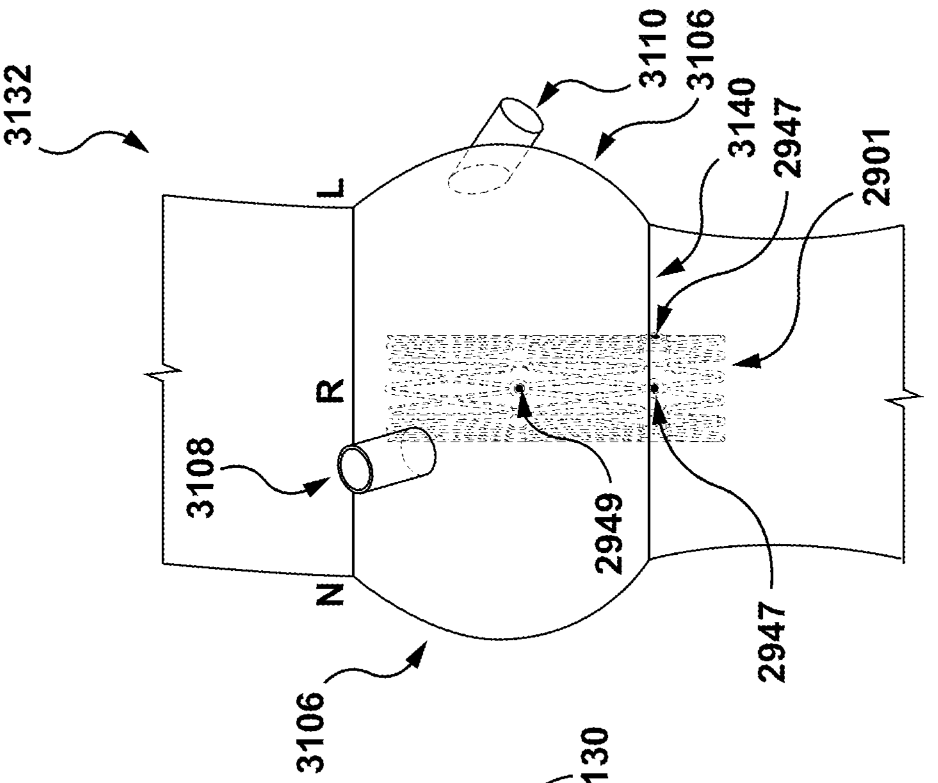
FIGS. 31A-31F illustrate various views of a target site for the transcatheter valve prosthesis of FIG. 29 in accordance with an embodiment hereof.
Figure 31A:
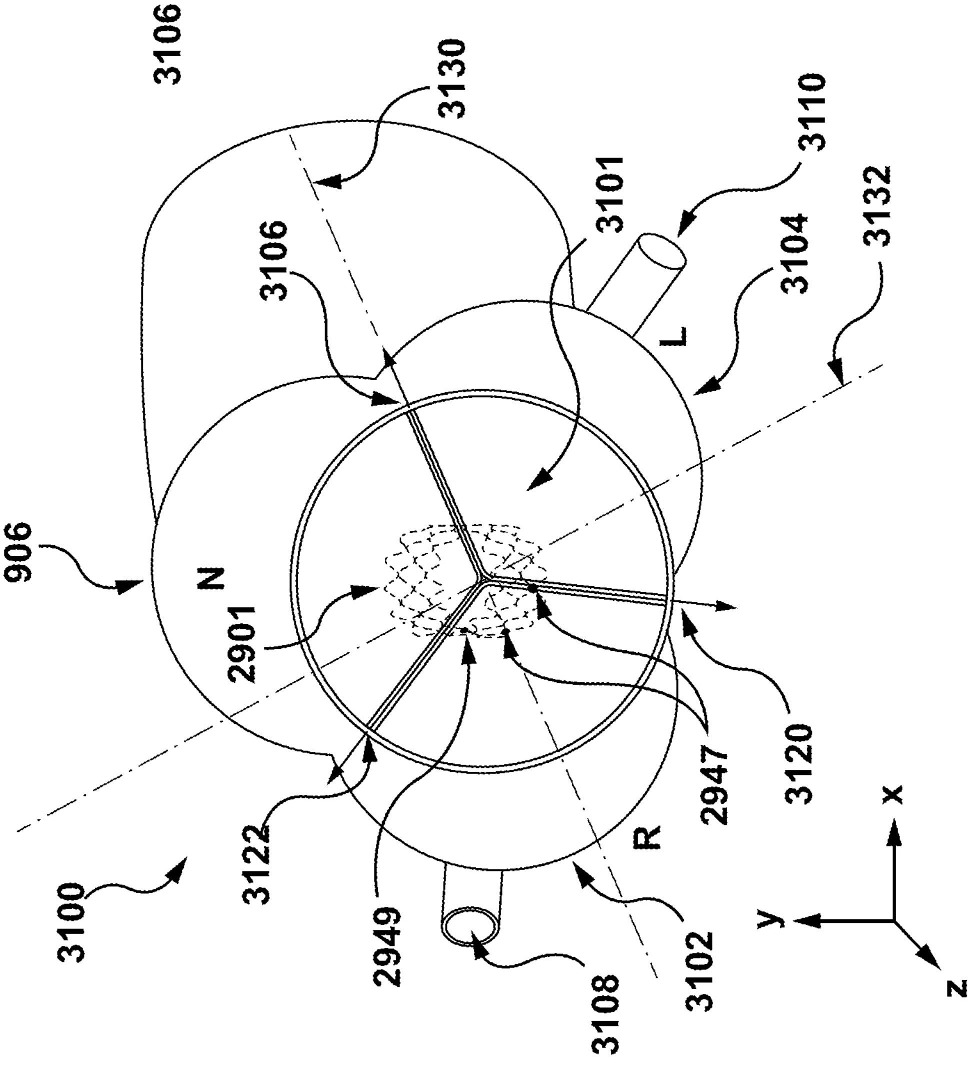
Figure 31C:
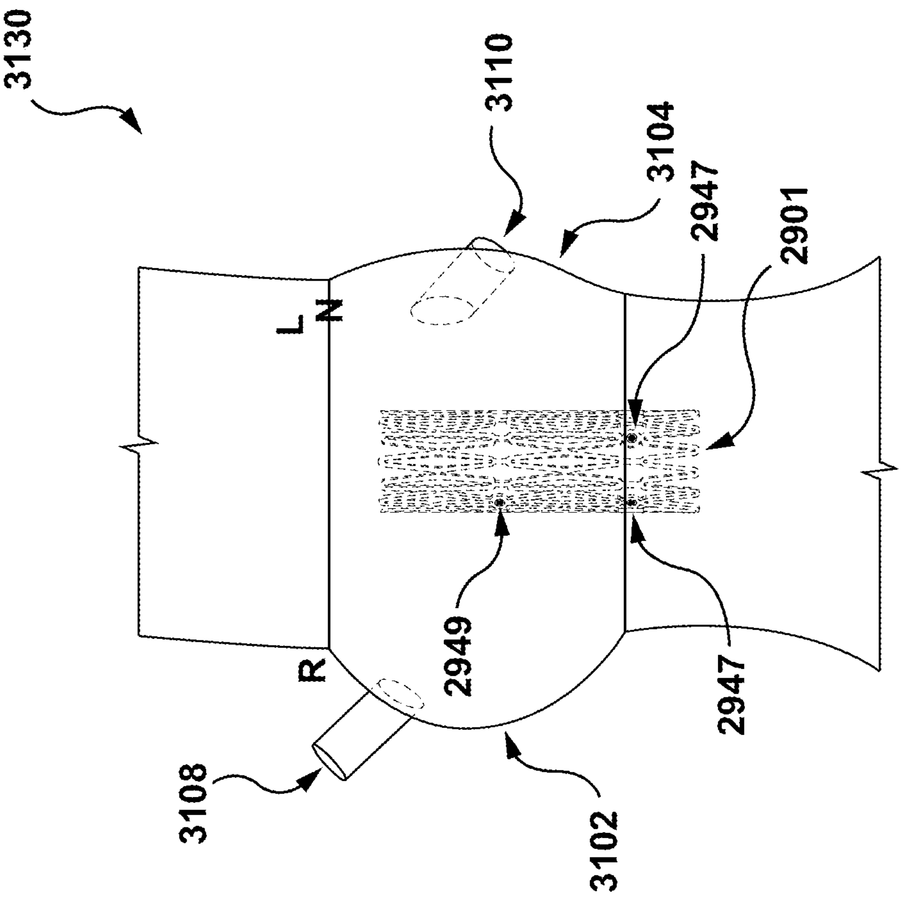

In embodiments, the inflow markers 2947 and the first outflow marker 2949 can be utilized in orientation (e.g., axial/annular alignment, tilt alignment, circumferential (rotational) alignment, etc.) of the transcatheter valve prosthesis 2901, in situ, during installation as described below with reference to FIGS. 31A-31E. A user utilizes the at least one outflow marker 2949 to interpret the circumferential orientation of the transcatheter valve prothesis 2901. FIGS. 31A-31C illustrate various views of a target site, e.g., an aortic heart valve, of the transcatheter valve prosthesis 2901. As illustrated in FIG. 31A, which is an annular view of the target site taken perpendicular to an annulus 3101, the target site includes three valve cusps of the aortic root, the right coronary cusp 3102, the left coronary cusp 3104 and the non-coronary cusp 3106. The region of the right coronary cusp 3102 includes ostia of the right coronary artery 3108. Likewise, the region of the left coronary cusp 3104 includes ostia of the left main coronary artery 3110.

When installing the transcatheter valve prosthesis 2901, it is desirable to properly align the stent 2911 within the target site. For example, the transcatheter valve prosthesis 2901 needs to be properly aligned, axially/annularly, so that the transcatheter valve prosthesis 2901 properly engages the native leaflets/tissue of the target site, e.g., the aortic annulus without causing conduction blockages by implanting too deep or causing an embolization of the transcatheter valve prosthesis 2901 because it was implanted too high. Likewise, the transcatheter valve prosthesis 2901 needs to be aligned circumferentially or rotationally. When being positioned, in situ, it is very important to avoid blocking the ostia of the right coronary artery 3108 and/or the left main coronary artery 3110. Proper circumferential or rotational orientation within the target site reduces the risk of blocking coronary access.

As illustrated in FIG. 31A, the right coronary cusp 3102, the left coronary cusp 3104, and the non-coronary cusp 3106 include commissure regions: right/left commissure 3120, right/non-coronary commissure 3122, and left/non-coronary commissure 3124. FIG. 31B illustrates a 2-D side view of the target site taken in an image plane 3132 (represented as a line in FIG. 31A). The image plane 3132 is approximately perpendicular to an image plane 3130 (represented as a line in FIG. 31A) in an x-direction and y-direction, and the image plane 3132 extends in the z-direction (a direction normal to the 2D view of FIG. 31A). FIG. 31C illustrates a 2-D side view of the target site taken in the image plane 3130. The image plane 3130 approximately bisects the right coronary cusp 3102 in the x-direction and y-direction (e.g., approximately perpendicular to the image plane 3132) and extends in the z-direction.

As illustrated in FIG. 31B, the inflow markers 2947 can be utilized to axially align the stent 2911 with features in the target site, e.g., basal plane 3140 of the right coronary cusp 3102, the left coronary cusp 3104 and the non-coronary cusp

Figures 31D, 31E:
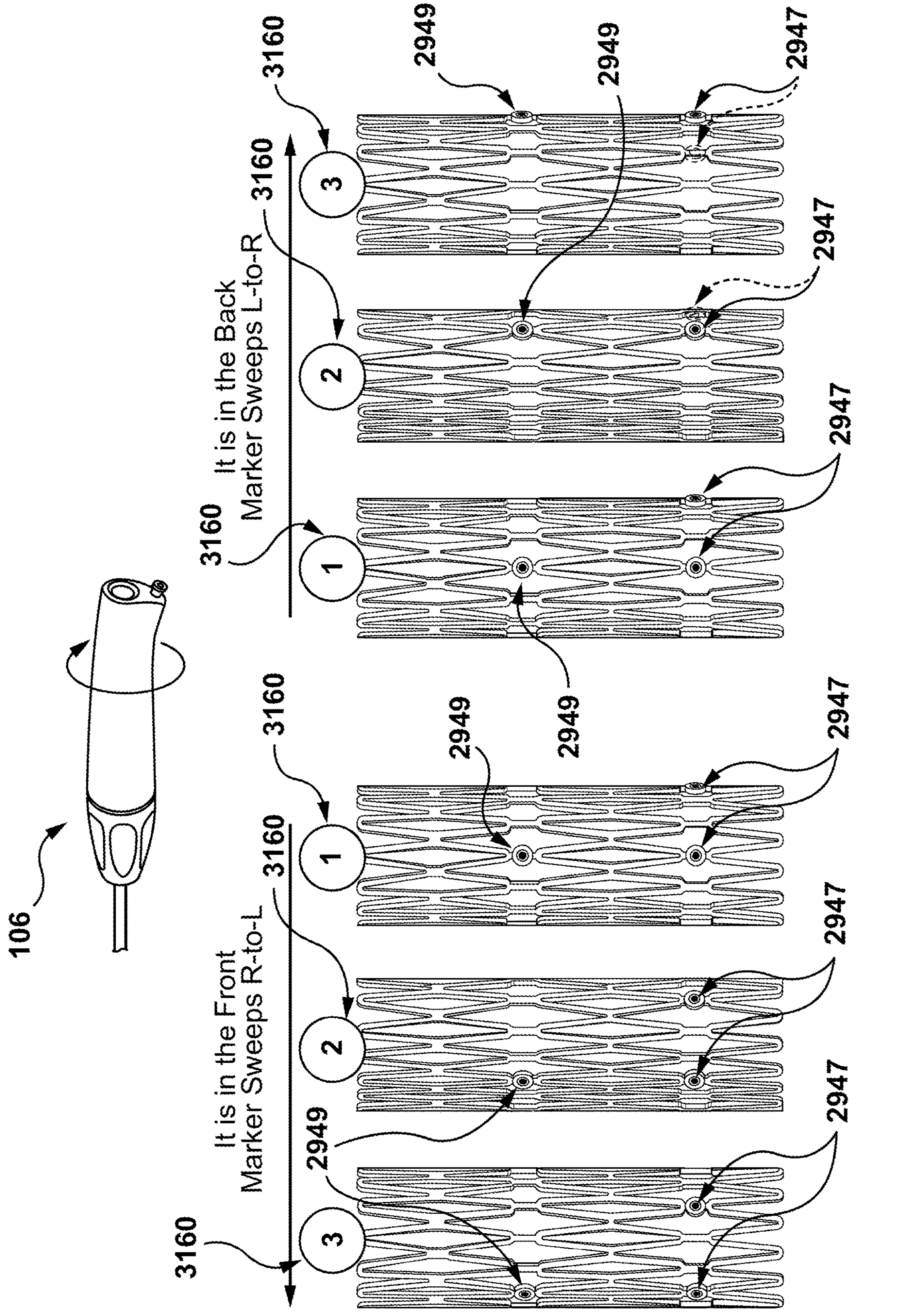
Figure 31F:
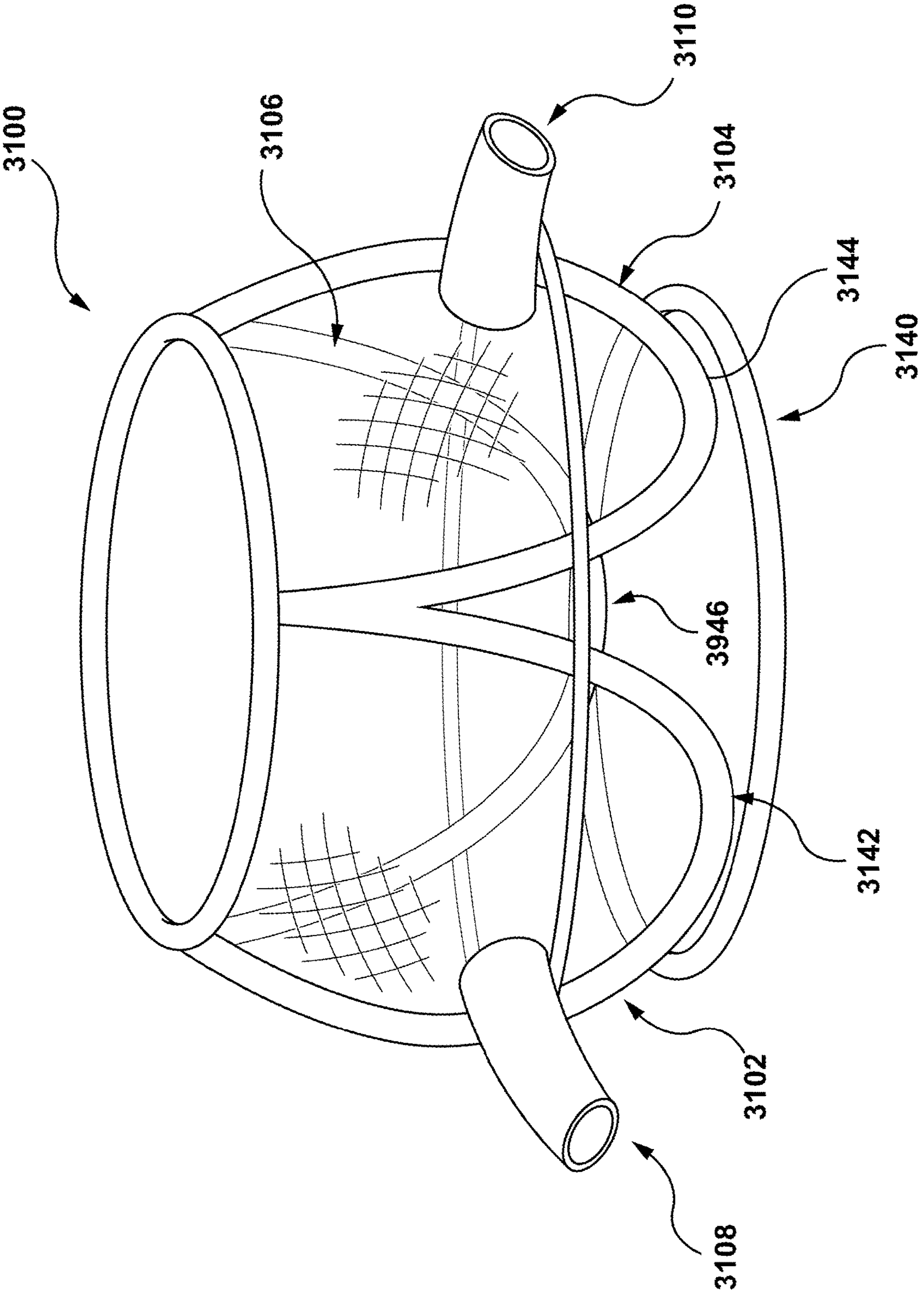

3106. For example, as illustrated in FIG. 31F, which is a three dimension view of the target site, the basal plane 3140 can be defined as a plane that intersects a nadir 3142 of the right coronary cusp 3102, a nadir 3144 of the left coronary cusp 3104, and a nadir 3146 of the non-coronary cusp 3106. To align the transcatheter valve prosthesis 2901, the stent 2911, the delivery system 100 (not shown) can be manipulated (e.g., advanced, retracted, etc.) until the inflow markers 2947 align with the basal plane 3140, as illustrated in FIG. 31B. As such, the transcatheter valve prosthesis 2901 can be positioned at a proper depth within the target site, thereby ensuring proper engagement with the native tissue.

Additionally, the inflow markers 2947 can be utilized to align the tilt and/or rotation of the stent 2911. For example, to align the transcatheter valve prosthesis 2901, the stent 2911, the delivery system can be manipulated (e.g., rotated, tilted, etc.) until the inflow markers 2947 form a predetermined pattern visible in the image captured in the image plane 3130 and/or 3132. For example, as illustrated in FIGS. 31D and 31E, the stent 2911 may include six (6) inflow markers 2947. As the stent 2911 is rotated, different numbers of the inflow markers 2947 may be visible in the 2D image, e.g., 6 markers in image 2 and 6 markers in image 3. In this example, to align the transcatheter valve prosthesis 2901, the delivery system can be manipulated (e.g., rotated, tilted, etc.) until all 6 of the inflow markers 2947 form a predetermined pattern, e.g., only 3 inflow markers 2947, that is visible in the image captured in the image plane 3132. In other words, 3 of the inflow markers 2947 overlap and obscure the other 3 of the inflow markers 2947 in the 2D image. If the image plane 3132 is aligned with the native anatomy as desired, the appearance of the predetermined pattern, e.g., only 3 inflow markers 2947, indicates the transcatheter valve prosthesis 2901 is approximately perpendicular to image plane 3132 indicating proper orientation (e.g., indicating proper tilt, proper rotation, etc.) of the transcatheter valve prosthesis 2901, as shown in FIG. 31D and FIGS. 31E, image 3.

In embodiments, the first outflow marker 2949 can be utilized to align circumferential or rotational orientation of the transcatheter valve prosthesis 2901. More particularly, the first outflow marker 2949 can allow a physician to correctly interpret the circumferential orientation of the transcatheter valve prosthesis 2901 and to clock or rotate the transcatheter valve prosthesis 2901 relative to the anatomy to correct the circumferential or rotational orientation, if necessary, to avoid blocking the ostia of the right coronary artery 3108 and/or the left main coronary artery 3110. In addition, first outflow marker 2949 clocks the commissures 2915 of the transcatheter valve prosthesis 2901 so they rotationally align with the native valve commissures. Commissure to commissure alignment (transcatheter valve prosthesis 2901 commissure to native commissure) may improve transcatheter valve prosthesis 2901 hemodynamics and leaflet durability. To align the transcatheter valve prosthesis 2901, the stent 2911 can rotated, in situ, by the delivery system to be positioned in a desired circumferential or rotational alignment.

For example, to avoid blocking the ostia of the left main coronary artery 3110, the first outflow marker 2949 can be positioned on the stent 2911 such that for proper rotational orientation of the stent 2911, the first outflow marker 2949 is aligned with the left/non-coronary commissure 3124 of the left coronary cusp 3104 and the non-coronary cusp 3106. As illustrated in FIG. 31B, if viewed in the image plane 3132 (parallel to the annulus 3101 and bisecting the right coronary cusp 3102), the first outflow marker 2949 can be rotated until the first outflow marker 2949 is centered in the image, thereby indicating alignment with the left/non-coronary commissure 3124. Likewise, for example, as illustrated in FIG. 31C, if viewed in the image plane 3130 (parallel to the annulus 3101 and is perpendicular to the image plane 3132), the first outflow marker 2949 can be rotated until the first outflow marker 2949 appears in the right of the image, thereby indicating alignment with the left/non-coronary commissure 3124. This alignment ensures that the first outflow marker 2949 (positioned at commissure 2915 of the prosthesis valve) does not block the ostia of the left main coronary artery 3110. Likewise, this alignment can allow the additional commissures 2915 to be aligned with the right/left commissure 3120 and the right/non-coronary commissure 3120. While the above describes the first outflow marker 2949 being aligned with the left/non-coronary commissure 3124, the first outflow marker 2949 can be aligned with other structure at the target site, e.g., right/left commissure 3120, right/non-coronary commissure 3122, etc.

In embodiments, the first outflow marker 2949 can also be used as a guide to a front or rear location of the first outflow marker 2949 appearing in 2D image. That is, the first outflow marker 2949 can be utilized to determine whether the first outflow marker 2949 is positioned on a side of the stent 2911 closest to the imaging apparatus (front location) or positioned on a side of the stent 2911 furthest from the imaging apparatus (rear location). FIGS. 31D and 31E illustrate several sequential images 3160 captured in the image plane 3132 as the transcatheter valve prosthesis 2901 is rotated in different directions using a handle 106 of the delivery system.

As illustrated in FIG. 31D and FIG. 31E, as the handle 106 is rotated in a clockwise direction (thereby rotating the stent 2911 counter-clockwise), the first outflow marker 2949 moves in the images 3160 to the right or left depending on the front or rear location of the first outflow marker 2949. That is, based on the transcatheter approach to the target site, a tip of the delivery system may be point in a direction opposite the direction of the handle 106 (e.g., in a direction back towards the handle 106), thereby causing the stent 2911 to rotate in a direction opposite a direction of rotation of the handle 106, when viewed in a 2D image. For example, as illustrated in FIG. 31D, as the handle 106 is rotated clockwise (thereby rotating the stent 2911 counter-clockwise), the first outflow marker 2949 moves from right to left in the images 3160, thereby indicating that the first outflow marker 2949 is in the front (where an emitter of the imaging device is positioned on the front side of the stent 2911 and the detector being is on a back side of the stent 2911). As illustrated in FIG. 31E, as the handle 106 is rotated clockwise (thereby rotating the stent 2911 counter-clockwise), the first outflow marker 2949 moves from left to right in the images 3160, thereby indicating that the first outflow marker 2949 is in the rear (on the back side of the stent 2911 relative to positioning of the imaging device). If the handle 106 is rotated counter-clockwise (thereby rotating the stent 2911 clockwise), the above movements would be reversed, e.g., left to right movement in the images would indicate front and right to left would indicate rear. While the particular movement of the first outflow marker 2949 is discussed above in reference to transcatheter approach, one skilled in the art will realize that the relative movement of the first outflow marker 2949 may change based on a different approach.

Figure 32:
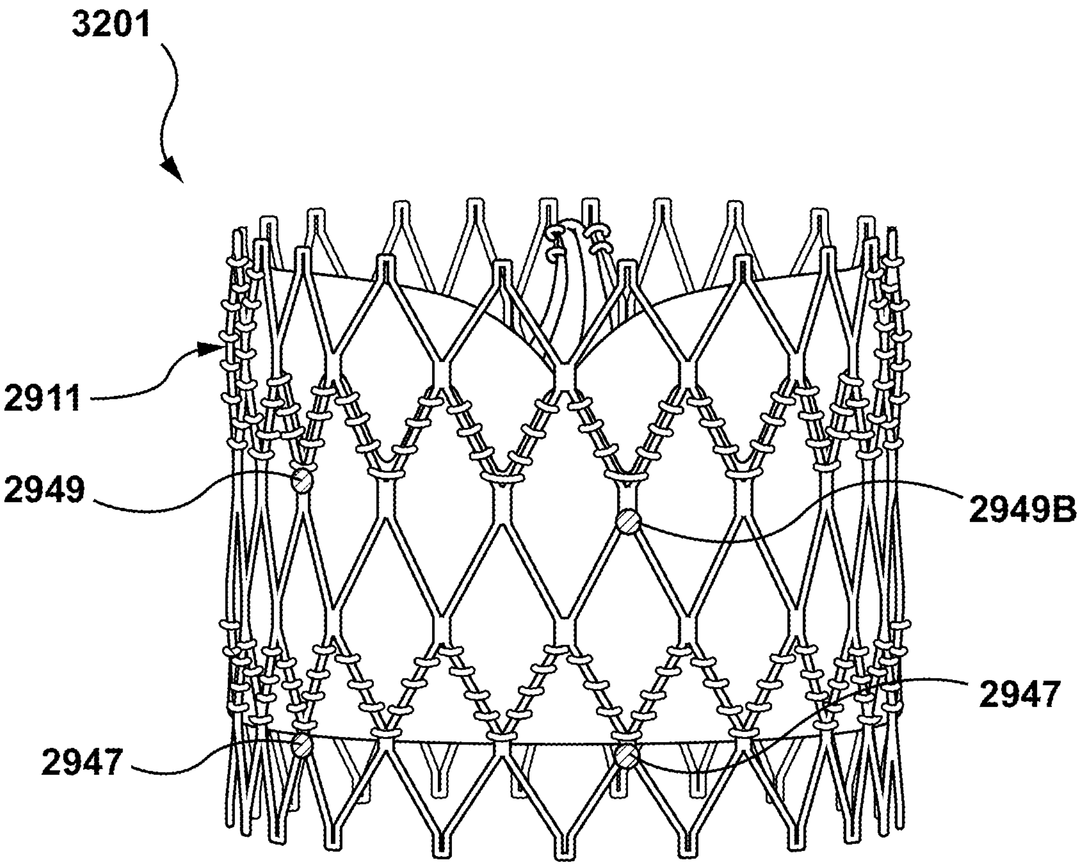
FIG. 32 is a side view of a transcatheter valve prosthesis that may be utilized as the balloon-expandable prosthesis of FIG. 1 in accordance with an embodiment hereof, wherein the transcatheter valve prosthesis is shown in its expanded configuration.

FIG. 32 illustrates a transcatheter valve prosthesis 3201 according to another embodiment herein in which the stent 2911 includes one or more inflow markers 2947, the first outflow marker 2949, and a second outflow marker 2949B. The second outflow marker 2949B can be positioned circumferentially and longitudinally offset to the first outflow marker 2949. In an embodiment, the first outflow marker 2949 and the second outflow marker 2949B are offset by sixty degrees circumferentially. In an embodiment, the first outflow marker 2949 is positioned closer to the outflow end 2513B of the stent 2511 relative to the second outflow marker 2949B. The inflow markers 2947, the first outflow marker 2949, and the second outflow marker 2949B can be utilized in orientation (e.g., axial/annular alignment, tilt alignment, circumferential (rotational) alignment, etc.) of the transcatheter valve prosthesis 3201, in situ, as described below with reference to FIGS. 33A-33D. Particularly, the second outflow marker 2949B can be utilized in combination with the first outflow marker 2949 to align the circumferential or rotation orientation of the stent 2911, as discussed below. In an embodiment, the first outflow marker 2949 is utilized for commissure alignment and the second outflow marker 2949B is utilized for locating coronary ostia at the native heart valve.

Figure 33B:
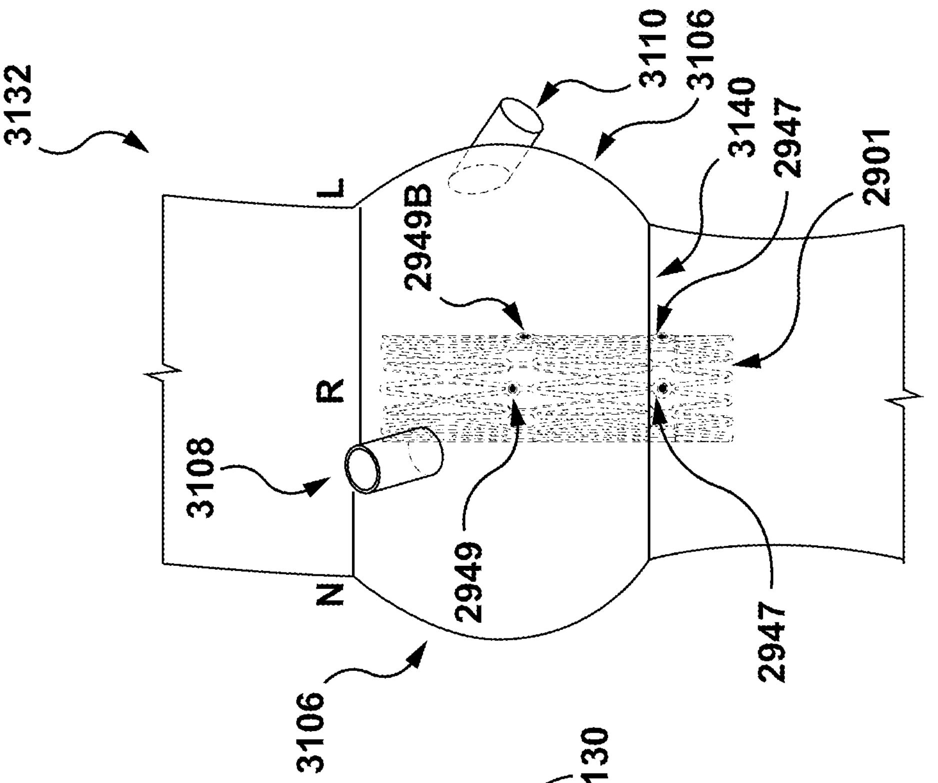
FIGS. 33A-33D illustrate various views of a target site for the transcatheter valve prosthesis of FIG. 32 in accordance with an embodiment hereof.
Figure 33A:
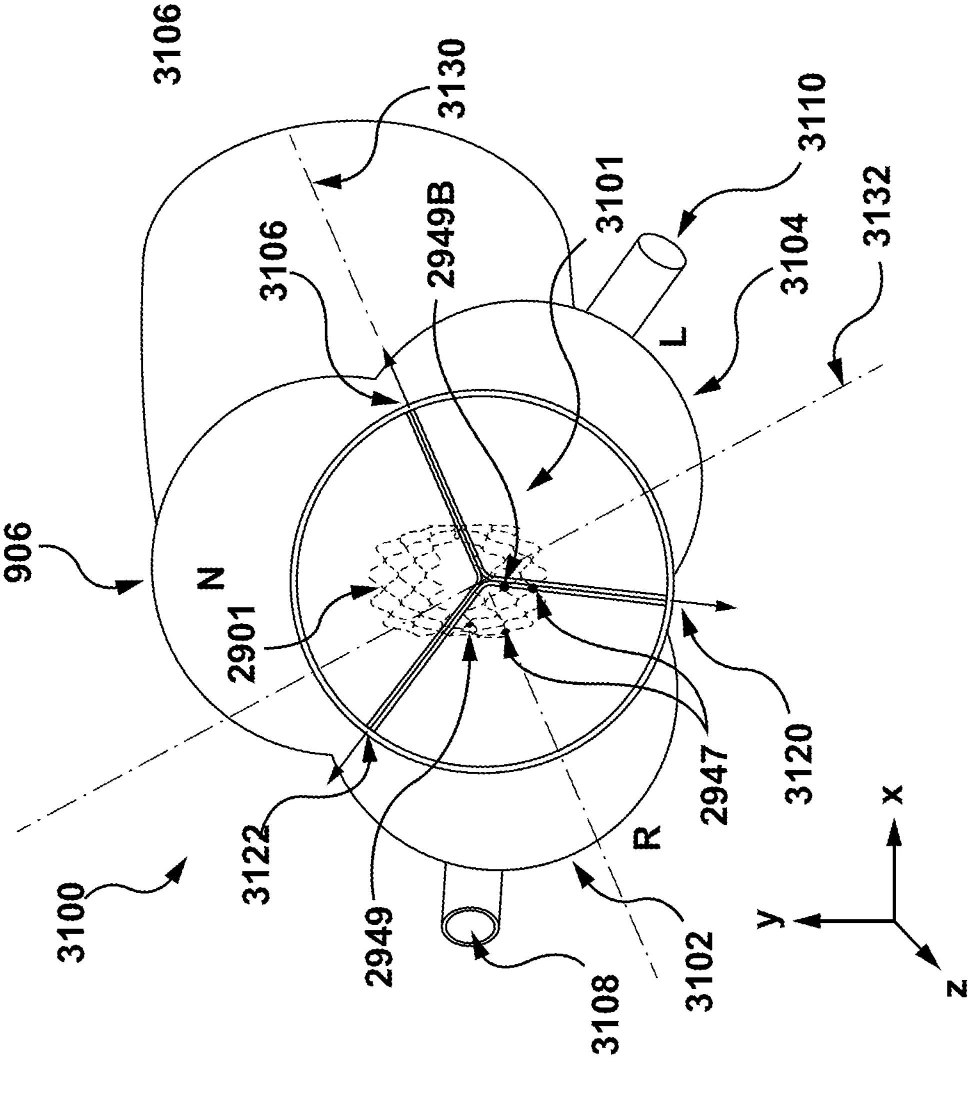

FIGS. 33A-33D illustrate various views of a target site e.g., an aortic heart valve, for the transcatheter valve prosthesis 3201. As illustrated in FIG. 33A, which is an annular view of the target site taken perpendicular to an annulus 3101, the target site includes three valve cusps of the aortic root, the right coronary cusp 3102, the left coronary cusp 3104 and the non-coronary cusp 3106. The region of the right coronary cusp 3102 includes ostia of the right coronary artery 3108. Likewise, the region of the left coronary cusp 3104 includes ostia of the left main coronary artery 3110.

Figure 33C:
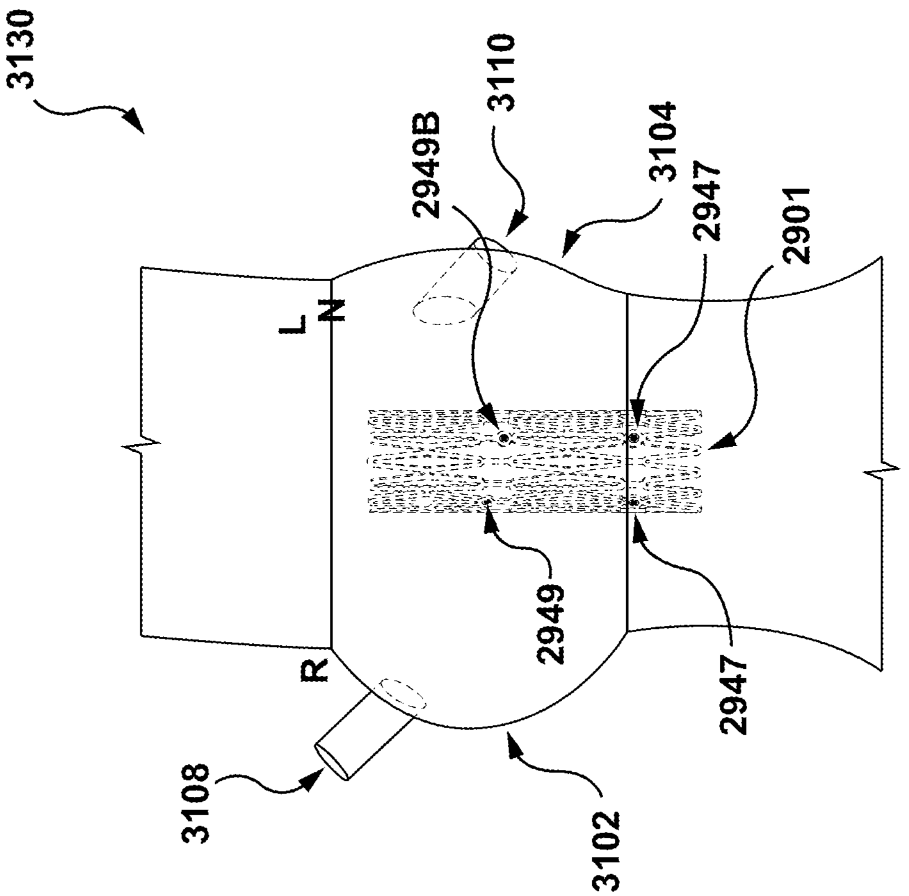

When installing the transcatheter valve prosthesis 3201, it is desirable to properly align the stent 2911 with the target site, as discussed above. For example, the transcatheter valve prosthesis 3201 needs to be properly aligned, axially/annularly, so that the transcatheter valve prosthesis 3201 properly engages the native tissue of the target site. Likewise, the transcatheter valve prosthesis 3201 needs to be aligned circumferentially or rotationally. When being positioned, in situ, it is very important to avoid blocking the ostia of the right coronary artery 3108 and/or the left main coronary artery 3110. Proper circumferential or rotational orientation within the target site may reduce the risk of blocking coronary access and may enhance hemodynamics and valve durability because of commissure-to-commissure alignment. As illustrated in FIG. 33A, the right coronary cusp 3102, the left coronary cusp 3104, and the non-coronary cusp 3106 include commissure regions: right/left commissure 3120, right/non-coronary commissure 3122, and left/non-coronary commissure 3124. FIG. 33B illustrates a 2-D side view of the target site taken in an image plane 3132 (represented as a line in FIG. 33A). The image plane 3132 is approximately perpendicular to an image plane 3130 (represented as a line in FIG. 33A) in an x-direction and y-direction, and the image plane 3132 extends in the z-direction (a direction normal to the 2D view of FIG. 33A). FIG. 33C illustrates a 2-D side view of the target site taken in the image plane 3130. The image plane 3130 approximately bisects the right coronary cusp 3102 in the x-direction and y-direction (e.g., approximately perpendicular to the image plane 3132) and extends in the z-direction.

As illustrated in FIG. 33B, the inflow markers 2947 can be utilized to axially align the stent 2911 with features in the target site, e.g., basal plane 3140 of the right coronary cusp 3102, the left coronary cusp 3104 and the non-coronary cusp 3106. For example, as discussed above with reference to FIG. 31F, which is a three dimension view of the target site, the basal plane 3140 can be defined as a plane that intersects a nadir 3134 of the right coronary cusp 3102, a nadir 3144 of the left coronary cusp 3104, and a nadir 3146 of the non-coronary cusp 3106. To align the transcatheter valve prosthesis 2901, the stent 2911, the delivery system can be manipulated (e.g., advanced, retracted, etc.) until the inflow markers 2947 align with the basal plane 3140, as illustrated in FIG. 33B. As such, the transcatheter valve prosthesis 2901 can be positioned at a proper depth within the target site, thereby ensuring proper engagement with the native tissue.

In embodiments, as described above with reference to FIGS. 31A-31E, the first outflow marker 2949, alone, can be utilized to align circumferential or rotational orientation of the transcatheter valve prosthesis 3201. For example, the first outflow marker 2949 can be aligned to the right/left commissure 3120, right/non-coronary commissure 3122, or left/non-coronary commissure 3124, thereby aligning the commissure 2915 to the right/left commissure 3120, right/non-coronary commissure 3122, or left/non-coronary commissure 3124, respectively. The second outflow marker 2949B, alone, can similarly be utilized to align circumferential or rotational orientation of the transcatheter valve prosthesis 3201. For example, the second outflow marker 2949B can be aligned to the right/left commissure 3120, right/non-coronary commissure 3122, or left/non-coronary commissure 3124. One skilled in the art will realize that the first outflow marker 2949 and/or the second outflow marker 2949B can be aligned to any feature at the target site.

In embodiments, the combination of the first outflow marker 2949 and the second outflow marker 2949B can be utilized to align circumferential or rotational orientation of the transcatheter valve prosthesis 3201. That is, the relative appearance and/or location in a 2D image can be utilized to align circumferential or rotational orientation of the transcatheter valve prosthesis 3201. In particular, the relative radial appearance in 2D image can indicate the relative positioning of the outflow markers 2949 and 2949B when an image plane is aligned to a desired feature at the target site. For example, to avoid blocking the ostia of the left main coronary artery 3110, the first outflow marker 2949 can be aligned with the right/left commissure 3120 of the right coronary cusp 3102 and the left coronary cusp 3104, as illustrated in FIG. 33A. Because the second outflow marker 2949B positioned adjacent to the first outflow marker 2949, the second outflow marker 2949B will be aligned near the left main coronary artery 3110.

The first outflow marker 2949 and the second outflow marker 2949B can be utilized in combination for circumferential or rotational alignment by setting up an image plane to be approximately parallel to the desired alignment feature and rotating the stent 2911 until the first outflow marker 2949 and the second outflow marker 2949B appear with no radial offset. When aligning the second outflow marker 2949B, the image plane can be aligned with a desired feature of the target site. For example, to align the second outflow marker 2949B to the left coronary artery, the imaging device can be positioned to produce an image in the image plane 3132, which is normal to the left/non-coronary commissure 3124. The relative radial appearance in a 2D image from the image plane 3132 can indicate the relative positioning of the first outflow marker 2949 and the second outflow marker 2949B can be utilized to indicate proper alignment. That is, proper alignment can be indicated by both the first outflow marker 2949 and the second outflow marker 2949B appearing on the right side of the image, as illustrated in FIG. 33B.

As illustrated in FIG. 33B, when the second outflow marker 2949B is aligned with the left coronary, the first outflow marker 2949 and the second outflow marker 2949B appear to be in a straight line (e.g., no radial offset) in the 2D image. This is due to the first outflow marker 2949 and the second outflow marker 2949B lying in the image plane 3132 or being perpendicular, along an axial line, to the image plane 3132 relative to the imaging device. As illustrated in FIG. 33C, when the first outflow marker 2949 and the second outflow marker 2949B do not approximately lie in or are perpendicular, along an axial line, to an image plane, e.g., image plane 3130, the first outflow marker 2949 and the second outflow marker 2949B appear radially offset.

Figure 33D:
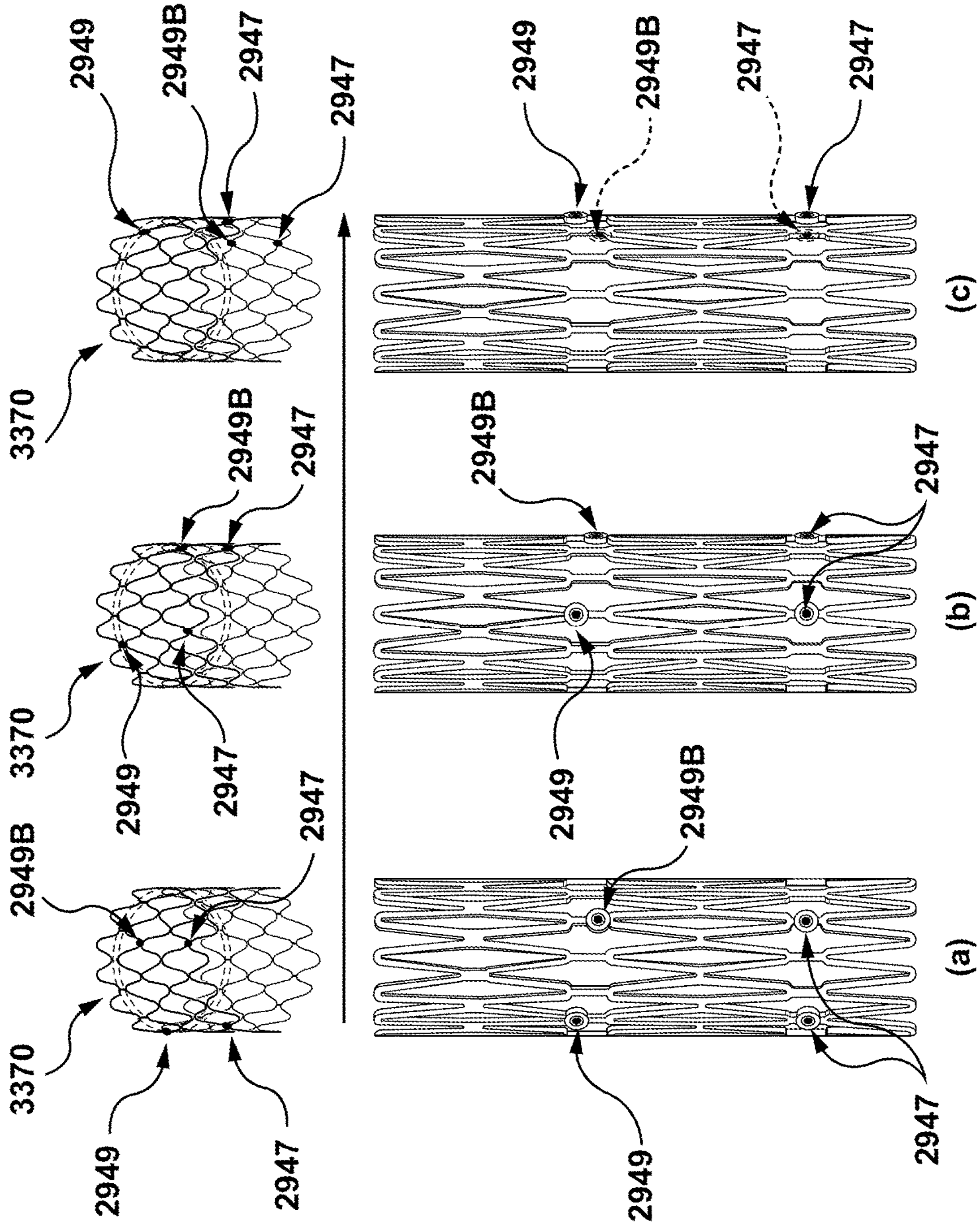

To align the transcatheter valve prosthesis 3201, the stent 2911 can be rotated, in situ, by the delivery system 100 until the first outflow marker 2949 and the second outflow marker 2949B do not appear radially offset, as illustrated in FIG. 33D. FIG. 33D illustrates several sequential images 3360 captured in the image plane 3130, and corresponding images 3370 captured in the annular image plane, as the transcatheter valve prosthesis 3201 is rotated using a handle 3150 of the delivery system. For example, in FIG. 33D, panel (a), the first outflow marker 2949 and the second outflow marker 2949B appear radially offset. To align the transcatheter valve prosthesis 2901, the stent 2911 can rotated, in situ, by the delivery system until the first outflow marker 2949 and the second outflow marker 2949B do not appear radially offset (e.g., in a straight line) as illustrated in FIG. 33D, and panel (c), thereby indicating the first outflow marker 2949 and the second outflow marker 2949B lying in the image plane 3130 or being perpendicular to the image plane 3130 relative to the imaging device.

In embodiments, the first outflow marker 2949 and/or the second outflow marker 2949B, alone, can also be used as a guide to the front or rear location of the first outflow marker 2949 appearing in 2D image, as described above. The relative motion of the first outflow marker 2949 and the outflow markers 2949B, when rotated, can be used to indicate the front or rear location of the first outflow marker 2949 appearing in 2D image. In particular, the right or left location of the first outflow marker 2949 relative to the outflow markers 2949B, during rotation of the stent 2911, can indicate the front or rear location. For example, if the second outflow marker 2949B is placed to the left of the first outflow marker 2949, the appearance of the outflow marker to the left of the first outflow marker 2949, during rotation, would indicate a front location, as shown in FIG. 33D, panel (a). Likewise, the appearance of the outflow marker to the right of the first outflow marker 2949 would indicate a rear location. While the particular movement of the first outflow marker 2949 is discussed above in reference to transcatheter approach, one skilled in the art will realize that the relative movement of the first outflow marker 2949 may change based on a different approach.

In any embodiment described above, the inflow markers 2947, the first outflow marker 2949, and/or the second outflow marker 2949B can be formed as a directional marker that assists in the circumferential (rotational) orientation based on the shape of the directional marker as described in more detail in U.S. Patent Appl. No. 62/985,124 to Peterson et al., previously incorporated by reference herein. For example, the inflow markers 2947, the first outflow marker 2949, and/or the second outflow marker 2949B include formed in and/or can include an element that appears differently based on the rotational orientation, e.g., “C-shaped,” “P-shaped,” etc. The directional marker can assist a physician with correctly orienting the transcatheter valve prosthesis 2901 and/or 3201, in situ. The directional marker can allow a physician to correctly interpret the circumferential orientation of the transcatheter valve prosthesis 2901 and/or 3201 and to clock or rotate the transcatheter valve prosthesis 2901 and/or 3201 relative to the anatomy to correct the circumferential or rotational orientation if necessary. As discussed above, when being positioned in situ, it is very important to avoid blocking the ostia of the right coronary artery and/or the left main coronary artery and attaining commissure-to-commissure alignment. Proper circumferential or rotational orientation within the native anatomy reduces the risk of blocking coronary access. The transcatheter valve prosthesis 2901 and/or 3201 is rotatable, in situ, by the delivery system 100 to be positioned in a desired orientation. When formed as a directional marker, the inflow markers 2947, the first outflow marker 2949, and/or the second outflow marker 2949B can further assist the physician to determine the orientation of the stent 2911, in situ, and rotate the transcatheter valve prosthesis relative to the anatomy if needed to avoid blocking the coronary arteries and attaining commissure-to-commissure alignment.

For example, the inflow markers 2947, the first outflow marker 2949, and/or the second outflow marker 2949B can be formed as directional marker that includes a C-shaped feature. Because the C-shape of the directional marker looks different when viewed from a front view or position as compared to when viewed from a reverse view or position, the physician can determine whether a particular portion of the stent 2911, the first outflow marker 2949, etc., is facing toward or away from the viewing direction. In other words, the C-shape of the directional marker can be an axially non-symmetrical element such that depending upon the location, in situ, the C-shape of the directional marker may be displayed to the physician as a “C” or may be displayed to the physician backwards or as a mirror image of a “C”. Since the optimal circumferential or rotational orientation of the transcatheter valve prosthesis 2901 and/or 3201 relative to the coronary arteries can be verified prior to releasing the transcatheter valve prosthesis 2901 and/or 3201 from the delivery system, the physician can ensure that the transcatheter valve prosthesis 2901 and/or 3201 is properly oriented in the native anatomy so as to not block the coronary arteries and commissure-to-commissure alignment. In embodiments, the inflow markers 2947, the first outflow marker 2949, and/or the second outflow marker 2949B can be formed as directional marker that is formed as or includes any letter, number, symbol, or shape that looks different when viewed from a front view or position as compared to when viewed from a reverse view or position, e.g., a letter “P,” a letter “S,” a number “7,” etc.

FIG. 34 illustrates a method 3400 of operating of a delivery system utilizing the inflow markers 2947, the first outflow marker 2949, and/or the second outflow marker 2949B in accordance with an embodiment hereof. One skilled in the art will realize that FIG. 34 illustrates one example of steps that can be performed and that existing steps illustrated in FIG. 34 may be removed and/or additional steps may be added to the method 3400.

In step 3402, an image plane of an imaging device is aligned with anatomy at a target site. For example, as discussed above with reference to FIGS. 33A-33D, the imaging device, producing images, can be aligned with the anatomy of the patient (e.g., an annulus) to produce images in an image plane 3130 and/or 3132. One skilled in the art will realize that the images in the image plane 3130 and/or 3132 are examples and that the operations and procedures described herein can be performed using 2D image produced in any image plane of the target site and/or using 3D images of the target site.

In step 3404, an implantable medical device is delivered to the target site. In embodiments, the transcatheter valve prosthesis 2901 and/or 3201 can be loaded onto a delivery system (not shown), which is then utilized to deliver the implantable medical device to the target site. Delivery of the transcatheter valve prosthesis 2901 and/or 3201 can be accomplished via any type of procedure utilized to install medical devices in patients. For example, delivery of the transcatheter valve prosthesis 2901 and/or 3201 by the delivery system 100 can be accomplished via a percutaneous transfemoral approach or a transapical approach directly through the apex of the heart via a thoracotomy, or may be positioned within the desired area of the heart via different delivery methods known in the art for accessing heart valves. During delivery, the stent 2911 of the transcatheter valve prosthesis 2901 and/or 3201 remains compressed (in a crimped state) until it reaches a target site, e.g., a diseased native heart valve.

In step 3406, the implantable medical device is positioned in an axial direction at the target site. In embodiments, the inflow markers 2947 of the transcatheter valve prosthesis 2901 and/or 3201 can be utilized to position the stent 2911 in the axial direction relative to native annulus. This may ensure a correct implant depth of the transcatheter valve prosthesis 2901 and/or 3201.

For example, the inflow markers 2947 can be utilized to axially/annularly align the stent 2911 with features in the target site, e.g., edge or terminus 3140 of the right cusp 3102, the left cusp 3104 and the non-coronary cusp 3106. For example, the inflow markers 2947 can be aligned with the edge 3140 of the right cusp 3102, the left cusp 3104 and the non-coronary cusp 3106. To align the transcatheter valve prosthesis 2901 and/or 3201, the stent 2911, the delivery system can be manipulated (e.g., advanced, retracted, etc.) until the inflow markers 2947 align with the edge 3140 of the right coronary cusp 3102, the left coronary cusp 3104 and the non-coronary cusp 3106.

In step 3408, a circumferential or rotational orientation of the implantable medical device is aligned at the target site. In embodiments, the outflow markers 2949 and outflow markers 2949B operate solely or in combination to provide visual references to an orientation of the transcatheter valve prosthesis 2901 and/or 3201 relative to the native structure of the target site of the transcatheter valve prosthesis 2901 and/or 3201 is being installed.

For example, the first outflow marker 2949 or the second outflow marker 2949B can be utilized to align circumferential or rotational orientation of the transcatheter valve prosthesis 2901 and/or 3201. More particularly, the first outflow marker 2949 or the second outflow marker 2949B can allow a physician to correctly interpret the circumferential orientation of the transcatheter valve prosthesis 2901 and to clock or rotate the transcatheter valve prosthesis 2901 and/or 3201 relative to the anatomy to correct the circumferential or rotational orientation, if necessary, to avoid blocking the ostia of the right coronary artery 3108 and/or the left main coronary artery 3110 and attain commissure-to-commissure alignment. To align the transcatheter valve prosthesis 2901 and/or 3201, the stent 2911 can rotated, in situ, by the delivery system to be positioned in a desired circumferential or rotational alignment using the first outflow marker 2949 or the second outflow marker 2949B as a visual reference, as described above.

Likewise, for example, the first outflow marker 2949 and the second outflow marker 2949B can be utilized in combination for circumferential or rotational alignment by rotating the stent 2911 until the first outflow marker 2949 and the second outflow marker 2949B appear with no radial offset. For instance, to align the second outflow marker 2949B to the left coronary, the imaging device can be positioned (in step 3402) to produce an image in the image plane 3132, which is parallel to the annulus 3101 and perpendicular to the left/non-coronary commissure 3124. As illustrated in FIG. 33B (as discussed above), when the second outflow marker 2949B is aligned with the left coronary, the first outflow marker 2949 and the second outflow marker 2949B appear to be in a straight line (e.g., no radial offset) in the 2D image. This is due to the first outflow marker 2949 and the second outflow marker 2949B lying in the image plane 3132 or being perpendicular to the image plane 3132 relative to the imaging device. To align the transcatheter valve prosthesis 3201, the stent 2911 can be rotated, in situ, by the delivery system 100 until the first outflow marker 2949 and the second outflow marker 2949B do not appear radially offset, as illustrated in FIG. 33D (described above).

Additionally, for example, the inflow markers 2947 can be utilized to align the tilt and/or rotation of the stent 2911. For example, to align the transcatheter valve prosthesis 2901 and/or 3201, the stent 2911, the delivery system, can be manipulated (e.g., rotated, tilted, etc.) until the inflow markers 2947 form a predetermined pattern visible in the image captured in the image plane 3130 and/or 3132, for example, as described above with reference to FIGS. 31A-31E.

In step 3410, the implantable medical device is deployed at the target site. In embodiments, the transcatheter valve prosthesis 2901 and/or 3201 can be deployed. In embodiments, the transcatheter valve prosthesis 2901 and/or 3201 can be deployed using the balloon 110 of the delivery system 100. The delivery system is then removed and the transcatheter valve prosthesis 2901 and/or 3201 remains deployed within the native target heart valve.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. For example, the handle having both torqueing and steering mechanisms may be utilized in any type of catheter device. The catheter device having such a handle may include the strain relief component and the valve relief components described herein, or may be used without the strain relief and valve relief components. Conversely, the strain relief component and the valve relief components described herein may be incorporated into any type of catheter device, including a catheter device having a handle without the torqueing and steering mechanisms described herein. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

The invention claimed is:

1. A balloon catheter comprising:

an outer shaft having an elongate tubular body extending from a proximal end to a distal end and defining a central lumen therethrough, the elongate tubular body having a proximal portion, a distal portion, and an intermediate portion extending between the proximal portion and the distal portion;

a balloon attached to the distal end of the elongate tubular body, the balloon being expandable from a first diameter to a second diameter greater than the first diameter; and an inflation lumen, the inflation lumen being in fluid communication with an interior of the balloon, wherein the proximal portion includes a first polymer having a first stiffness and a first portion of a tubular braid component extending within the first polymer, and wherein the intermediate portion includes a second polymer having a second stiffness and a second portion of the tubular braid component extending within the second polymer, and wherein the distal portion includes a third polymer having a third stiffness, a third portion of the tubular braid component extending within the third polymer, and a hypotube extending within the third polymer, the hypotube being configured for elastic deformation and having a proximal end, a distal end, a length between the proximal end and the distal end, and a sidewall cut with a pattern, and wherein along an overlap segment of the distal portion, the third portion of the tubular braid component overlaps the length of the hypotube or the length of the hypotube overlaps the third portion of the tubular braid component, and wherein the second stiffness is less than the first stiffness and the third stiffness is less than the second stiffness, and wherein the balloon is disposed distal to the hypotube.

2. The balloon catheter of claim 1, further comprising a handle coupled to the proximal end of the elongate tubular body, wherein a pull wire lumen is defined in a sidewall of the elongate tubular body, the pull wire lumen terminating proximal to the distal end of the elongate tubular body, and further comprising a pull wire slidingly disposed through the pull wire lumen, wherein a distal end of the pull wire is coupled to the sidewall of the elongate tubular body and a proximal end of the pull wire is coupled to an actuator of the handle, and wherein the pull wire is operable to bend the elongate tubular body for steering the balloon catheter in situ.

3. The balloon catheter of claim 2, wherein the sidewall of the elongate tubular body has a non-uniform cross-sectional thickness, the pull wire lumen extending within a thicker wall section of the sidewall.

4. The balloon catheter of claim 2, wherein the pull wire lumen is formed via an elongated radial protrusion that extends along an inner surface of the elongate tubular body and protrudes into the central lumen of the elongate tubular body.

5. The balloon catheter of claim 2, wherein the sidewall of the elongate tubular body has a substantially uniform cross-sectional thickness, the pull wire lumen having a flattened oval cross-section and the pull wire having a flattened longitudinal profile.

6. The balloon catheter of claim 2, wherein the sidewall of the elongate tubular body has a non-uniform cross-sectional thickness such that the sidewall includes a thicker wall section and a thinner wall section that is diametrically opposed to the thicker wall section, the pull wire lumen extending within the thicker wall section of the sidewall and the thinner wall section of the sidewall including a fourth polymer having a fourth stiffness, the fourth stiffness being greater than the first stiffness.

7. The balloon catheter of claim 2, wherein the sidewall of the elongate tubular body has a substantially uniform cross-sectional thickness and a first balancing lumen is defined in the sidewall of the elongate tubular body, the first balancing lumen being diametrically opposed to the pull wire lumen.

8. The balloon catheter of claim 7, wherein the pull wire is a first pull wire, and the balloon catheter further comprises a second pull wire slidingly disposed through the first balancing lumen, wherein the second pull wire is operable to bend the elongate tubular body for steering the balloon catheter in situ.

9. The balloon catheter of claim 7, further comprising:

a second balancing lumen defined in the sidewall of the elongate tubular body, the second balancing lumen being offset by approximately ninety degrees from the pull wire lumen; and a third balancing lumen defined in the sidewall of the elongate tubular body, wherein the third balancing lumen is diametrically opposed to the second balancing lumen.

10. The balloon catheter of claim 9, wherein the pull wire is a first pull wire, and the balloon catheter further comprises a second pull wire slidingly disposed through the first balancing lumen, wherein the second pull wire is operable to bend the elongate tubular body for steering the balloon catheter in situ;

a third pull wire slidingly disposed through the second balancing lumen, wherein the third pull wire is operable to bend the elongate tubular body for steering the balloon catheter in situ, and a fourth pull wire slidingly disposed through the third balancing lumen, wherein the fourth pull wire is operable to bend the elongate tubular body for steering the balloon catheter in situ.

11. The balloon catheter of claim 2, wherein the handle includes a steering indicator that displays to a user an amount of bending of the elongate tubular body.

12. The balloon catheter of claim 11, wherein the steering indicator includes a transparent tube disposed over a slider rack and a longitudinal position of the slider rack with the transparent tube corresponds to the amount of bending of the elongate tubular body.

13. The balloon catheter of claim 1, wherein the third portion of the tubular braid component extends distally beyond the distal end of the hypotube.

14. The balloon catheter of claim 1, wherein the third portion of the tubular braid component has a distal end that longitudinally terminates distal to the distal end of the hypotube.

15. The balloon catheter of claim 1, wherein the third polymer is disposed in and around the third portion of the tubular braid component and the length of the hypotube along the overlap segment of the distal portion of the elongate tubular body.

16. The balloon catheter of claim 15, wherein the third polymer extends through voids of the pattern of the sidewall of the hypotube and voids of the tubular braid component.

17. The balloon catheter of claim 1, wherein the first stiffness is constant along a length of the proximal portion and the second stiffness is constant along a length of the intermediate portion.

18. The balloon catheter of claim 1, wherein the third stiffness varies along a length of the distal portion due to the pattern of the sidewall of the hypotube and wherein the pattern of the sidewall of the hypotube defines a plurality of successive windings having a void between each pair of adjacent successive windings and wherein the plurality of successive windings includes a first plurality of successive windings, a second plurality of successive windings, and a third plurality of successive windings, the second plurality of successive windings being disposed distal to the first plurality of successive windings and the third plurality of successive windings being disposed distal to the second plurality of successive windings, wherein each winding of the first plurality of successive windings has a first width, each winding of the second plurality of successive windings has a second width, and each winding of the third plurality of successive windings has a third width, the second width being greater than the third width and the first width being greater than the second width.

19. The balloon catheter of claim 18, wherein each void between each pair of adjacent successive windings is the same width.

20. The balloon catheter of claim 1, wherein the elongate tubular body has a length from the proximal end to the distal end thereof and the proximal portion extends between 75-90% of the length of the elongate tubular body, the intermediate portion extends between 5-10% of the length of the elongate tubular body, and the distal portion extends between 5-15% of the length of the elongate tubular body.

* * * * *